US010653760B2

(12) United States Patent
Lucas

(10) Patent No.: US 10,653,760 B2
(45) Date of Patent: May 19, 2020

(54) COMPOSITIONS AND METHODS FOR REDUCING ORGAN REJECTION BY REDUCING HEPARAN SULFATE IN DONOR TRANSPLANTS

(71) Applicant: University of Florida Research Foundation, Incorporated, Gainesville, FL (US)

(72) Inventor: Alexandra Rose Lucas, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 256 days.

(21) Appl. No.: 15/742,092

(22) PCT Filed: Jul. 7, 2016

(86) PCT No.: PCT/US2016/041372
§ 371 (c)(1),
(2) Date: Jan. 5, 2018

(87) PCT Pub. No.: WO2017/007956
PCT Pub. Date: Jan. 12, 2017

(65) Prior Publication Data
US 2018/0193437 A1 Jul. 12, 2018

Related U.S. Application Data

(60) Provisional application No. 62/189,548, filed on Jul. 7, 2015.

(51) Int. Cl.
*A61K 39/00* (2006.01)
*A61P 37/06* (2006.01)
*A61K 39/275* (2006.01)
*A61P 37/00* (2006.01)

(52) U.S. Cl.
CPC .......... *A61K 39/001* (2013.01); *A61K 39/275* (2013.01); *A61P 37/06* (2018.01); *A61K 2039/58* (2013.01); *C12N 2710/24033* (2013.01)

(58) Field of Classification Search
CPC .................................................. A61K 39/001
See application file for complete search history.

(56) References Cited

U.S. PATENT DOCUMENTS 6,495,515 B1  12/2002  McFadden et al.
2009/0221472 A1  9/2009  Lucas et al.

OTHER PUBLICATIONS

Bartee et al. Chapter 10 M-T7. Measuring Chemokine-Modulating Activity, Methods in Enzymology , published on May 4, 2009, vol. 460, pp. 209-228.*
Bedard et al. PDF Jul. 15, 2003, vol. 76 (1), pp. 249-252.*
PCT/US2016/041372, Sep. 13, 2016, Invitation to Pay Additional Fees.
PCT/US2016/041372, Nov. 30, 2016, International Search Report and Written Opinion.
PCT/US2016/041372, Jan. 18, 2018, International Preliminary Report on Patentability.
Invitation to Pay Additional Fees for Application No. PCT/US2016/041372 mailed on Sep. 13, 2016.
International Search Report and Written Opinion for Application No. PCT/US2016/041372 dated Nov. 30, 2016.
International Preliminary Report on Patentability for Application No. PCT/US2016/041372 dated Jan. 18, 2018.
Bartee et al., Defining the anti-inflammatory activity of a potent myxomaviral chemokine modulating protein, M-T7, through site directed mutagenesis. Cytokine. Jan. 2014;65(1):79-87. doi: 10.1016/j.cyto.2013.10.005. Epub Nov. 5, 2013.
Dai et al., Inhibition of chemokine-glycosaminoglycan interactions in donor tissue reduces mouse allograft vasculopathy and transplant rejection. PLoS One. May 6, 2010;5(5):e10510. doi: 10.1371/journal.pone.0010510.

* cited by examiner

*Primary Examiner* — Bao Q Li
(74) *Attorney, Agent, or Firm* — Wolf, Greenfield & Sacks, P.C.

(57) ABSTRACT

Disclosed here are polypeptides, derived from the Myxomavirus-derived secreted glycoprotein, M-T7, comprising point mutations that interfere with chemokine-glycosaminoglycan binding. Compositions containing such M-T7 derived polypeptides with point mutations are therefore useful in preventing, blocking and/or reducing rejection of a transplant.

11 Claims, 32 Drawing Sheets

Specification includes a Sequence Listing.

A.

B.

C57BL/6 donor kidney
Saline Treatment
High power-
with inflammation

NDST1$^{-/-}$ donor kidney
Saline Treatment
High power-
no inflammation

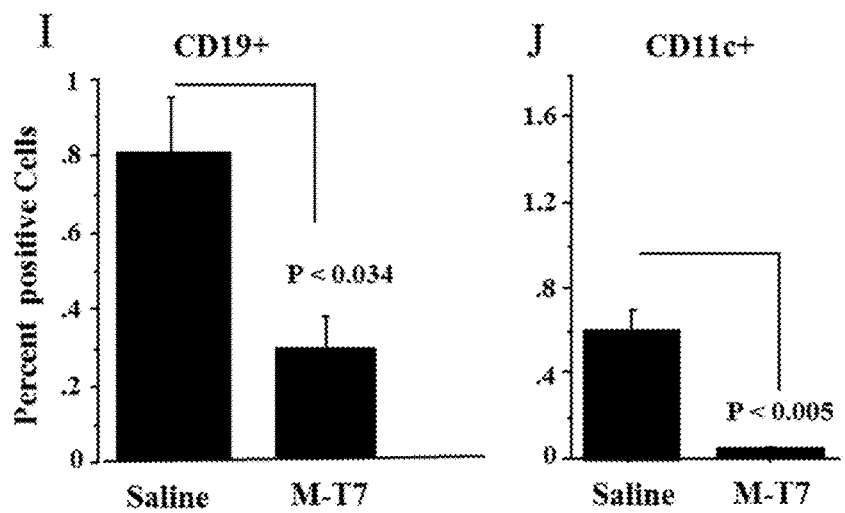
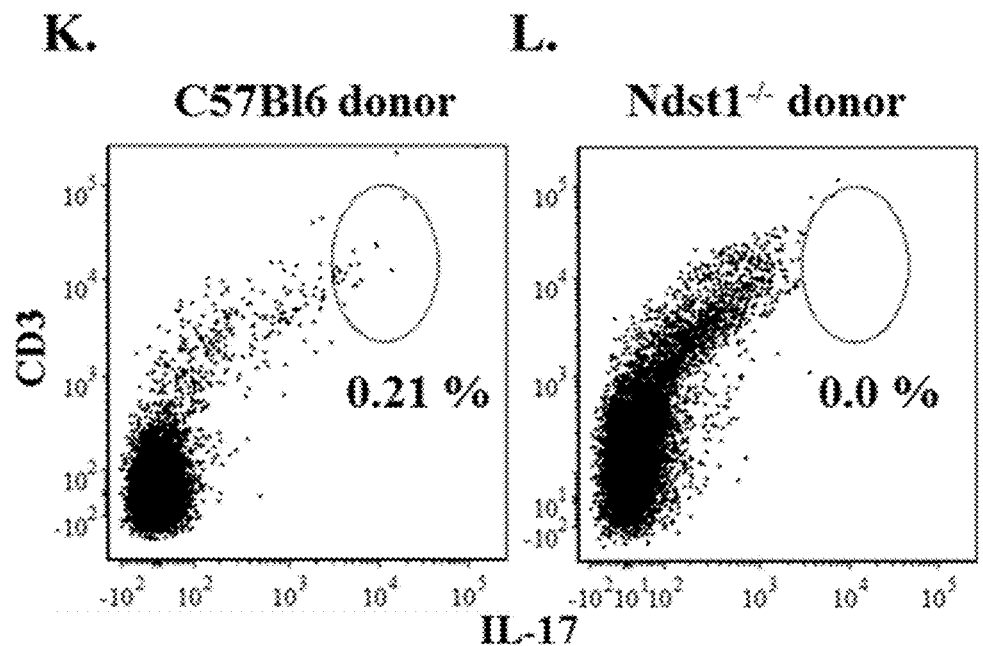
FIG. 8I, FIG. 8J, FIG. 8K, FIG. 8L

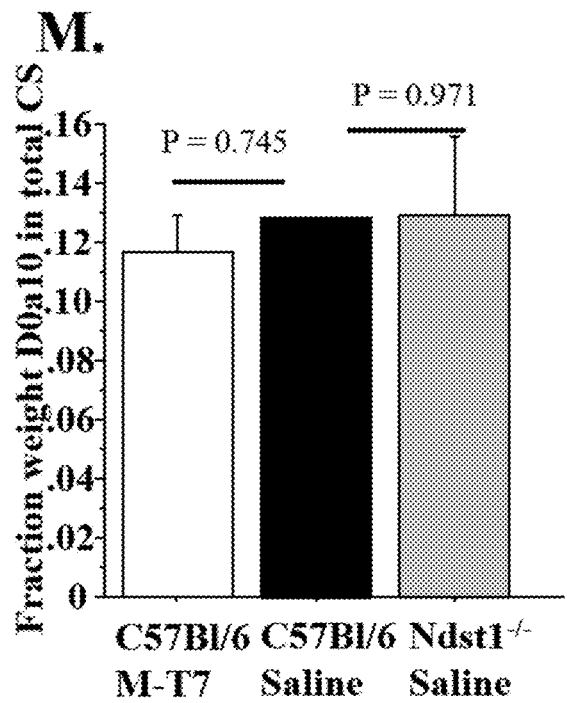
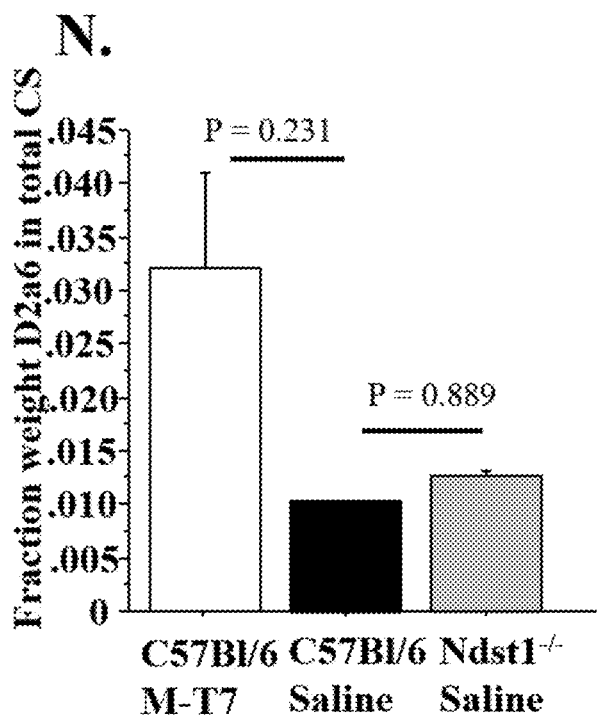
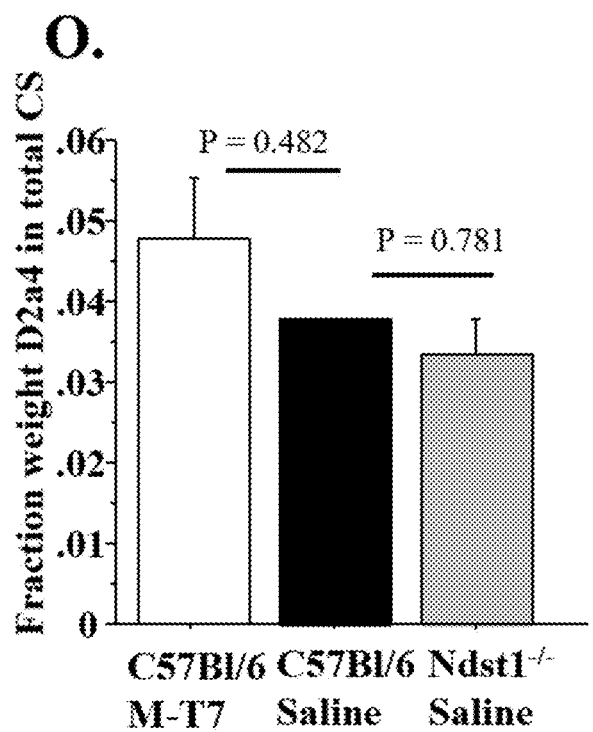
Multiple regression analysis of CS disaccharides (weight):
R = 0.851
$R^2$ = 0.725
Adj $R^2$ = 0.174
FIG. 13M, FIG. 13N, FIG. 13O, FIG. 13P

SEQUENCE LISTING

<160> NUMBER OF SEQ ID NOS: 4

<210> SEQ ID NO 1
<211> LENGTH: 263
<212> TYPE: PRT
<213> ORGANISM: Artificial Sequence
<220> FEATURE:
<223> OTHER INFORMATION: Synthetic Polypeptide

<400> SEQUENCE: 1

Met Asp Gly Arg Leu Val Phe Leu Leu Ala Ser Leu Ala Ile Val Ser
1               5                   10                  15

Asp Ala Val Arg Leu Thr Ser Tyr Asp Leu Asn Thr Phe Val Thr Trp
            20                  25                  30

Gln Asp Asp Gly Tyr Thr Tyr Asn Val Ser Ile Lys Pro Tyr Thr Thr
        35                  40                  45

Ala Thr Trp Ile Asn Val Cys Glu Trp Ala Ser Ser Ser Cys Asn Val
50                  55                  60

Ser Leu Ala Leu Gln Tyr Asp Leu Asp Val Val Ser Trp Ala Arg Leu
65                  70                  75                  80

Thr Arg Val Gly Lys Tyr Thr Glu Tyr Ser Leu Glu Pro Thr Cys Ala
                85                  90                  95

Val Ala Arg Phe Ser Pro Pro Glu Val Gln Leu Val Arg Thr Gly Thr
            100                 105                 110

Ser Val Glu Val Leu Val Arg His Pro Val Val Tyr Leu Arg Gly Gln
        115                 120                 125

Glu Val Ser Val Tyr Gly His Ser Phe Cys Asp Tyr Asp Phe Gly Tyr
    130                 135                 140

Lys Thr Ile Phe Leu Phe Ser Lys Asn Lys Arg Ala Glu Tyr Val Val
145                 150                 155                 160

Pro Gly Arg Tyr Cys Asp Asn Val Glu Cys Arg Phe Ser Ile Asp Ser
                165                 170                 175

Gln Glu Ser Val Cys Ala Thr Ala Val Leu Thr Tyr Asp Gly Ser Tyr
            180                 185                 190

Arg Ser Glu Ala Gly Val Glu Val Cys Val Pro Glu Leu Ala Lys Arg
        195                 200                 205

Glu Val Ser Pro Tyr Ile Val Lys Lys Ser Ser Asp Leu Glu Tyr Val
    210                 215                 220

Lys Arg Ala Ile His Asn Glu Tyr Arg Leu Asp Thr Ser Ser Glu Gly
225                 230                 235                 240

Arg Arg Leu Glu Glu Leu Tyr Leu Thr Val Ala Ser Met Phe Glu Arg
                245                 250                 255

Leu Val Glu Asp Val Phe Glu
            260

<210> SEQ ID NO 2
<211> LENGTH: 263
<212> TYPE: PRT
<213> ORGANISM: Artificial Sequence
<220> FEATURE:
<223> OTHER INFORMATION: Synthetic Polypeptide

<400> SEQUENCE: 2

Met Asp Gly Arg Leu Val Phe Leu Leu Ala Ser Leu Ala Ile Val Ser
1               5                   10                  15

Asp Ala Val Arg Leu Thr Ser Tyr Asp Leu Asn Thr Phe Val Thr Trp
            20                  25                  30

Gln Asp Asp Gly Tyr Thr Tyr Asn Val Ser Ile Lys Pro Tyr Thr Thr
        35                  40                  45

Ala Thr Trp Ile Asn Val Cys Glu Trp Ala Ser Ser Ser Cys Asn Val
50                  55                  60

Ser Leu Ala Leu Gln Tyr Asp Leu Asp Val Val Ser Trp Ala Arg Leu
65                  70                  75                  80

Thr Arg Val Gly Lys Tyr Thr Glu Tyr Ser Leu Glu Pro Thr Cys Ala
            85                  90                  95

Val Ala Arg Phe Ser Pro Pro Glu Val Gln Leu Val Arg Thr Gly Thr
        100                 105                 110

Ser Val Glu Val Leu Val Arg His Pro Val Val Tyr Leu Arg Gly Gln
    115                 120                 125

Glu Val Ser Val Tyr Gly His Ser Phe Cys Asp Tyr Asp Phe Gly Tyr
130                 135                 140

Lys Thr Ile Phe Leu Phe Ser Lys Asn Lys Arg Ala Glu Tyr Val Val
145                 150                 155                 160

Pro Gly Arg Tyr Cys Asp Asn Val Glu Cys Glu Phe Ser Ile Asp Ser
                165                 170                 175

Gln Glu Ser Val Cys Ala Thr Ala Val Leu Thr Tyr Asp Gly Ser Tyr
            180                 185                 190

Arg Ser Glu Ala Gly Val Glu Val Cys Val Pro Glu Leu Ala Lys Arg
        195                 200                 205

Glu Val Ser Pro Tyr Ile Val Lys Lys Ser Ser Asp Leu Glu Tyr Val
    210                 215                 220

Lys Arg Ala Ile His Asn Glu Tyr Arg Leu Asp Thr Ser Ser Glu Gly
225                 230                 235                 240

Arg Arg Leu Glu Glu Leu Tyr Leu Thr Val Ala Ser Met Phe Glu Arg
                245                 250                 255

Leu Val Glu Asp Val Phe Glu
            260

<210> SEQ ID NO 3
<211> LENGTH: 263
<212> TYPE: PRT
<213> ORGANISM: Artificial Sequence
<220> FEATURE:
<223> OTHER INFORMATION: Synthetic Polypeptide

<400> SEQUENCE: 3

Met Asp Gly Arg Leu Val Phe Leu Leu Ala Ser Leu Ala Ile Val Ser
1               5                   10                  15

Asp Ala Val Arg Leu Thr Ser Tyr Asp Leu Asn Thr Phe Val Thr Trp
            20                  25                  30

Gln Asp Asp Gly Tyr Thr Tyr Asn Val Ser Ile Lys Pro Tyr Thr Thr
        35                  40                  45

Ala Thr Trp Ile Asn Val Cys Glu Trp Ala Ser Ser Ser Cys Asn Val
    50                  55                  60

Ser Leu Ala Leu Gln Tyr Asp Leu Asp Val Val Ser Trp Ala Arg Leu
65                  70                  75                  80

Thr Arg Val Gly Lys Tyr Thr Glu Tyr Ser Leu Glu Pro Thr Cys Ala
            85                  90                  95

Val Ala Arg Phe Ser Pro Pro Glu Val Gln Leu Val Arg Thr Gly Thr
        100                 105                 110

Ser Val Glu Val Leu Val Arg His Pro Val Val Tyr Leu Arg Gly Gln
    115                 120                 125

Glu Val Ser Val Tyr Gly His Ser Phe Cys Asp Tyr Asp Phe Gly Tyr
130                 135                 140

Lys Thr Ile Phe Leu Phe Ser Lys Asn Lys Arg Ala Glu Tyr Val Val
145                 150                 155                 160

Pro Gly Arg Tyr Cys Asp Asn Val Glu Cys Arg Phe Ser Ile Asp Ser
                165                 170                 175

Gln Glu Ser Val Cys Ala Thr Ala Val Leu Thr Tyr Asp Gly Ser Tyr
            180                 185                 190

Arg Ser Glu Ala Gly Val Glu Val Cys Val Pro Glu Leu Ala Lys Arg
        195                 200                 205

Ile Val Ser Pro Tyr Ile Val Lys Lys Ser Ser Asp Leu Glu Tyr Val
210                 215                 220

Lys Arg Ala Ile His Asn Glu Tyr Arg Leu Asp Thr Ser Ser Glu Gly
225                 230                 235                 240

Arg Arg Leu Glu Glu Leu Tyr Leu Thr Val Ala Ser Met Phe Glu Arg
                245                 250                 255

Leu Val Glu Asp Val Phe Glu
            260

<210> SEQ ID NO 4
<211> LENGTH: 263
<212> TYPE: PRT
<213> ORGANISM: Artificial Sequence
<220> FEATURE:
<223> OTHER INFORMATION: Synthetic Polypeptide

<400> SEQUENCE: 4

Met Asp Gly Arg Leu Val Phe Leu Leu Ala Ser Leu Ala Ile Val Ser
1               5                   10                  15

Asp Ala Val Arg Leu Thr Ser Tyr Asp Leu Asn Thr Phe Val Thr Trp
            20                  25                  30

Gln Asp Asp Gly Tyr Thr Tyr Asn Val Ser Ile Lys Pro Tyr Thr Thr
        35                  40                  45

Ala Thr Trp Ile Asn Val Cys Glu Trp Ala Ser Ser Cys Asn Val
    50                  55                  60

Ser Leu Ala Leu Gln Tyr Asp Leu Asp Val Val Ser Trp Ala Arg Leu
65                  70                  75                  80

Thr Arg Val Gly Lys Tyr Thr Glu Tyr Ser Leu Glu Pro Thr Cys Ala
                85                  90                  95

Val Ala Arg Phe Ser Pro Pro Glu Val Gln Leu Val Arg Thr Gly Thr
            100                 105                 110

Ser Val Glu Val Leu Val Arg His Pro Val Val Tyr Leu Arg Gly Gln
        115                 120                 125

Glu Val Ser Val Tyr Gly His Ser Asp Cys Asp Tyr Asp Phe Gly Tyr
    130                 135                 140

Lys Thr Ile Phe Leu Phe Ser Lys Asn Lys Arg Ala Glu Tyr Val Val
145                 150                 155                 160

Pro Gly Arg Tyr Cys Asp Asn Val Glu Cys Arg Phe Ser Ile Asp Ser
                165                 170                 175

Gln Glu Ser Val Cys Ala Thr Ala Val Leu Thr Tyr Asp Gly Ser Tyr
            180                 185                 190

Arg Ser Glu Ala Gly Val Glu Val Cys Val Pro Glu Leu Ala Lys Arg
        195                 200                 205

Glu Val Ser Pro Tyr Ile Val Lys Lys Ser Ser Asp Leu Glu Tyr Val
    210                 215                 220

Lys Arg Ala Ile His Asn Glu Tyr Arg Leu Asp Thr Ser Ser Glu Gly
225                 230                 235                 240

-continued

```
Arg Arg Leu Glu Glu Leu Tyr Leu Thr Val Ala Ser Met Phe Glu Arg
                245                 250                 255
Leu Val Glu Asp Val Phe Glu
            260
```

COMPOSITIONS AND METHODS FOR REDUCING ORGAN REJECTION BY REDUCING HEPARAN SULFATE IN DONOR TRANSPLANTS

CROSS REFERENCE TO RELATED APPLICATIONS

This application is a National Stage Application of PCT/US2016/041372, filed Jul. 7, 2016, entitled "COMPOSITIONS AND METHODS FOR REDUCING ORGAN REJECTION BY REDUCING HEPARAN SULFATE IN DONOR TRANSPLANTS", which claims the benefit under 35 U.S.C. § 119(e) of U.S. provisional application Ser. No. 62/189,548, filed Jul. 7, 2015, entitled "COMPOSITIONS AND METHODS FOR REDUCING ORGAN REJECTION BY REDUCING HEPARAN SULFATE IN DONOR TRANSPLANTS" the entire content of each application which is incorporated herein by reference.

STATEMENT REGARDING FEDERALLY FUNDED RESEARCH

This invention was made with government support under grant numbers HL100202 and GM103390 awarded by National Institutes of Health. The government has certain rights in the invention.

INCORPORATION OF THE SEQUENCE LISTING

The present application contains a sequence listing that was submitted in ASCII format via EFS-Web concurrent with the filing of the application, containing the file name SL_21011_0053P1 which is 9,723 bytes in size, created on Jul. 6, 2016, and is herein incorporated by reference in its entirety.

FIELD OF THE INVENTION

The present disclosure relates to polypeptides derived from the viral anti-inflammatory protein, Myxoma virus virulence factor (M-T7) and more particularly to these polypeptides, comprising point mutations that interfere with chemokine-glycosaminoglycan binding in the donor or transplant and that are useful in, for example, preventing, blocking or reducing rejection of an organ transplant.

BACKGROUND

Innate immune (e.g., inflammatory) cells are activated early after allograft transplant and are active long term, inducing transplant vasculopathy, a leading cause of late transplant loss. Treatment of transplant vasculopathy remains limited and there is a need for treatments to prevent transplant loss. The connective tissue matrix, specifically, glycosaminoglycans (GAGs) in the endothelial glycocalyx, induce inflammatory cell activation through chemokine binding to form a signal array to attract monocytes and T cells. GAGs are thought to direct chemokine mediated cell migration. Current treatments to reduce allograft organ rejection target the host or recipient T cell and B cell mediated immune responses, but do not prevent inflammatory macrophage reactions driving chronic rejection. Alternative strategies to prevent or reduce transplant rejection are needed.

SUMMARY

Disclosed herein, are methods of preventing or blocking or reducing rejection of a transplant (e.g., kidney). The method can comprise contacting an organ (e.g., kidney) with a therapeutically effective amount of a polypeptide, wherein the polypeptide comprises a point mutation and is derived from a Myxoma virus virulence factor (M-T7), fragment or biologically active variant thereof.

Disclosed herein, are methods of reducing or preventing the rejection of a transplant. The method can comprise pretreating the transplant (e.g., organ), such as a kidney, with a therapeutically effective amount of a polypeptide, wherein the polypeptide comprises a point mutation and is derived from a Myxoma virus virulence factor (M-T7), fragment or biologically active variant thereof.

Disclosed herein, are methods of modulating inflammatory monocyte, macrophage and T cell invasion as well as interferon gamma receptor and T cell receptor (TCR) expression in vitro or in vivo. The method comprising contacting a cell in vitro, or contacting an organ prior to the transplantation with a therapeutically effective amount of a polypeptide, wherein the polypeptide comprises a point mutation and is derived from a Myxoma virus virulence factor (M-T7); and modulating glycosaminoglycan and chemokine interactions as well as interferon gamma receptor and TCR expression, as compared to a baseline control.

Disclosed herein, are methods of modulating expression of immune system related markers in vitro or in vivo. The method can comprise contacting a cell in vitro, or contacting an organ prior to transplantation with a polypeptide, wherein the polypeptide comprises a mutation and is derived from a Myxoma virus virulence factor (M-T7), fragment or biologically active variant thereof.

Disclosed herein is a kidney treated with a polypeptide, wherein the polypeptide comprises a point mutation and is derived from a Myxoma virus virulence factor (M-T7), fragment or biologically active variant thereof.

Disclosed herein, are methods of treating a kidney prior to transplantation. The method can comprise contacting the kidney with a polypeptide, wherein the polypeptide comprises a point mutation and is derived from a Myxoma virus virulence factor (M-T7), fragment or biologically active variant thereof. In some aspects the disclosed methods also include contacting the kidney with proteins and or small inhibitory RNA (siRNA) or anti-sense RNA to reduce Ndst1 (heparan sulfate sulfotransferse enzyme expression).

Disclosed herein, are methods of treating a kidney prior to transplantation. The methods can comprise contacting the kidney with siRNA or anti-sense RNA, wherein the siRNA or anti-sense RNA targets Ndst1; or glucosamine-6-sulfatase.

BRIEF DESCRIPTION OF THE DRAWINGS

FIG. 4C is a bar graph illustrating overall pathology rejection score, analyzed for 6 pathological parameters by pathologists blinded to donor organ, demonstrating significantly reduced rejection scores in Ndst1$^{-/-}$ compared to WT donors. FIGS. 4D-I are a bar graphs demonstrating significant decreases in individual pathologic parameter scores measured in Ndst1$^{-/-}$ donors compared to WT donors for infiltrate (D), Vasculitis (E), Glomerulitis (F), Peritubular capilaritis (G), Tubulitis (H), and Mesanginal matrix (I). P-value≤0.05 considered significant. Mag 200×. Arrows indicated inflammatory cell infiltrates.

FIGS. 8A-L show flow cytometry analysis of spleen cell isolates from recipient mice after saline treatment of Ndst1$^{-/-}$ engrafted or saline or M-T7 treated WT engrafted mice. Flow analysis detected significantly decreased numbers of Th17 cells when compared to saline treated WT donors (N=56 mice). The percentage cell counts for CD4+ CD3+ (A) and CD4+CD8+ (B) were increased in spleens of mice that received Ndst1$^{-/-}$ donors compared to WT donors, whereas CD3+IFNγ+ cells were non significantly decreased. CD3+Th17+ cells (D) were significantly decreased in mice with Ndst1$^{-/-}$ allografts. M-T7 treatment decreased the percentage cell counts of CD3+CD4+ (E), CD4+CD8+ (F) CD3+IL-17+ (H), CD19+ (I), and CD11c+ (J) cells with no detectable effect on CD3+IFNγ+ (G) compared to saline treated controls in C57BL6 donors. Cell counts were significantly decreased for CD3+ CD*+, CD3+ IL17+, CD19+ and CD11c with M-T7 treatment in WT allografts. Representative flow cytograms demonstrate CD3+IL-17+ cell sorting in spleen cell isolates from saline treated WT engrafted (K) and Ndst1$^{-/-}$ engrafted mice (L). P-value≤0.05 considered significant.

Figure 1:
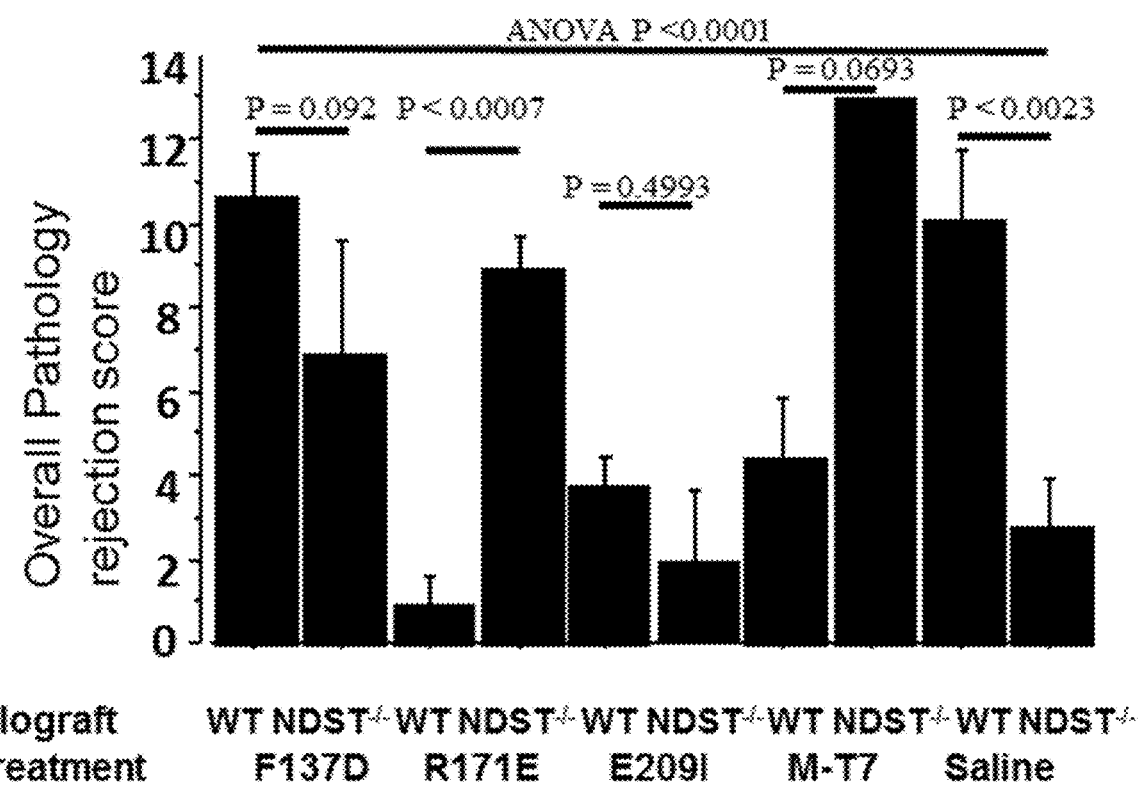
FIG. 1 is a graph illustrating treatment after transplant with M-T7 and the polypeptide comprising the R171E point mutation result in significant reduction in markers for rejection in wild-type (WT) donor allografts.
Figure 2:
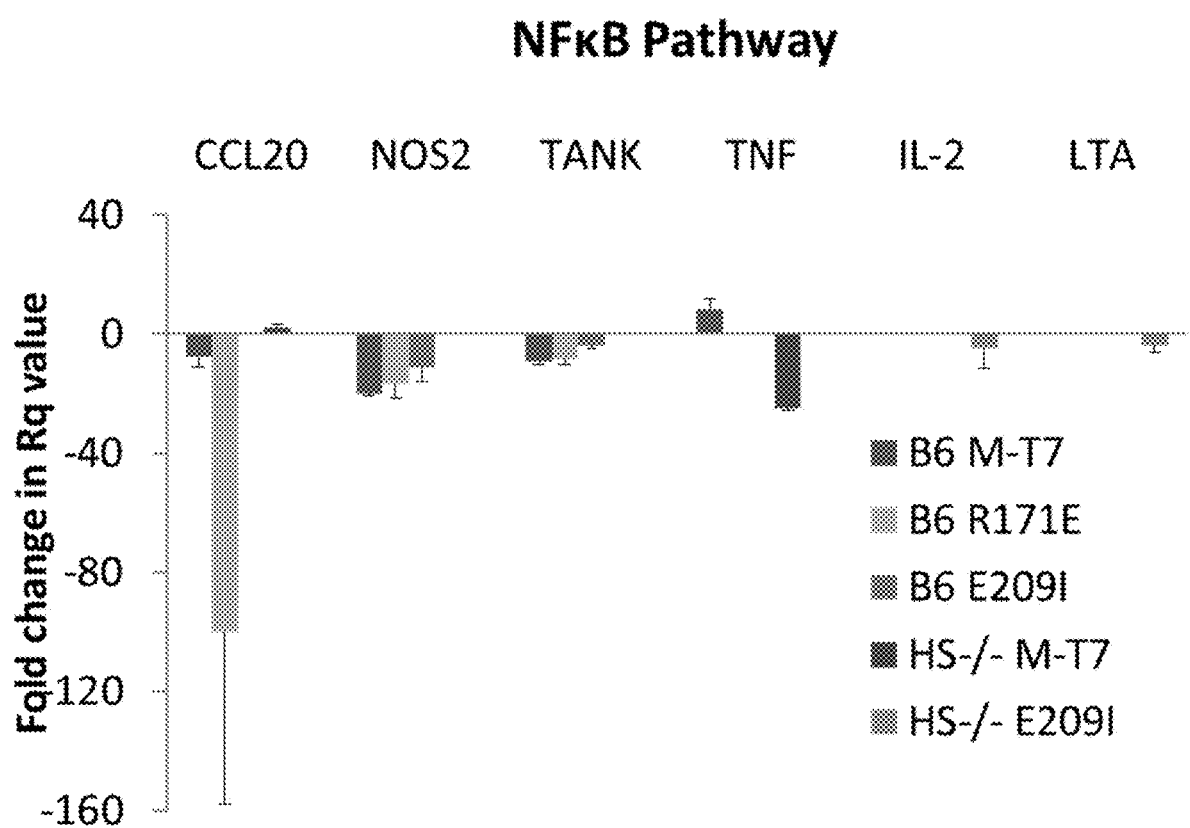
FIG. 2 shows the genes involved in NFκB pathway with significant changes after treatment with M-T7 or polypeptides comprising M-T7 point mutations.
Figure 3:
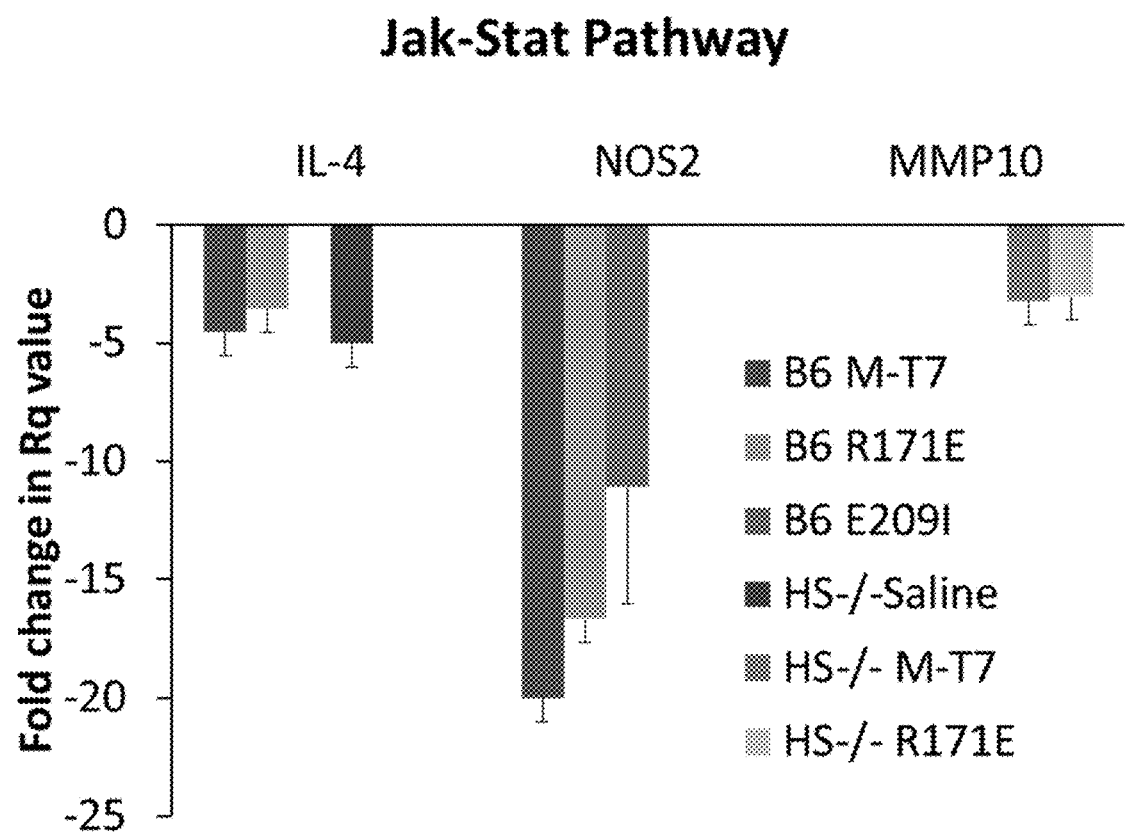
FIG. 3 shows the genes involved in Jak-Stat pathway altered by treatment with M-T7 and the polypeptides comprising M-T7 point mutations.

DETAILED DESCRIPTION

Many modifications and other embodiments of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Although specific terms are employed herein, they are used in a generic and descriptive sense only and not for purposes of limitation.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosures. Further, the dates of publication provided herein can be different from the actual publication dates, which can require independent confirmation.

Definitions

As used in the specification and in the claims, the term “comprising” can include the aspects of “consisting of” and “consisting essentially of.”

As used herein, the singular forms “a,” “an” and “the” include plural referents unless the context clearly dictates otherwise.

The word “or” as used herein means any one member of a particular list and also includes any combination of members of that list.

Ranges can be expressed herein as from “about” or “approximately” one particular value, and/or to “about” or “approximately” another particular value. When such a range is expressed, a further aspect includes from the one particular value and/or to the other particular value. Similarly, when values are expressed as approximations, by use of the antecedent “about,” or “approximately,” it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as “about” that particular value in addition to the value itself. For example, if the value “10” is disclosed, then “about 10” is also disclosed. It is also understood that each unit between two particular units is also disclosed. For example, if 10 and 15 are disclosed, then 11, 12, 13, and 14 are also disclosed.

As used herein, the term “sample” is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term “subject” refers to the target of administration, e.g., a human. Thus the subject of the disclosed methods can be a vertebrate, such as a mammal, a fish, a bird, a reptile, or an amphibian. The term “subject” also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term “patient” refers to a subject afflicted with a disease or disorder. The term “patient” includes human and veterinary subjects. In some aspects of the disclosed methods, the “patient” has been diagnosed with a need for treatment for cancer, such as, for example, prior to the administering step.

As used herein, the terms “peptide” or “polypeptide” refer to a molecule comprising an amino acid sequence of between 2 and 300 amino acids, connected by peptide bonds. Polypeptides according to the present disclosure can contain any of the conventional 20 amino acids or modified version thereof, or can contain non-naturally occurring amino acids incorporated by chemical peptide synthesis or by chemical or enzymatic modification. The polypeptides described herein are myxoma virus interferon-gamma receptor homologs comprising MT-7 point mutations.

The terms "preventing" or "blocking" is used herein to mean preventing in whole or in part or ameliorating or controlling.

The term "reducing" is used herein to mean reducing the severity of symptoms, number of symptoms, reducing the incidence of disease-related symptoms, and/or reducing secondary symptoms associated with transplantation.

The term "modulating" or "modulate" is used herein to mean a change in activity or function or number. The change can be an increase or a decrease, an enhancement or an inhibition of the activity, function or number.

A "therapeutically effective amount" or an "effective amount" refers to the amount of an active composition or polypeptide, or dosage form comprising an active compound, composition or polypeptide which is effective for reducing or blocking or preventing rejection of a transplant. The effective amount can also refer to the amount which is effective to maintain transplant rejection inhibition. One skilled in the art will appreciate that the dosage or amount or concentration of the active compound or polypeptide which is administered to a subject will vary according to individual characteristics including but not limited to weight, age, and other factors including the type and size of cell, organ, organ system or tissue transplanted or about to be transplanted. A therapeutically effective amount can also include an amount that brings about or is expected to bring about a clinically beneficial outcome (e.g., the prolonged survival of a graft) or to have an effect on undesired symptoms.

The term "transplant" is used herein to refer to any cell, organ, organ system or tissue capable of leading to an immune system response in a recipient subject. The process of transplantation involves taking a cell, organ, organ system or tissue, called a "transplant" or "graft" from one subject (e.g., donor) and placing it into a different subject (e.g., recipient). The donor is the subject that provides the transplant and the recipient is the person who receives the transplant. A transplant includes an allograft or a xenograft cell, organ, organ system or tissue.

The term "allograft" is used herein to refer to a graft (e.g., cell, organ, organ system or tissue) collected, received, recovered or otherwise obtained from a member (e.g., donor) of the same species of the recipient.

A "xenograft" is a graft (e.g., cell, organ, organ system or tissue) collected, received, recovered or otherwise obtained from a member (e.g., donor) of a different species than the recipient.

As used herein, the terms "rejection" or "transplant rejection" refer to any immune system responses involved in a transplant rejection, including concomitant physiological result of such immune system responses such as interstitial fibrosis, chronic graft atherosclerosis, inflammatory cell invasion, atherogenic plaque growth, transplant vaculopathy or vasculitis and acute or chronic rejection. Further, rejection can refer to immune system responses associated with autoimmune disorders, and the concomitant physiological result including T cell-dependent infiltration and direct tissue injury; T cell-dependent recruitment and activation of macrophages and other effector cells; and T cell-dependent B cell responses resulting in autoantibody production.

As used herein, the term "contacting" refers bringing a disclosed polypeptide and a cell, a target receptor (e.g. interfering with GAG binding), or other biological entity together in such a manner that the polypeptide can affect the activity of the target, either directly, i.e., by interacting with the target itself; or indirectly, i.e., by interacting with another molecule, co-factor, factor, or protein on which the activity of the target is dependent.

The phrases "cells of the immune system" or "immune system cells" or "immune cells" are used here to include any cells of the immune system that can be assayed, including, but not limited to, B lymphocytes (referred to as B cells), T lymphocytes (referred to as T cells), natural killer (NK) cells, natural killer T cells, regulatory T cells (Treg), Thelper cells (e.g., TH1, TH2 and TH17), lymphokine-activated killer (LAK) cells, monocytes, macrophages, neutrophils, granulocytes, mast cells, platelets, Langerhan's cells, stem cells, dendritic cells, peripheral blood mononuclear cells, tumor-infiltrating (TIL) cells, gene modified immune cells including hybridomas, drug modified immune cells, antigen presenting cells and derivatives, precursors or progenitors of the above cell types.

As used herein, "immune effector cells" refers to cells, and subsets thereof, for example, T regulatory cells (Treg), Th1, Th2, capable of binding an antigen or responding to an antigen presented by an antigen presenting cell, and which mediate an immune system response selective for the antigen. These cells include, but are not limited to, T cells (T lymphocytes) and their subsets e.g. Treg, Th1, Th2, Th17; B cells (B lymphocytes), antigen presenting cells, such as, for example, dendritic cells, monocytes, macrophages; myeloid suppressor cells, NK cells and cytotoxic T lymphocytes (CTLs), for example CTL lines, CTL clones, and CTLs from tumor, inflammatory, or other infiltrates.

As used herein, a "T regulatory cell" or "Treg cell" or "Tr cell" refers to a cell that can inhibit a T cell response. Treg cells express the transcription factor Foxp3, which is not upregulated upon T cell activation and discriminates Tregs from activated effector cells. Tregs are identified by the cell surface markers CD25, CD45RB, CTLA4, and GITR. Treg development is induced by mesenchymal stem cell activity and by other inductive methods including, but not limited to, activation of T cells in the presence of IL-10 and/or TGF-$\beta$. Several Treg subsets have been identified that have the ability to inhibit autoimmune and chronic inflammatory responses and to maintain immune tolerance in tumor-bearing hosts. These subsets include interleukin 10-(IL-10-) secreting T regulatory type 1 (Tr1) cells, transforming growth factor-$\beta$-(TGF-$\beta$-) secreting T helper type 3 (Th3) cells, and "natural" CD4+/CD25+ Tregs (Tm) (Fehervari and Sakaguchi. J. Clin. Invest. 2004, 114:1209-1217; Chen et al. Science, 1994, 265: 1237-1240; Groux et al. Nature. 1997, 389: 737-742).

As used herein, "T cell response" refers to an immunological response involving T cells. The T cells that are "activated" divide to produce additional Th1 or Th2 cells, memory T cells or cytotoxic T cells. The cytotoxic T cells bind to and destroy cells recognized as containing the antigen. The memory T cells are activated by the antigen and thus provide a response to an antigen already encountered. This overall response to the antigen is the T cell response.

The immune system in mammals can be subdivided into two systems: the innate immune system and the adaptive immune system. The innate immune system defends the host from pathogens in a non-specific manner. The adaptive immune system provides a more robust and specific-type of defense against potential pathogens. For instance, the adaptive immune system is capable of inducing antigen and thus has the ability to recognize and remember specific pathogens after a single exposure. In other words, the adaptive immune system can confer immunity and provide an enhanced immune response or attack in a subsequent encounter with the same pathogen.

The phrase "innate immune system response" is used herein to refer to an immune system response that is not generally initiated by prior exposure with a pathogen with an antigen. The skin provides primary protection of the innate immune system by interfering with attachment of any pathogens from the environment. Other mechanisms of the innate immune system that provide protection from pathogens include mucous, which can trap bacteria and other foreign material; gastric acid, which can destroy pathogens that may have been swallowed; antimicrobial substances such as interferon (IFN), which can inhibit viral replication, and complement proteins, which promote bacterial destruction; fever, which can intensify the action of interferons, inhibit microbial growth, and enhance tissue repair; NK cells, which destroy microbes and certain tumor cells, and attack certain virus infected cells; and the inflammatory response, which mobilizes leukocytes such as macrophages and dendritic cells to phagocytose invaders.

The phrase "adaptive immune system response" can be humoral (antibody based) or cellular. An adaptive immune system response is established during the life of a person or animal, and is specific for generating an antigen, and can be enhanced on subsequent exposure with the antigen. T lymphocytes play an important role in the adaptive immune system response. T lymphocytes can detect small concentrations of pathogen-derived peptides presented by MHC molecules on the cell surface. Upon activation, naive CD4 T cells differentiate into one of several cell types, including Th1, Th2 and Th17 cells, each type being characterized by the cytokines it produces. "Th1 cells" are mostly involved in activating macrophages with respect to cellular immunity and the inflammatory response, whereas "Th2 cells" or "helper T cells" are mostly involved in activating B cells to produce antibodies (e.g., humoral immunity). Effector molecules for Th1 cells include, but are not limited to, IFN-γ, GM-CSF, tumor necrosis factor (TNF)-α, CD40 ligand, Fas ligand, IL-3, TNF-β, and IL-2. Effector molecules for Th2 cells include, but are not limited to, IL-4, IL-5, CD40 ligand, IL-3, GS-CSF, IL-10, TGF-β, and eotaxin. Activation of the Th1 type cytokine response can suppress the Th2 type cytokine response, and reciprocally, activation of the Th2 type cytokine response can suppress the Th1 type response.

The term "T cell response" as used herein means an immune system response involving T cells. The T cells that are "stimulated" divide to produce additional Th1 or Th2 cells, memory T cells or cytotoxic T cells. The cytotoxic T cells bind to and destroy cells recognized as having the antigen. The memory T cells are activated by the antigen and thus provide a response to an antigen previously encountered. This overall response to the antigen is the T cell response.

Chemokine-Glycosaminoglycan (GAG) Interactions

Chemokines play a role in cellular immune and inflammatory responses including but not limited to cell signaling, activation and communication. They are categorized into four classes defined by C-terminal cysteine residues (C, CC, CXC, and CX3C) with the CC class being more selective for monocytes and lymphocytes while the CXC class is more selective for neutrophils. Chemokines are proteins (8 to 12 kDa) that draw inflammatory and immune system cells to locations such as arteries and tissues and also lymph nodes in response to damage or invasion by a pathogen. Chemokines then create a gradient along connective tissue and cell layers by binding to polysaccharide chains of glycosaminoglycans (GAGs). GAGs are highly charged and contain sulfate molecules. It is thought that chemokine binding to tissue GAGs leads to an increase in cell specificity to chemokine and receptor interactions (e.g., G-protein-coupled receptors) and thereby directs the movement of immune system (e.g., innate and acquired) cells.

GAGs exist as free molecules or bound to proteins to form proteoglycans comprising disaccharide units that vary from 1 to 25,000. GAGs vary and are defined by disaccharide sequences. These disaccharide sequences can be modified by acetylation and/or N or O sulfation as introduced by enzyme reactions. The interaction of GAGs with cells can modify innate and adaptive immune cell responses.

M-T7 is a Myxomavirus-derived secreted glycoprotein that is pan-species specific with broad spectrum chemokine inhibitory activity. It is also an independent rabbit species-specific interferon gamma receptor (IFNγR) homolog. M-T7 is known to inhibit chemokine/GAG interactions for C, CC and CXC chemokines, with cross-species specific inhibitory activity. For example, M-T7 binds the GAG binding C terminus of C, CC and CXC chemokines from multiple species, thereby disrupting diverse classes of chemokine gradients. Infusions of M-T7 in animals after arterial injury or allograft organ transplant lead to significantly decreased levels of inflammatory cell invasion, arterial plaque growth and ischemia (Liu et al. (2000) J. Clin. Invest. Vol. 105: 1613-21; and Dai (2010) PloS ONE, Vol. 5(5):e10510).

M-T7 is also known to bind to RANTES (regulated upon activated normal T cell expressed and secreted, CCL5), a CC chemokine. Heparan sulfate, a common GAG, competes with M-T7 for binding to RANTES. Tissue and arterial GAGs include heparan sulfate, hyaluronan, chondroitin sulfate, dermatan sulfate and keratin sulfate. Purified M-T7 reduces mononuclear cell invasion and atheroma in rodent models of angioplasty injury as well as aortic and renal transplants, improving renal allograft survival at 5 months (Liu et al. (2000) J. Clin. Invest. 105:1613-1621; and Bedard et al. (2003) Transplantation. 76(1): 249-252).

Other studies have demonstrated that M-T7 treatment alone without adjuvant immunosuppression improved renal allograft transplant survival and reduced aortic allograft intimal plaque growth. For instance, M-T7 mediated anti-atheroma activity was blunted in GAG deficient mouse donor aortic transplants, but not in CC chemokine receptor deficient transplants, supporting that notion that M-T7 interference in chemokine/GAG interactions serve as the basis of the atheroma-inhibitory activity (Dai et al. (2010) PLoS One 5:e10510).

Transplant Vasculopathy

Transplant vasculopathy (TV) is accelerated by both acute and chronic rejection pathways and is associated with increased chemokine and chemokine receptor expression, including MCP-1 (CCL2), MIP1α (CCL3), RANTES (CCL5), CCR2, and CXCR3. Traditional immunosuppressive drug regimens target T and B cell activation and acute rejection, but do not prevent inflammatory macrophage reactions driving chronic rejection. Medical treatments with cholesterol lowering agents (e.g., statins), proliferation inhibitors (e.g., sirolimus), and immunosuppression reduce, but do not eliminate, TV and graft loss.

In acute TV, the locally induced chemokines bind to both the cell surface and the nearby extracellular GAGs, allowing chemoattractant gradients to form and directionally attract inflammatory cells. The inhibition of the chemokine/GAG interaction is now considered an important component for controlling hyperactive inflammatory cells and can serve as a novel therapeutic strategy.

Viral chemokine modulating proteins (CMPs) can serve to provide new and extensive sources for therapeutics. Large DNA viruses have evolved pan-specific CMPs that inhibit a broad range of chemokines, rather than ligand-specific chemokine antagonists, that can blunt innate inflammation after tissue damage (as in allograft transplants).

Previous studies have demonstrated that M-T7 point mutations, R171E and E209I, lose their inhibitory activity for plaque growth in hyperlipidemic ApoE$^{-/-}$ mice after angioplasty injury and that R171E, exacerbated plaque growth and inflammation. M-T7 point mutation, F137D, however, retained some inhibitory activity for plaque growth (Bartee et al. (2014) Cytokine 65:79-87). The present disclosure describes the effects of M-T7 point mutations and M-T7 on early changes in donor solid organ renal allografts from WT C57Bl/6 in HS-GAG deficient organs and methods of reducing or preventing the likelihood of graft rejection in a patient. In solid organ renal transplant, R171E and E209I reduced transplant rejection while F137D lost inhibitory activity for transplants.

Polypeptides:

Point mutations of M-T7 (i.e., M-T7 homologs) were previously described (Bartee et al., (2014) Cytokine 65:79-87). MT-7 comprises several putative glycosylation sites and expression in cells can permit core glycosylation thereby increasing the likelihood that bioactive M-T7 will be expressed. Recombinant His tagged M-T7 (M-T7-His$_{6x}$) has previously been generated in a baculovirus mediated insect cell system. Point mutations of M-T7-His$_{6x}$ can be made in select regions for the purpose of disrupting predicted interaction sites for M-T7 with chemokines and disrupting the overall stability of the M-T7 molecular structure.

Disclosed herein are the following sequences: M-T7 (SEQ ID NO: 1); point mutations: R171E (SEQ ID NO: 2), E209I (SEQ ID NO: 3) and F137D (SEQ ID NO: 4). The sequences are shown in the Table below.

NO: 2), E209I (SEQ ID NO: 3) and F137D (SEQ ID NO: 4). R171E is located near a putative glycosylation site, which may represent a favorable GAG binding environment. E209I is located in a long linker region near the C-terminus that is predicted to form a helix-loop-helix structure. From the M-T7 model based on the crystal structure of the ectromelia virus IFNgamma (IFNγ) binding protein, the E209I residue may lie in a region of the protein that is disordered, flexible, or changes conformation upon protein binding. Based on the binding data, mutation of this residue results in the loss of binding to rabbit IFNγ or RANTES. From western blot analysis, the mobility of E209I is altered compared to wild type, suggesting mutation of this residue is affecting the overall conformation of the protein. Both the F137D and R171E mutations are adjacent to pairs of cysteine residues which, in homologous proteins, form structurally important disulfide bonds. Disulfide bond pairing may be important for the proper folding of the IFNγ receptor ectodomain.

Polypeptides can have (consist of) or include (comprise) a sequence as specifically set out herein (e.g., SEQ ID NO: 2) or they can be biologically active fragments or analogs of any of these reference sequences. A fragment is different from a reference sequence by containing fewer contiguous amino acid residues (one or more amino acids from the N- or C-terminal are deleted). An analog is different from a reference sequence by including at least one additional amino acid residue or at least one amino acid substitution. Any additional amino acid residue(s) can be added to the N-terminal, C-terminal, to a position between the termini of a reference polypeptide, or at any combination of these

TABLE 1

Sequences.

| SEQ ID NO: | | Sequence | | |
|---|---|---|---|---|
| 1 | 1 | MDGRLVFLLA | SLAIVSDAVR | LTSYDLNTFV TWQDDGYTYN |
|   | 41 | VSIKPYTTAT | WINVCEWASS | SCNVSLALQY DLDVVSWARL |
|   | 81 | TRVGKYTEYS | LEPTCAVARF | SPPEVQLVRT GTSVEVLVRH |
|   | 121 | PVVYLRGQEV | SVYGHSFCDY | DFGYKTIFLF SKNKRAEYVV |
|   | 161 | PGRYCDNVEC | RFSIDSQESV | CATAVLTYDG SYRSEAGVEV |
|   | 201 | CVPELAKREV | SPYIVKKSSD | LEYVKRAIHN EYRLDTSSEG |
|   | 241 | RRLEELYLTV | ASMFERLVED | VFE |
| 2 | 1 | MDGRLVFLLA | SLAIVSDAVR | LTSYDLNTFV TWQDDGYTYN |
|   | 41 | VSIKPYTTAT | WINVCEWASS | SCNVSLALQY DLDVVSWARL |
|   | 81 | TRVGKYTEYS | LEPTCAVARF | SPPEVQLVRT GTSVEVLVRH |
|   | 121 | PVVYLRGQEV | SVYGHSFCDY | DFGYKTIFLF SKNKRAEYVV |
|   | 161 | PGRYCDNVEC | EFSIDSQESV | CATAVLTYDG SYRSEAGVEV |
|   | 201 | CVPELAKREV | SPYIVKKSSD | LEYVKRAIHN EYRLDTSSEG |
|   | 241 | RRLEELYLTV | ASMFERLVED | VFE |
| 3 | 1 | MDGRLVFLLA | SLAIVSDAVR | LTSYDLNTFV TWQDDGYTYN |
|   | 41 | VSIKPYTTAT | WINVCEWASS | SCNVSLALQY DLDVVSWARL |
|   | 81 | TRVGKYTEYS | LEPTCAVARF | SPPEVQLVRT GTSVEVLVRH |
|   | 121 | PVVYLRGQEV | SVYGHSFCDY | DFGYKTIFLF SKNKRAEYVV |
|   | 161 | PGRYCDNVEC | RFSIDSQESV | CATAVLTYDG SYRSEAGVEV |
|   | 201 | CVPELAKRIV | SPYIVKKSSD | LEYVKRAIHN EYRLDTSSEG |
|   | 241 | RRLEELYLTV | ASMFERLVED | VFE |
| 4 | 1 | MDGRLVFLLA | SLAIVSDAVR | LTSYDLNTFV TWQDDGYTYN |
|   | 41 | VSIKPYTTAT | WINVCEWASS | SCNVSLALQY DLDVVSWARL |
|   | 81 | TRVGKYTEYS | LEPTCAVARF | SPPEVQLVRT GTSVEVLVRH |
|   | 121 | PVVYLRGQEV | SVYGHSDCDY | DFGYKTIFLF SKNKRAEYVV |
|   | 161 | PGRYCDNVEC | RFSIDSQESV | CATAVLTYDG SYRSEAGVEV |
|   | 201 | CVPELAKREV | SPYIVKKSSD | LEYVKRAIHN EYRLDTSSEG |
|   | 241 | RRLEELYLTV | ASMFERLVED | VFE |

In some aspects, disclosed herein are point mutations that can be used in the disclosed methods. For example, disclosed are the following point mutations: R171E (SEQ ID positions. An analog can be shorter than the reference sequence (i.e., it can include a deletion of one or more amino acid residues).

Useful polypeptides can be produced by any methods known in the art, including by synthetic methods and recombinant techniques used routinely to produce proteins from nucleic acids. The prepared polypeptides can be stored in an unpurified or in an isolated or substantially purified form until further use. Chemical synthesis can be achieved by solid phase synthesis, and recombinant techniques can include expression form vector constructs in a cell (e.g., a prokaryotic or eukaryotic cell). Codons that encode specific amino acid residues are well known in the art.

Compositions:

The present disclosure also features compositions that contain a therapeutically effective amount of a polypeptide as described herein. The compositions can be pharmaceutical compositions and be used in methods of treating subjects and/or transplants as described further below. The compositions can be formulated for administration by any of a variety of routes of administration, and can include one or more physiologically acceptable excipients, which can vary depending on the route of administration. The term "excipient" is used herein to mean any compound or substance, including those that may also be referred to as "carriers" or "diluents." Preparing pharmaceutical and physiologically acceptable compositions is generally considered to be routine in the art, and one of ordinary skill in the art can consult numerous authorities for guidance. In some aspects, the compositions and compositions suitable for the methods disclosed herein can comprise proteins or inhibitors of Ndst1. For example, disclosed are siRNAs and/or anti-sense RNA for Ndst1 or sulfatase enzymes. Sulfatase enzymes are known to one of ordinary skill in the art. In an aspect, the sulfatase enzyme is glucosamine-6-sulfatase. Any of the compositions described herein can be administered alone or in any combination thereof, including simultaneously or sequentially.

Formulation/Dosage/Administration:

Compositions comprising the polypeptides described herein for use in the methods disclosed herein can be formulated in a conventional manner using one or more physiologically acceptable carriers or excipients. The compositions can be suspended in a pharmaceutically acceptable carrier (e.g., physiological saline or a buffered saline solution) to facilitate their delivery. Encapsulation of the compositions in a suitable delivery vehicle (e.g., polymeric microparticles or implantable devices) can increase the efficiency of delivery. A composition can be made by combining any of the polypeptides provided herein with a pharmaceutically acceptable carrier. Where the polypeptides are co-administered with another compound, drug and/or pharmaceutical composition to the donor or the transplant, they can be administered in a single formulation or in separate formulations (which can be the same or different) that are administered concurrently or sequentially.

The compositions can be formulated in various ways for parenteral or nonparenteral administration. Oral formulations can take the form of tablets, pills, capsules, or powders, which can be enterically coated or otherwise protected. Sustained release formulations, suspensions, elixirs, aerosols, and the like can also be used.

Pharmaceutically acceptable carriers and excipients can be incorporated (e.g., water, saline, aqueous dextrose, and glycols, oils (including those of petroleum, animal, vegetable or synthetic origin), starch, cellulose, talc, glucose, lactose, sucrose, gelatin, malt, rice, flour, chalk, silica gel, magnesium stearate, sodium stearate, glycerol monosterate, sodium chloride, dried skim milk, glycerol, propylene glycol, ethanol, and the like). One or more of the excipients included can help approximate physiological conditions, such as pH adjusting and buffering agents, tonicity adjusting agents, wetting agents, detergents, and the like.

The compositions can be subjected to conventional pharmaceutical expedients such as sterilization and can contain conventional pharmaceutical additives such as preservatives, stabilizing agents, wetting or emulsifying agents, salts for adjusting osmotic pressure, buffers, and the like. Suitable pharmaceutical carriers and their formulations are well known in the art. Such compositions will, in any event, contain an effective amount of the compositions together with a suitable amount of carrier so as to prepare the proper dosage form for proper administration to the subject (i.e., donor and/or transplant).

The compositions can be sterile; they can be sterilized by conventional sterilization techniques or can be sterile filtered. Aqueous solutions can be packaged for use as is, or lyophilized, the lyophilized preparation, which is encompassed by the present disclosure, being combined with a sterile aqueous carrier prior to administration. In addition, the temperature of the solution can be adjusted when treating the transplant directly. The pH of the pharmaceutical compositions typically will be between 3 and 11 (e.g., between about 5 and 9) or between 6 and 8 (e.g., between about 7 and 8). The pH of the pharmaceutical compositions is between about 7.0 and 7.5. The resulting compositions in solid form can be packaged in multiple single dose units, each containing a fixed amount of the above-mentioned agent or agents, such as in a sealed package of tablets or capsules.

The polypeptides, compositions and/or pharmaceutical compositions described herein can be administered to any part of the donor's body and/or put in contact with any part of the transplant organ or tissue for subsequent delivery to a recipient. A composition can be delivered to, without limitation, the bones, bone marrow, joints, nasal mucosa, blood, lungs, intestines, muscle tissues, skin, internal or external surfaces of organs, or the peritoneal cavity of a donor. In terms of routes of delivery, a polypeptide, composition and/or pharmaceutical composition can be administered by intravenous, intraperitoneal, intramuscular, subcutaneous, intrarectal, intravaginal, intrathecal, intratracheal, intradermal, or transdermal injection, by oral or nasal administration, or by gradual perfusion over time. In a further example, an aerosol preparation of a composition can be given to a recipient by inhalation. Alternatively, a polypeptide, composition and/or pharmaceutical composition can be provided to the transplant through perfusion or an aqueous solution comprising the polypeptide. In an aspect, an organ or tissue for transplant can be contacted, such as, but not limited to, by bathing, immersion, perfusion, spraying, or dipping, the organ or tissue with a composition comprising a polypeptide disclosed herein.

The particular dosage of a pharmaceutical composition to be administered to the donor will depend on a variety of considerations including the nature of the disease and/or condition of the transplant (e.g., the extent of compatibility of a transplant or the severity of an autoimmune disease), the schedule of administration, the route of administration, the nature of the formulation, the age and physical characteristics of the subject (e.g., donor and/or recipient), and other considerations known to those of ordinary skill in the art. Dosages can be established using clinical approaches known in the art. The dosage regimen can be adjusted to provide the optimal therapeutic response. The dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the donor and/or donor organ undergoing therapy/treatment as well the recipient of the transplantation.

The duration of treatment with any composition (i.e., polypeptide) disclosed herein can be any length of time from as short as one day until transplantation. For example, the compositions can be administered daily, weekly, or monthly. In an aspect, the compositions described herein can be administered from about ten days to about thirty days after transplantation.

The frequency of treatment or contact with the polypeptides can vary. The transplant donor or donor organ (or cells, tissues, or organ system) itself can be treated or contacted with a polypeptide as disclosed herein. For example, the donor organ can be contacted with any of the compositions (i.e., polypeptide) disclosed herein, such as, the day before organ harvesting and/or the day of organ harvesting and/or transplantation. The treatment or contact as described above can range from a single daily dose up to, for instance, 10 daily doses prior to removing the organ for transplantation (i.e., organ harvesting) and/or transplantation of the organ (or cells, tissues, or organ system) into the transplant recipient. For example, the treatment can be administered as a bolus injection extending over a few minutes given intravenously or by intraperitoneal injection.

The transplant donor or donor organ itself can be subjected to standard treatments associated with any organ (or cells, tissues, or organ system) prior to transplantation that are provided as part of a pre-transplant routine protocol under the supervision of an attending clinician. The transplant donor organ can also be administered an infusion of glycoasaminoglycan to remove enzymes including heparanase and/or chondroitinase prior to organ harvesting and/or transplantation of the organ (or cells, tissues, or organ system) into the transplant recipient.

In an aspect, the transplant donor organ can be treated or contacted with or exposed to or administered proteins or inhibitors of Ndst1, for example, using siRNA and or anti-sense RNA for Ndst1 or sulfatase enzymes in a therapeutically effective amount. The polypeptides as well as any of the compositions disclosed herein can be administered in a therapeutically effective amount. Administration to a transplant donor or contact with a donor organ can be a single- or multiple dose regimen for the purpose of preventing, blocking and/or reducing the severity of, or ameliorating one or more symptoms of a condition or disorder described herein (e.g., transplant vasculopathy) the likelihood of a rejection of a transplant (e.g., kidney) in a subject (i.e., recipient). The polypeptides and other compositions disclosed above can be administered to the transplant donor prior to the removal of the transplant from the donor. The transplant organ can also be treated independently or after removal from the donor with the polypeptides but prior to transplantation.

The formulations can be prepared by any method well known in the art of pharmacy. The formulation can be prepared to provide for rapid or slow release; immediate, delayed, timed, or sustained release; or a combination thereof. Formulations can be in the form of liquids, solutions, suspensions, emulsions, elixirs, syrups, electuaries, mouthwashes, drops, tablets, granules, powders, lozenges, pastilles, capsules, gels, pastes, ointments, creams, lotions, oils, foams, sprays, mists, or aerosols. Formulations can be provided as a patch, adhesive plaster, bandage, dressing, or in the form of depot or reservoir. Many methods for the preparation of such formulations are known to those skilled in the art.

Preparation of a sterile ointment formulation can include the combination of the polypeptides with a preservative in an appropriate vehicle, such as mineral oil, liquid lanolin, or white petrolatum.

Routes of Administration:

Pharmaceutical compositions as described herein can be formulated for administration by any route of administration, including but not limited to systemic, peripheral, or topical. Illustrative routes of administration include, but are not limited to, oral, such as by ingestion, buccal, sublingual, transdermal including, such as by a patch, plaster, and the like, transmucosal including, such as by a patch, plaster, and the like, intranasal, such as by nasal spray, ocular, such as by eye drops, pulmonary, such as by inhalation or insufflation therapy using, such as via an aerosol through the mouth or nose, rectal, such as by suppository or enema, vaginal, such as by pessary, parenteral, such as by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and by implant of a depot or reservoir, such as intramuscularly. Methods of preparing pharmaceutical formulations are well known in the art. Certain administration methods can include the step of administering the composition one or more times a day to obtain the desired therapeutic effect.

Methods of Treatment:

The methods disclosed herein can be elicited when a patient (e.g., subject or recipient) is in need of a transplant. Accordingly, the methods described herein can include methods for preventing, reducing and/or blocking rejection of a transplant in a subject in need thereof. These methods can be carried out by, for example, administering to a subject (e.g., donor) a therapeutically effective amount of a pharmaceutical composition comprising a polypeptide disclosed herein. For example, the polypeptide can comprise a point mutation as described herein and be derived from M-T7 or a fragment or biologically active variant thereof.

The methods described herein can also include a step of identifying a patient (e.g., subject) in need of a transplant. The methods of the present disclosure can also include a step of identifying, evaluating and/or preparing a subject and/or organ for transplantation.

In an aspect, the transplant is a kidney transplant. Such patients include individuals that are suffering from kidney failure due to hypertension, diabetes mellitus, kidney stones, inherited kidney disease, inflammatory disease of the nephrons and glomeruli and untoward effects of drug treatment for other diseases. The methods can further include a step of identifying an organ that is acceptable for transplant. The organ can be prepared for transplant ex vivo or in vivo. In the case of in vivo preparation, the donor can receive a second type of treatment. In other words, the present compositions can be used in conjunction with existing therapies, including, but not limited to aspirin and heparin.

As mentioned above, the polypeptides described above can be formulated to include a therapeutically effective amount. Accordingly, an aspect of the present disclosure features a method comprising, for example, contacting a transplant (i.e., an organ) such as a kidney with a therapeutically effective amount of a polypeptide comprising a point mutation that is derived from M-T7, a fragment or biologically active variant thereof. The method can further include contacting a transplant (e.g., a kidney) with proteins and/or small inhibitory RNA (siRNA) or anti-sense RNA. The method can comprise contacting a transplant (e.g., a kidney) with proteins and/or small inhibitory RNA (siRNA) or anti-sense RNA can reduce Ndst1 (heparin sulfate sulfotransferase enzyme) expression. In an aspect, the organ is contacted with the polypeptide or any of the treatments (e.g., proteins, siRNA or anti-sense RNA) as described herein one or more days (e.g., 1, 2, 3, 4, 5, 10, 15, 20, 25, 30 or more) before transplantation.

The methods disclosed herein can be carried out to prevent or reduce rejection of a transplant. In an aspect, the method can comprise contacting a transplant (e.g., a kidney) with proteins and/or small inhibitory RNA (siRNA) or anti-sense RNA can reduce Ndst1 (heparin sulfate sulfotransferase enzyme) expression to prevent or reduce rejection of a transplant.

In an aspect, methods disclosed herein can also be directed to treating or contacting a kidney, for example, prior to transplantation. The method can comprise contacting the kidney with siRNA or anti-sense RNA, wherein the siRNA or anti-sense RNA targets Ndst1; or glucosamine-6-sulfatase. Disclosed herein are methods of treating a subject, the method comprising silencing or inhibiting one or more genes or proteins. The terms "silencing" and "inhibiting" are used herein to refer to suppression, full or partial, of expression of a gene or protein. In an aspect, the gene can be Ndst1. The degree of suppression can be to totally abolish production of the encoded gene product or a partial abolition of expression wherein some degree of expression remains. The kidney, for example, can be prepared, prior to transplantation. For example, the kidney can be prepared prior to transplantation by contacting the kidney with the polypeptide or any of the treatments (e.g., proteins, siRNA or anti-sense RNA) as described herein. In an aspect, the method can comprise contacting the kidney with siRNA or anti-sense RNA, wherein the siRNA or anti-sense RNA targets Ndst1; or glucosamine-6-sulfatase to prevent or reduce rejection of a transplant.

In some instances, silencing one or more genes or proteins comprises a technique well known in the art. For example, silencing can be performed by silencing transcription or by silencing translation, both of which result in a suppression of the expression of the gene. Several known techniques can be used for silencing, including but not limited to RNAi, CRISPR, or siRNA. Silencing can also comprise administering a silencing agent.

Without wishing to be bound by any theory, the polypeptides described herein can exert their effects through a variety of mechanisms of action. Thus, the polypeptides can block chemokine/GAG binding, suppress T cells, shift the cytokine profile with a potential reduction in TNF or IL-1 or IL-6 or even lead to a shift in GAG composition. Examples of a shift in cytokine profile include: the down-regulation of epithelial cells, the tightening of the barrier formed by epithelial cells, limiting the influx of immune system cells to a site of inflammation, inhibition of cell accumulation and egress from the blood into tissue spaces, down-regulation of pro-inflammatory cytokines and chemokines, down-regulation of the influx of inflammatory cells (e.g., neutrophils, monocytes/macrophages), and the down-regulation of epithelial cells to prevent them from expressing adhesion molecules that will allow egress of cells out of the blood vessels. In an aspect, the polypeptides disclosed herein can inhibit CC chemokine-mediated cell migration. Cell (e.g., mononuclear) migration can be measured in an in vivo assay (e.g., mouse ascites cell model) as it is known to be involved in immune system responses and pathological conditions. In an aspect, the polypeptides can block or disrupt chemokine-GAG interactions. And, in another aspect, the polypeptide comprises the amino acid sequence of SEQ ID NO: 2 or SEQ ID NO: 3.

In an aspect, the methods described herein can also include methods for reducing, blocking and/or preventing rejection of a transplant comprising pretreating the organ or transplant with a therapeutically effective amount of a polypeptide as described herein. The methods can also include treating or contacting an organ (e.g., a kidney) with a therapeutically effective amount of polypeptide disclosed herein. As described above, the polypeptide can comprise a point mutation and be derived from M-T7 or a fragment or biologically active variant thereof. In an aspect, the transplant is a kidney. In another aspect, the polypeptide can disrupt chemokine-GAG interactions.

The compositions described herein can be administered to a subject (e.g., a human patient) or transplant (e.g., kidney) in an amount sufficient to reduce, block or prevent the onset of clinical disease and/or symptoms of a condition, its complications and consequences (e.g., transplant vasculopathy). In therapeutic applications, compositions are administered to a subject (e.g., an organ donor) or a transplant, to prevent or reduce rejection of the transplant.

In aspect, the method features modulating T cell receptor (TCR) expression in vitro or in vivo. The methods disclosed herein also include modulating inflammatory monocyte, macrophage and T cell invasion in vitro or in vivo. The methods described herein further can include modulating interferon gamma receptor expression in vitro or in vivo. The methods can be carried out by contacting a cell, for example in vitro or contacting an organ prior to transplantation with a therapeutically effective amount of a polypeptide disclosed herein and modulating the TCR expression (or interferon gamma receptor expression; or modulating the inflammatory monocyte, macrophage and T cell invasion) as compared to a baseline control. The methods disclosed herein can also modulate glycosaminoglycan and chemokine interactions as compared to a baseline control. TCR expression (or interferon gamma receptor expression; or modulating the inflammatory monocyte, macrophage and T cell invasion) or modulate glycosaminoglycan and chemokine interactions can occur or take place in vitro, prior to transplantation or in vivo, after transplantation or in vitro and in vivo.

Any method known to one of ordinary skill in the art can be used to determine if a particular response is induced. Clinical methods that can assess the degree of a particular disease state can be used to determine if a response is induced. For example, in a transplant patient, clinical methods can include blood tests to assess organ function, ultrasound analysis of the size of the transplanted organ and blood flow, x-rays, biopsies, electrocardiograms and echocardiograms to monitor heart function, pulmonary function tests, molecular analysis such as AlloMap™ to monitor the activity of specific genes in white blood cells to determine the risk of acute cellular rejection. The particular methods used to evaluate a response will depend upon the nature of the patient's disorder, the patient's age, and sex, other drugs being administered, and the judgment of the attending clinician.

In some embodiments, the methods to determine if a particular response is induced can include comparing a patient's sample with standard reference levels for the particular marker or assay. Standard reference levels typically represent the levels derived from a large population of individuals. The reference population can include individuals of similar age, body size; ethnic background or general health as the individual in question. Thus, for example, marker levels in a patient's sample can be compared to values derived from: 1) individuals who have not received a graft; 2) individuals who have successfully received a graft, i.e., individuals in which the graft has not been rejected; and/or 3) individuals who have rejected a graft. Any population size can be used to determine the reference levels. For example, a population of between 2 and 250, e.g., 2, 3, 4, 5, 10, 15, 20, 25, 30, 40, 50, 100, 150, 200, 250 or more individuals can be used to determine the average reference levels, with greater accuracy in the measurement coming from larger sample populations.

In an aspect, the polypeptide as disclosed herein can reduce TCR expression as compared to a reference level. The TCR can be a CD3+ cell surface marker. In another aspect, the polypeptide comprises the amino acid sequence set forth in SEQ ID NO: 2 or SEQ ID NO: 3.

Other methods of the present disclosure feature modulating expression of immune system related markers in vitro or in vivo. The method can comprise contacting a cell in vitro or contacting an organ prior to transplantation with one of the polypeptides described herein.

The present disclosure also features a kidney treated with a polypeptide as described herein. In an aspect, the polypeptide can have the amino acid sequence of SEQ ID NO: 2 or SEQ ID NO: 3.

In an aspect, a method comprising treating or contacting a kidney prior to transplantation with a polypeptide as described herein is disclosed. The polypeptide can have the amino acid sequence of SEQ ID NO: 2 or SEQ ID NO: 3. Further, the polypeptide can reduce rejection of the transplanted kidney and/or T cell receptor expression in vitro or in vivo as compared to a reference level. In an aspect, the polypeptide can reduce T cell receptor expression in the kidney prior to transplantation or after transplantation as compared to a reference level.

The compositions and methods disclosed herein can be used in any situation in which a subject (e.g., recipient) is to receive a graft of biological material other than an autograft. The organ (or cells, tissues, or organ system) to be transplanted can be, for example a kidney, lung, heart, liver, pancreas, skin and/or bone marrow. In an aspect, the cells to be transplanted can be, for example, stem cells.

The compositions can include one or more additional therapeutic agents including but not limited to any of the polypeptides described herein or other GAGs including, for example, heparan sulfate, GAG degrading enzyme (e.g., hyaluronic acid, dermatan sulfate, chondroitin sulfate, heparin and keratan sulfate) or aspirin. The particular combination of therapeutic agents can vary according to many factors, for example, the particular kind of graft, the immunocompatibility between the recipient and the donor, and the health of the recipient. Regardless of the specific combination, the compositions can be administered directly to a subject and/or transplant.

While the present methods contemplate the treatment and prevention of graft rejection in human subjects, veterinary uses are also within the scope of the present disclosure. Accordingly, the methods described herein can be applied to treat humans, non-human primates, domestic animals (e.g., dogs, cats, pigs, horses, cows, sheep, and goats) and avian subjects (e.g., chickens).

Kits:

The polypeptides described herein can be packaged in suitable containers labeled, for example, for use as a therapy to reduce, block and/or prevent graft rejection. The containers can include one or more compounds, e.g., heparan sulfate, hyaluronic acid, dermatan sulfate, chondroitin sulfate, heparin, keratan sulfate or aspirin, or a combination of one or more polypeptides, and one or more of a suitable stabilizer, carrier molecule, flavoring, and/or the like, as appropriate for the intended use. Accordingly, packaged products (e.g., sterile containers containing one or more of the polypeptides described herein and packaged for storage, shipment, or sale at concentrated or ready-to-use concentrations) and kits, including at least one polypeptide of described herein and instructions for use, are also within the scope of the disclosure. A product can include a container (e.g., a vial, jar, bottle, bag, or the like) containing one or more polypeptides of the disclosure. In addition, a kit can include, for example, packaging materials, instructions for use, syringes, buffers or other control reagents for treating a transplant (e.g., a kidney) and/or a subject (e.g., a donor). The product can also include a legend (e.g., a printed label or insert or other medium describing the product's use (e.g., an audio- or videotape)). The legend can be associated with the container (e.g., affixed to the container) and can describe the manner in which the polypeptide therein should be administered (e.g., the frequency and route of administration), indications therefor, and other uses. The polypeptides can be ready for administration (e.g., present in dose-appropriate units), and can include a pharmaceutically acceptable adjuvant, carrier or other diluent and/or an additional therapeutic agent. Alternatively, the polypeptides can be provided in a concentrated form with a diluent and instructions for dilution.

The polypeptides of the present disclosure can also include fragments or metabolites of such polypeptides that exhibit the activity of the full-length polypeptides. The present disclosure comprises polynucleotides that encode such polypeptides, fragments and metabolites as disclosed herein. Other forms of disclosed polypeptides may comprise homologous polypeptides or fragments, or cyclized fragments.

The details of one or more aspects of the present disclosure are set forth in the accompanying drawings, description and Examples. Other features, objects, and advantages of the present disclosure will be apparent from the description, drawings, Examples and from the claims.

EXAMPLES

Example 1: Blockade of Chemokine/Glycosaminoglycan (GAG) Binding in the Renal Donor Organ Significantly Reduces Transplant Rejection and Vascular Inflammation Early chemokine/GAG interactions after renal allograft transplantation and inflammatory cell responses were investigated. Ndst1 or Heparin sulfate (HS)-GAG sulfotransferase deficient knock-out organ donor mice (Ndst1$^{-/-}$ (GAO were used. A viral chemokine modulating protein (CMP) that blocks chemokine/GAG interactions and M-T7 which blocks C, CC and CXC chemokine/GAG interactions was also used.

A C-terminal His-tagged M-T7 was cloned into pcDNA3.1 by PCR. This construct was then subcloned into a pFastBacDual (Invitrogen, Carlsbad, Calif.) expression vector containing an eGFP (Enhanced Green Fluorescent Protein) reporter driven by the p10 promoter. Subsequent MT-7 point mutations were generated by mutagenic PCR of the M-T7 pFastBacDual construct. These constructs were transformed into DH10Bac (Invitrogen, Carlsbad, Calif.) cells to generate bacmids. Colonies were screened using blue/white colony screening by spreading 100 µl of 100 mM IPTG (isopropylbeta-D-thiogalactopyranoside) and 40 µl of 20 mg/mL X-gal (5-bromo-4-chloro-3-indolyl-b-D-galactopyranoside) onto selection plates (LB with 50 µg/mL kanamycin, 10 µg/mL tetracycline, 7 µg/mL gentamicin). Bacmids were purified using QIAprep Spin Miniprep Kit (Qiagen), eluting in 100 µl of elution buffer heated to 50° C. to facilitate elution off of the spin column. Incorporation of M-T7 into the bacmid was verified by PCR.

Sf21 cells were seeded onto 6 well tissue culture plates in 1× Grace's Insect Media (Invitrogen) at $1\times10^6$ cells/mL for a total of 2 mLs (one hour before transfection) to allow the cells to adhere. DNA (1-2 µg) was pre-incubated in 100 µl of 1× Grace's Insect Media in one tube and 6 µl of Cellfectin II (Invitrogen, Carlsbad, Calif.) reagent with 100 µl of 1× Grace's Insect Media in another tube and incubated in the hood for 15 min before the DNA and Cellfectin II containing reagents were mixed together for 30 min at room temperature. The transfection reaction mixture was brought up to a final volume of 1 mL with 1× Grace's Insect Media. Before adding the mixture to cells, cells were washed in 1× Grace's Insect Media and then aspirated. The transfected cells were incubated at 27° C. for 5 h before replacement of the transfection reagent with Sf-900 II SFM. Baculovirus was harvested from the media once eGFP positive cells were seen and used to amplify more baculovirus. Viral titer was measured using a foci forming assay.

M-T7 protein and constructs (i.e., polypeptides comprising the MT-7 point mutations) were expressed in suspension cultures of High Five insect cells. Cells seeded at 1×106 cells/mL were infected with baculovirus containing the M-T7 gene construct at an MOI of 1 and grown in culture for 72 h. To purify protein from High Five infected cells, cells were first lysed in 50 mM Tris+250 mM NaCl+10 mM imidazole by douncing. Lysate was cleared by centrifugation at 20,000×g and the supernatant was passed through a 0.22 micron filter. Supernatant was then loaded onto a 100 kDa cutoff filter and the flow through was used for purification, Amicon Ultra (Millipore).

M-T7 was added to equilibrated Co-NTA (Nickel-Nitrilotriacetic acid) slurry (Sigma) and allowed to mix overnight at 4° C. The slurry was added to a column the next day, and allowed to flow through by gravity. The samples were then washed in 50 mM Tris+250 mM NaCl+20 mM imidazole pH 8.0, and eluted with 50 mM Tris+250 mM NaCl+250 mM imidazole pH 8.0 in eight 1 mL elution fractions. The elution fractions containing M-T7 are combined and further concentrated and buffer exchanged in 0.9% NaCl with a 10 kDa molecular weight cutoff Amicon Ultra centrifugal filters (Millipore). Protein purity was verified by running the samples on a SDS-PAGE (sodium dodecyl sulfate-polyacrylamide gel electrophoresis) and stained with Coomassie/Silver and western blot analysis. Samples were kept under sterile conditions after filtration through a 0.22 ml filter and aliquoted. The measured circulating half-life for M-T7 in a rat PK study was 11.5 h, using 1.25 mg/kg i.v. (Viron Therapeutics, Inc., Personal communication). The tissue half-life has not been measured.

Renal transplants from C57BL/6 wild type mice or NDST1$^{-/-}$ mice were transplanted into Balb/C mice and treated with either saline, M-T7, or one of three different M-T7 point mutations (100 ng/gm; R171E, F137D or E209I) with differing inhibitory actions for chemokine/GAG interactions for 10 days. Table 2 shows the treatment regimen.

TABLE 2

Treatment regimen.

| Treatment | Dose/mouse | Number mice transplanted | (Donor →Recipient) | Follow up (days) |
|---|---|---|---|---|
| Saline | 500 µl | 11 (C57BL/6→ Balb/C) | 9 (C57BL/6→ NDST1$^{-/-}$) | 10 |
| M-T7 | 100 ng/gm | 7 (C57BL/6→ Balb/C) | 6 C57BL/6→ NDST1$^{-/-}$) | 10 |
| M-T7 (R171E) | 100 ng/gm | 10 (C57BL/6→ Balb/C) | 6 C57BL/6→ NDST1$^{-/-}$) | 10 |
| M-T7 (F137D) | 100 ng/gm | 10 (C57BL/6→ Balb/C) | 6 C57BL/6→ NDST1$^{-/-}$) | 10 |
| M-T7 (E209I) | 100 ng/gm | 10 (C57BL/6→ Balb/C) | 6 C57BL/6→ NDST1$^{-/-}$) | 10 |
| Total no. of mice | | 48 | 33 | |

The results show HS-GAG deficiency in the donor renal allograft implant reduces early rejection and inflammation. Interruption of the chemokine/GAG interaction by the virus-derived M-T7 protein similarly blocks early inflammatory cell invasion and rejection in mouse renal allografts. M-T7 activity is dependent upon HS-GAG expression. These data provide a therapeutic approach for reducing transplant rejection through interference with chemokine/GAG interactions in the donor transplanted kidney. With immunostaining, reduced innate and acquired immune responses were seen.

Example 2: Ndst1 (HS-GAG Modifying Enzyme) Deficiency in Donor Renal Allografts Significantly Reduces Histopathological Markers for Acute Renal Allograft Rejection Unlike proteins, changes in GAG composition are less directly linked to gene expression, but rather reflect altered activity of synthetic and metabolizing enzyme activity at the tissue level. The endothelial glycocalyx is thought to perform a protective, slowly moving barrier along the endothelial cell lumen surface in arteries, but also functioning to integrate cytokines, integrins, chemokines, growth factors and clotting factors which can potentiate inflammation.

The glycocalyx surrounds the renal endothelium and profoundly alters innate and acquired, antibody mediated, immune cell reactions. The effects of heparan sulfate/GAG (HS/GAG) deficiency in the donor organ, as well as blockade of HS/GAG and chemokine interactions on renal transplant rejection were investigated. Donor renal transplants from conditional knock-out N-deacetylase-N-sulfotransferase-1 (Ndstf/fTekCre, Ndst1$^{-/-}$) lacking Ndst1 in endothelial cells and myeloid precursors were used. N-deacetylase-N-sulfotransferase-1 (Ndst1) is a heparin sulfate enzyme.

Heparin sulfate (HS-GAG), the predominant tissue GAG, is a linear, highly sulfated, heterogeneous polysaccharide composed of alternating residues of N-acetylglucosamine and either D-glucuronic acid or L-iduronic acid. Glucosaminyl N-deacetylase/N-sulfotransferase (NDST) is a modifying enzyme that replaces the acetyl group in N-acetylglucosamine residues with a sulfate. While defects in HS are lethal in mice, a conditional mutation of the Ndst1 gene (Ndst1$^{f/fTekCre+}$) has been developed.

Kidney Transplantation.

Renal allograft transplant was performed as previously described (Table 3; 7-10 mice with allograft transplant per donor organ genetic strain and treatment type; 26 mice in total). In brief, the donor kidney is placed in the left flank in the mouse and attached by end-to-side anastomosis between the donor suprarenal aorta cuff and the recipient aorta. Venous anastomosis between donor suprarenal inferior vena cava (IVC) and recipient IVC is performed in the same fashion and the bladder attached.

TABLE 3

Mouse Renal Allograft Model.

| Donor | Recipient | Treatment | Number of Mice | Follow Up (days) | Survival |
|---|---|---|---|---|---|
| C57Bl/6 (WT) | BALB/c | Saline | 10 | 10 | 10/10 |
| NDST1$^{-/-}$ | BALB/c | Saline | 9 | 9 | 9/9 |
| C57Bl/6 (WT) | BALB/c | M-T7 (100 ng/gm) | 7 | 10 | 7/7 |
| C57Bl/6 (WT) | BALB/c | R$^{171}$E (100 ng/gm) | 10 | 10 | 10/10 |
| C57Bl/6 (WT) | BALB/c | F$^{137}$D (100 ng/gm) | 10 | 10 | 10/10 |
| C57Bl/6 (WT) | BALB/c | E$^{209}$I (100 ng/gm) | 10 | 10 | 10/10 |
| Total numbers of mouse renal allografts | | | 56 | NA | 56 (100%) |

Mice were studied after treatment with either M-T7, one of the three M-T7 point mutations (M-T7-His$_{6X}$, F$^{137}$D, R$^{171}$E, and E$^{209}$I), or saline control (Table 3). A series of donor renal allografts from either C57Bl/6 wild type (WT) or Ndst1$^{-/-}$ (HS/GAG KO) were transplanted into Balb/C mice after resection of both kidneys under general anesthetic. Mice with WT or HS/GAG KO donor allografts were treated with either saline control, M-T7 or individual mutated constructs (M-T7-His$_{6X}$, F$^{137}$D, R$^{171}$E, or E$^{209}$I; 6-10 mice per donor organ strain and per treatment; Table 3). No other immunosuppressants were given to the mice before or after transplantation. Treatments were given daily by intraperitoneal (IP) injection at 100 ng/gm/day for 10 days per mouse for each individual protein treatment. Mice were sacrificed at 10 days follow up.

Renal allografts were divided into 3 sections and each section cut in half; one third fixed in buffered formalin for histology and the other two thirds were cut in half and stored frozen for fluorescence microscopy and HPLC analysis or stored in RNALater. Spleen and blood samples were stored for cell isolation, FACS, and RNA analysis.

M-T7 and M-T7 Point Mutation Generation and Expression.

M-T7 was expressed and purified as previously described. M-T7 was transformed into DH10Bac bacteria (Invitrogen. Carlsbad, Calif.), and blue/white screened on LB+Kan+Tet+Gen+IPTG+X-gal plates. Bacmids were purified and used to transfect Sf9 insect cells with Cellfectin II (Invitrogen, Carlsbad, Calif.). Baculovirus supernatants were collected to infect insect cells and express the various M-T7 mutant proteins. M-T7 was then purified by sequential column purification as previously described.

Histological and Immunohistochemical Analysis of Acute Rejection and Scarring.

Transplant sections for histology were cut into three 1.5-2 mm equal length cross sections, fixed, paraffin embedded, and cut into 4-5 μm sections (3 sections per transplant specimen, providing 9 sections per allograft). Sections were stained with Haematoxylin and eosin (H & E), Masson's trichrome, and Periodic acid-Schiff (PAS) as previously described. All sections were analyzed for selective changes consistent with acute rejection and vasculitis by two pathologists blinded to the mouse donor allograft implant (WT or HS/GAG KO) and to each M-T7 or M-T7 construct treatment. Pathology was scored on a scale of 4. The overall pathology score was a summation of independent scores assessed by detection of cellular infiltrate, vasculitis, glomerultis, peritubular capalaritis, tubulitis, and mesangial matrix.

The score used is the modified BANff score used for detection and measurement of acute renal allograft transplant rejection. This score assesses biopsy specimens embedded cut and stained with Hemaoxylin and eosin or periodic acid Schiff (PAS) to detect inflammatory cell invasion into various parts of the transplanted organs (e.g., arteries, capattaries, glomerulus, tubules) as well as scar and inflammatory tissue formation (e.g., mesangial matrix). Histology scores were measured by two local renal pathologists skilled in transplant rejection analysis. The pathologists were blinded to the mouse strain of the donor graft and or treatments given to transplanted animals.

Donor tissues from both the saline treated groups that were collected 10 days post-transplant were formalin fixed and paraffin embedded and three sections of 4-5 μm thickness were analyzed for six different pathological parameters by pathologists blinded to specimen identities (n=9-10).

Renal allografts were assessed by immunohistochemical staining for macrophage and T lymphocyte invasion using rat anti-mouse macrophage antibody and rabbit polyclonal anti-mouse CD3 (Abcam Inc, Cambridge, Mass.), using the ABC staining technique, as previously described. Sections were incubated with goat anti-rat or anti-rabbit secondary antibody, as indicated, and counterstained with haematoxylin. Mean number of positively stained cells in three high power field (HPF) areas in each renal graft and also allograft arteries were measured using the Image Pro MC6.0 trace application program with an Olympus BX51 microscope imaging system, calibrated to microscope objective. The mean cell count per HPF was calculated.

RT-PCR Array Analysis of Altered Gene Expression in Renal Allografts.

One-third of each transplanted kidney section was collected in RNA later (Ambion, Austin, Tex., USA) and RNA was isolated using RNeasy Mini kit following the manufacturer's protocol (Qiagen, Valencia, Calif., USA). RNA was reverse transcribed to cDNA using Superscript VILO cDNA Synthesis kit (Invitrogen Corporation, 11754-250, California, USA) and Real Time PCR carried out using SYBR Green Core Reagent kit and a 7300 RT-PCR system (Applied Biosystems, Austin, Tex., USA).

Statistical Analysis.

Measured change in acute rejection, tissue mononuclear cell count, percentages of positively stained cells, altered flow cytometry detection of spleen cell populations, PCR array and tissue HS and CS disaccharide content were assessed for statistical significance using analysis of variance (ANOVA) with secondary Fishers PLSD or Student's unpaired, two tailed T test. Multiple regression analysis was performed, calculating the correlation and the predictive value of tissue disaccharide content for reduced renal allograft rejection [31]. For these calculations, significant reduction in acute rejection was assigned the value 1, and a lack of anti-rejection activity was assigned the value 0. The statistical analysis as described herein applies to all of the Examples disclosed unless otherwise indicated.

Results.

Figure 4A:
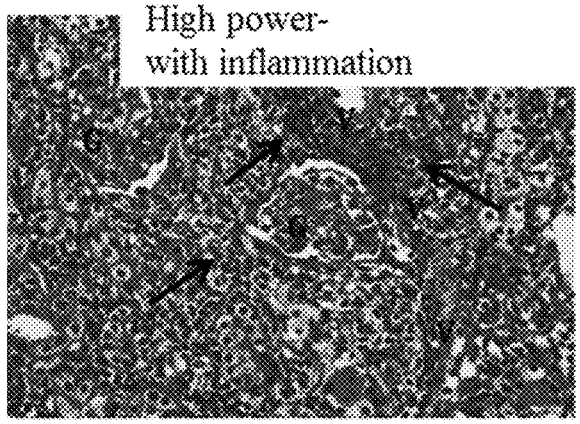
FIGS. 4A-I show the histopathological analysis of renal allograft sections at 10 days post-transplant follow up for saline treated WT (N=10 mice) and Ndst1$^{-/-}$ (N=9 mice) donors. WT donor transplants displayed increased histological markers of acute rejection (A) which were significantly decreased for Ndst1$^{-/-}$ donor transplants (B).
Figure 4B:
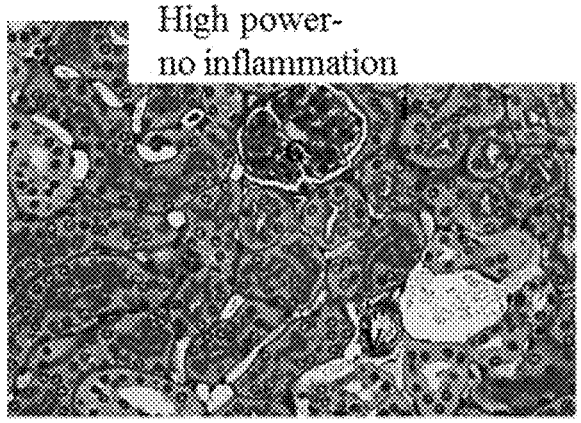
Figures 4C, 4D:
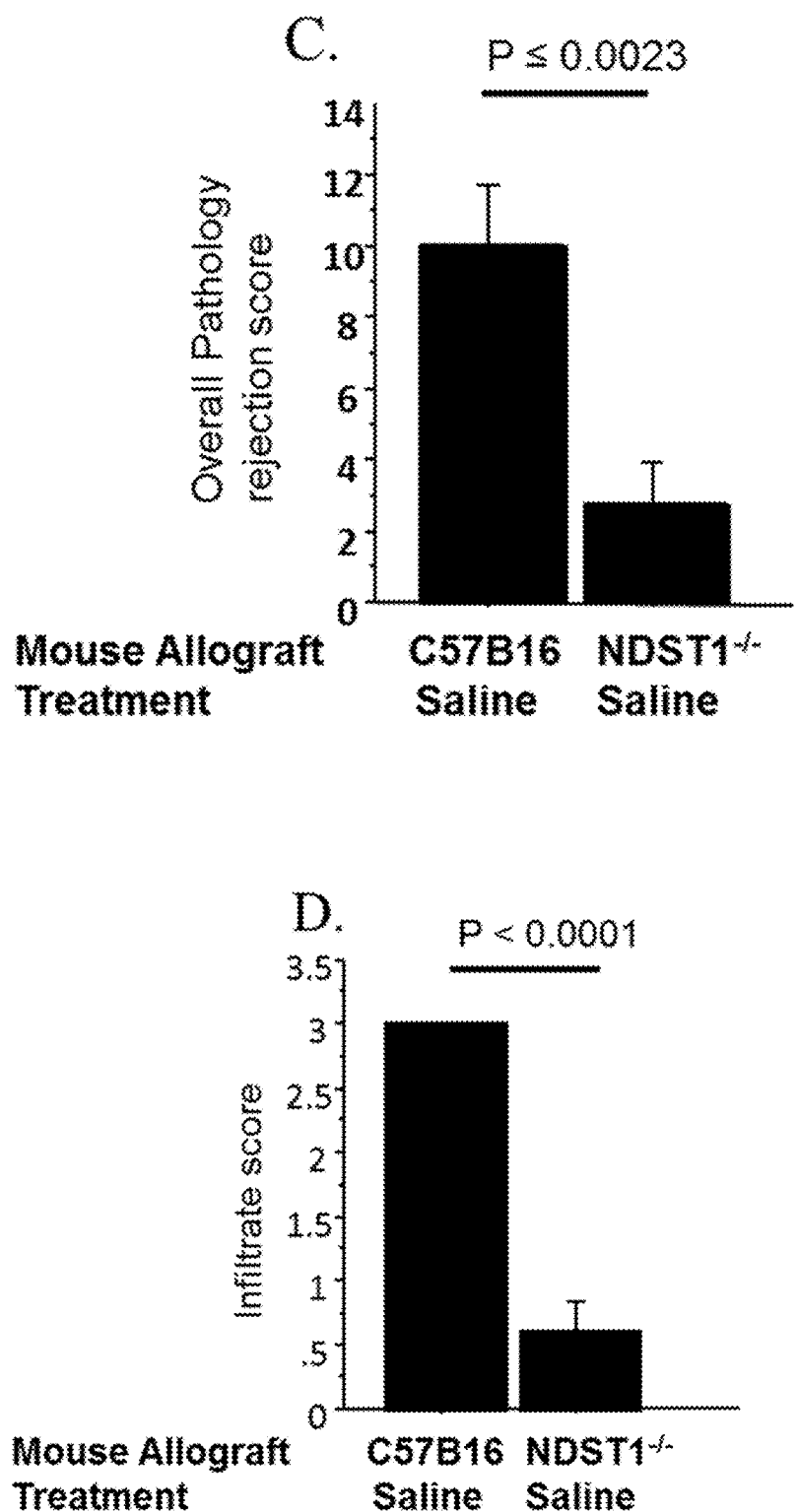
Figure 4E:
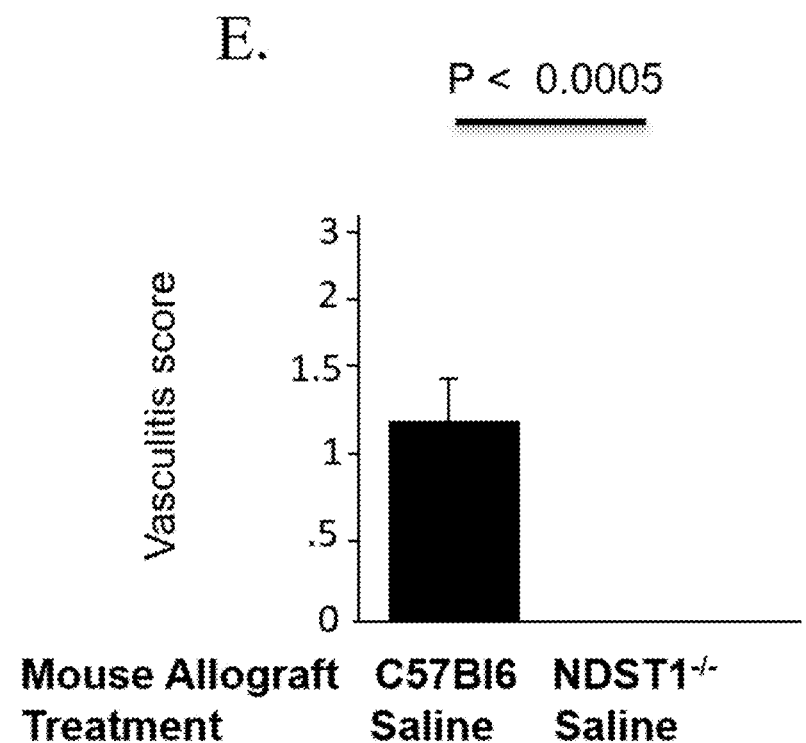
Figure 4F:
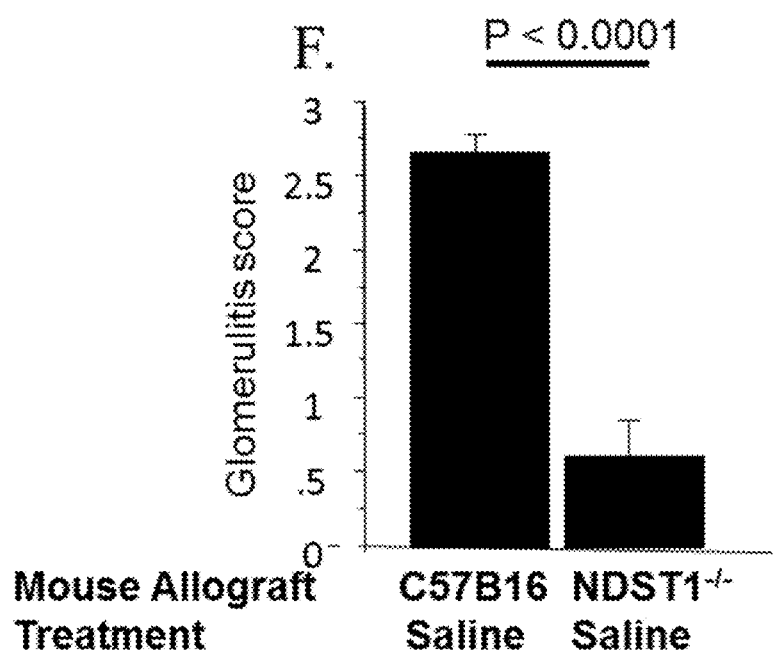
Figures 4G, 4H:
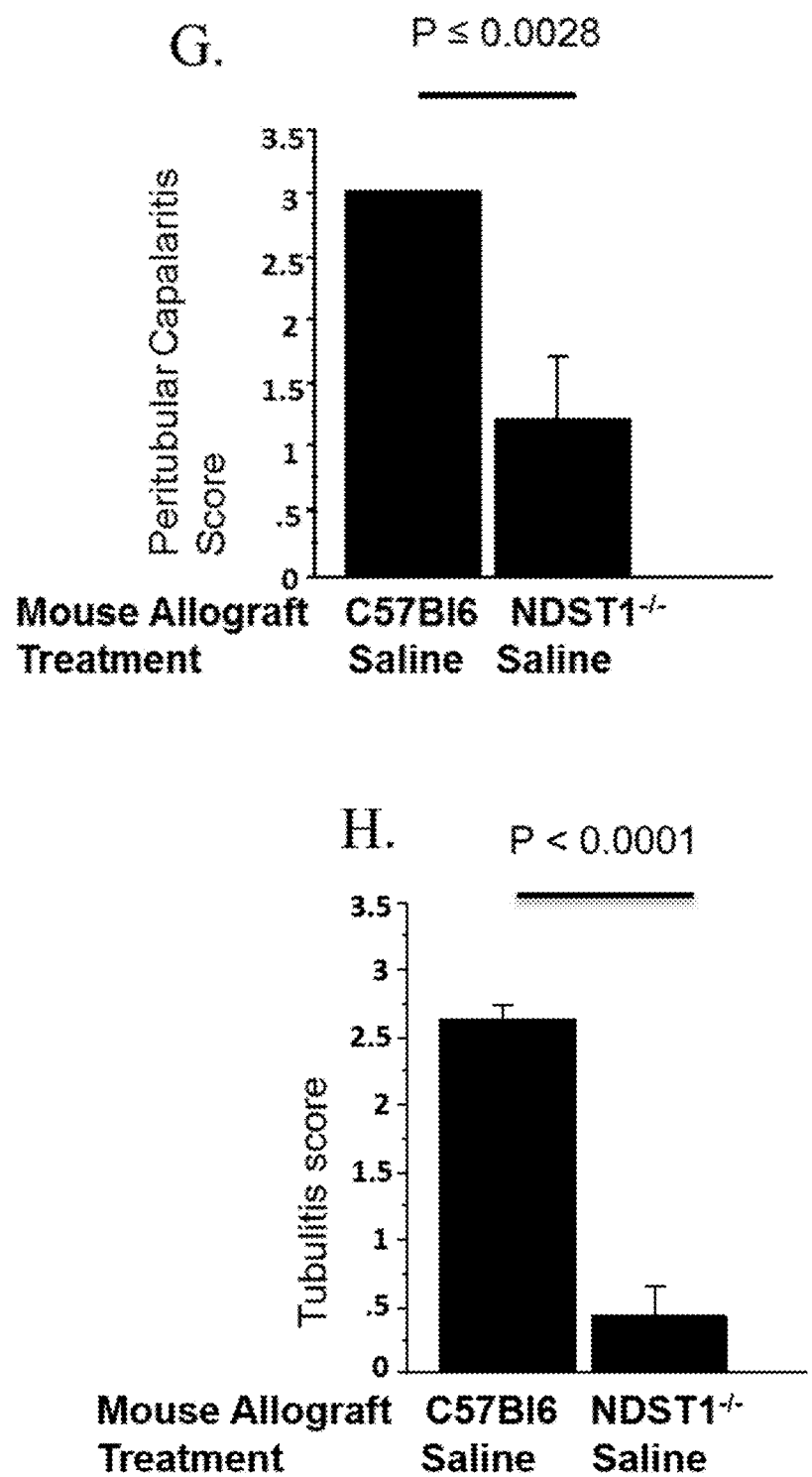
Figure 4I:
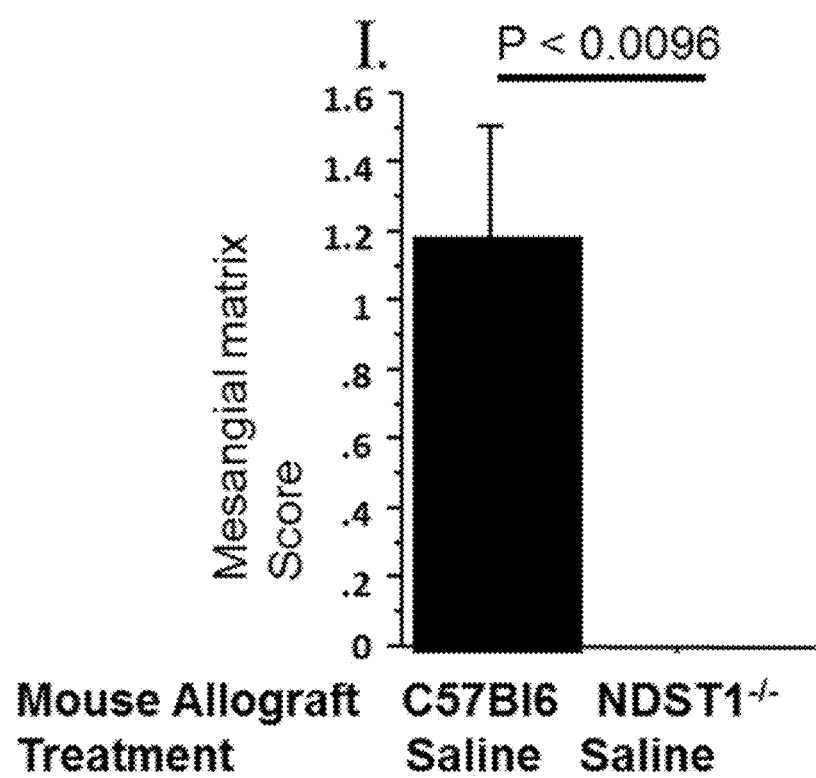

All histological sections were read by pathologists, blinded to donor mouse strain and treatments. Saline treated WT C57Bl/6 renal allografts implanted into BALB/c mice have a marked increase in histological markers of acute transplant rejection. Inflammatory cell infiltrates, vasculitis, glomerulitis, peritubular capalaritis, tubulitis, and mesangial matrix were all increased at 10 days follow-up (FIG. 4A). Donor renal allografts from mice with conditional Ndst1 deficiency (Ndst1$^{-/-}$) had significantly reduced histological markers of early rejection (FIG. 4B). The overall pathology score for early rejection was significantly reduced (FIG. 4C; $P<0.0023$). Scores for cell infiltrates (FIG. 4D; $P<0.0001$), vasculitis (FIG. 1E; $P<0.0005$), glomerultis (FIG. 1F; $P<0.0001$), peritubular capalaritis (FIG. 1G; $P<0.0028$), tubulitis (FIG. 1H; $P<0.0001$), and mesangial matrix (FIG. 1I; $P<0.0096$) were significantly reduced. Thus, donor kidney implants with Ndst1 deficiency in endothelial cells and myeloid precursors had significant reduction in all scores for inflammation and rejection when compared to saline treated WT renal allotransplants into BALB/c recipient mice at 10 days post engraftment.

There was no additional immune modulating therapy given to engrafted mice. Kidneys from donor WT and from Ndst1$^{-/-}$ mice were all implanted into BALB/c mice with normal Ndst1 expression (Ndst1$^{+/+}$). These findings indicate that donor organ Ndst1 enzyme deficiency in the endothelial glycocalyx, and potentially in leukocytes carried into the recipient with the implanted donor kidney, reduce acute allograft inflammation and rejection.

Example 3: M-T7 Treatment Significantly Reduces Histopathological Markers for Acute Allograft Rejection M-T7 and M-T7 Point Mutation Generation and Expression.

M-T7 and M-T7 point mutations were expressed and purified as previously described. In brief, M-T7 mutants were generated by mutagenic PCR using M-T7pFastBacDualeGFP as the template. Mutant constructs and wild type M-T7 were transformed into DH10Bac bacteria (Invitrogen. Carlsbad, Calif.), and blue/white screened on LB+Kan+Tet+Gen+IPTG+X-gal plates. Bacmids were purified and used to transfect Sf9 insect cells with Cellfectin II (Invitrogen. Carlsbad, Calif.). Baculovirus supernatants were collected to infect insect cells and express the various M-T7 mutant proteins (Table 3). M-T7 and each of the three mutant constructs were then purified by sequential column purification as previously described (Bartee Cytokine).

Analysis of GAG Tissue Content in Ndst1$^{-/-}$ Renal Donors and with M-T7 Treatment.

HS GAG and HA-GAG content was measured in kidneys from WT C57Bl/6 and from Ndst1$^{-/-}$ mice with and without treatments with either saline control, M-T7 or each of the individual M-T7 point mutations. Six mice were analyzed per strain and per treatment.

HPLC and/or gel electrophoresis was used to quantitate GAG composition. For HS-GAG measurements, whole tissue samples were homogenized, defatted in acetone for two 24 hr periods. The defatted tissue was weighed and approximately one-third 1/of the sample was transferred to a new container, suspended in 2 mL 0.1 M Tris-HCl, pH 8.0, containing 2 mM CaCl2 and 1% Triton X-100 and pronase was added to bring the whole concentration up to 0.8 mg/mL. Kidney tissue was digested with shaking at 50° C. After 24 h, a second, 1.6-mg, aliquot of pronase was added and digestion continued for 24 h. Samples contained a lot of undigested material, and more buffer and enzyme (2×0.8 mg in 1 mL, was added with 24-h incubation after each addition). The enzyme was then inactivated by heating to 100° C. for 15 min. The buffer was adjusted to 2 mM MgCl2, benzonase (100 mU) was added, and the sample was incubated for 2 h at 37° C. After inactivation of the enzyme (15 min, 100° C.) the undigested tissue was precipitated by centrifugation for 1 h at 4000 g.

The supernatant was applied to a DEAE-Sepharose column (2 mL), washed with 20 mL equilibration buffer (20 mM Tris-HCl, pH 7.5, 0.1 M NaCl), and eluted with 6 mL elution buffer (20 mM Tris-HCl pH 7.5, 2 M NaCl), treated with 0.7 mL 10% (w/v) NaBH4 in 2N NaOH, and incubated overnight at 4° C. The reaction was stopped by adding glacial acetic acid until no bubbles were formed and the pH was neutral. Each sample was then freeze-dried, dissolved in water, desalted using a PD10 column (GE Healthcare), and again freeze-dried and dissolved in water.

Half of the isolated GAG material was used for lyase digestions with Heparinases I-III and incubated over 24 hours (pH 7 for Heparinase enzymes). The enzyme was inactivated by heating to 100° C. for 5 minutes. Samples were centrifuged at 14,000 rpm for 30 minutes before high pressure liquid chromatography (HPLC) analysis. SAX-HPLC was carried out on an Agilent system using a 4.6×250 mm Waters Spherisorb analytical column with 5 μm particle size at 25° C. HPLC were run with two solvents, Solvent A: 2.5 mM sodium phosphate, pH 3.5 and Solvent B: 2.5 mM sodium phosphate, 1.2 M NaCl, pH 3.5 with gradated change form 97% A and 3% B to 100%/b and 0% A over 65 mins at flow rate of 1.0 mL/min. WT kidney samples used 10 L while Ndst1$^{-/-}$ kidneys required SOL. GAG detection was performed by post-column derivatization. Briefly, the eluent from the column was combined with a 1:1 mixture of 0.25 M NaOH and 1% 2-cyanoacetamide pumped at a flow rate of 0.5 mL/min from a binary HPLC pump (Dionex). The eluent was heated to 120° C. in a 10 m reaction coil, then cooled in a 50-cm cooling coil and directed into a Shimadzu fluorescence detector ($\lambda ex=346$ nm, $\lambda em=410$).

Commercial standard disaccharides (Dextra Laboratories) were used for identification of each disaccharide based on elution time, as well as calibration.

Donor tissues from the M-T7 and saline treated groups that were collected 10 days post-transplant were formalin fixed and paraffin embedded and three sections of 4-5 μm thickness were analyzed for 6 different pathological parameters by pathologists blinded to specimen identities (n=7-10).

Results.

Figure 5A:
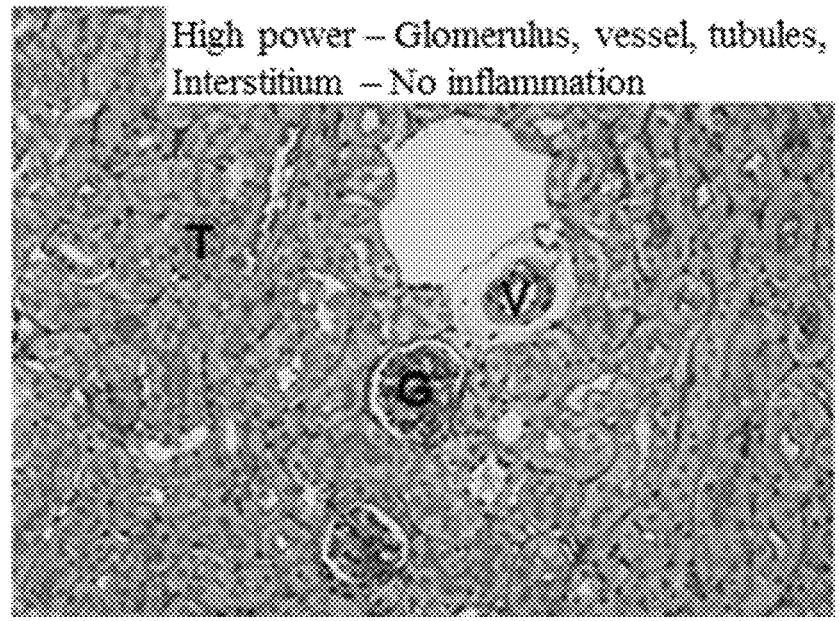
FIGS. 5A-H shows the histopathological analysis of renal allograft sections at 10 days post-transplant follow up after M-T7 treatment of WT donor allografts (N=17 mice). M-T7 treated C57BL6 donor kidney sections demonstrate significantly reduced histopathological markers for acute rejection (A). Overall pathology rejection score is significantly reduced in M-T7 treated mice compared to saline controls (B). Individual pathological scores were significantly reduced in M-T7 treated animals compared to saline controls for Infiltrate (C), Vasculitis score (D), Glomerulitis (E), Peritubular capilaritis (F), Tubulitis (G), but not for Mesanginal matrix (H). P-value≤0.05 considered significant. Mag 200×. T—tubule, G—glomerulus, V—vessel.
Figure 5B:
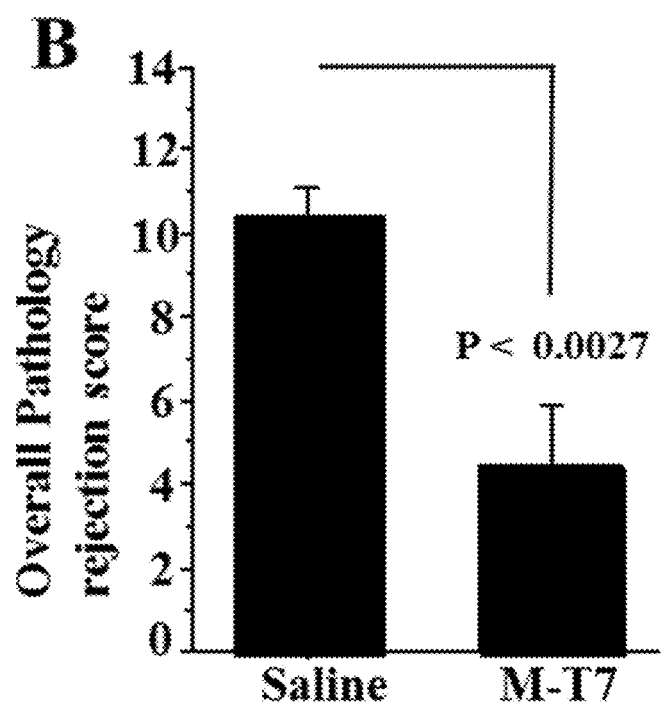
Figures 5C, 5D, 5E, 5F:
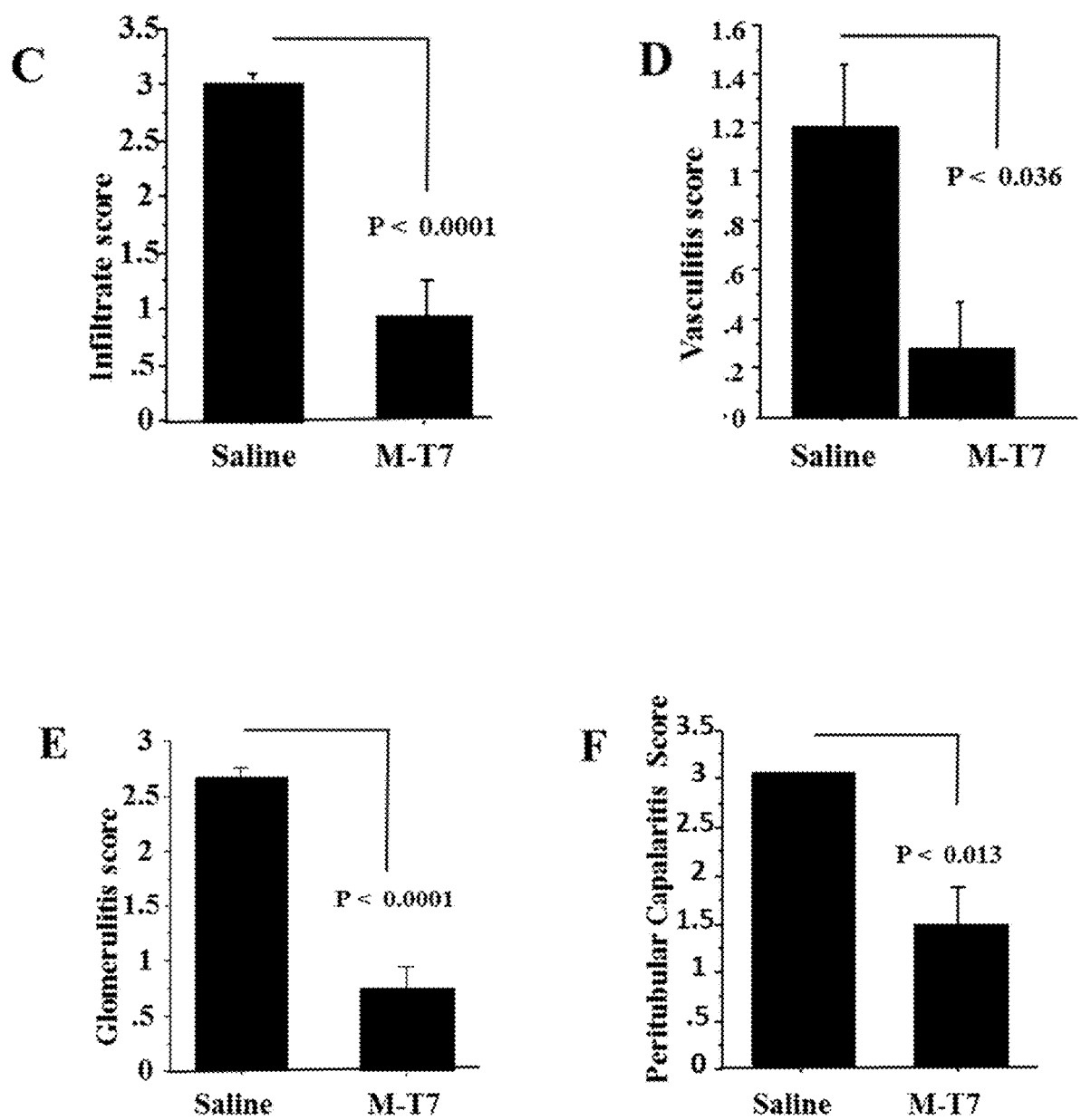
Figures 5G, 5H:
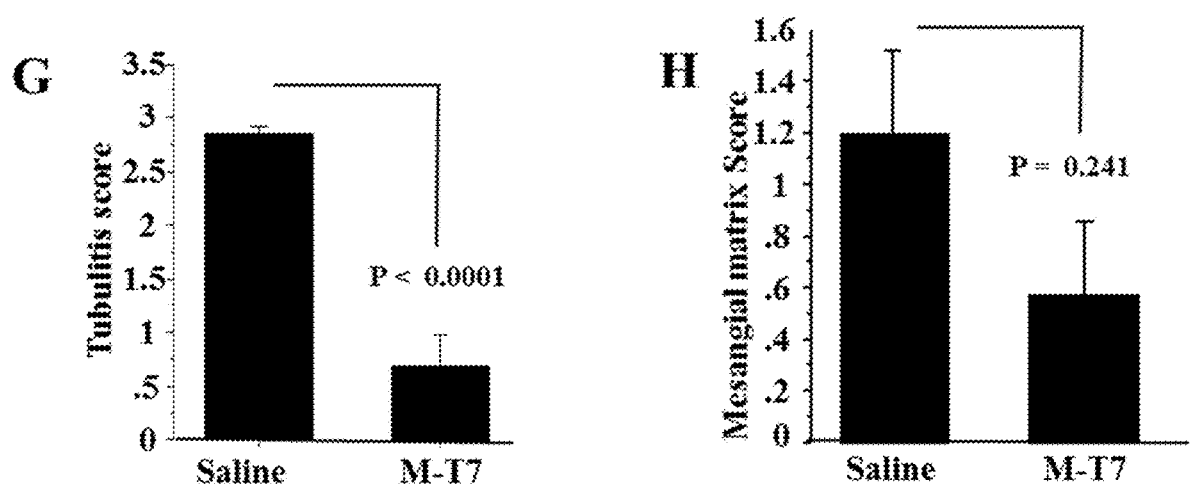

Independent, blinded pathological analysis also demonstrated significant reductions in markers of acute allograft rejection at 10 days follow up with M-T7 treatment (10 daily doses, 100 ng/gm body weight) (FIG. 5A) in WT donor kidney transplants when compared to WT donor allografts treated with saline control (FIG. 4A). M-T7 reduced overall pathology scores for early rejection (FIG. 5B; P<0.0027) with independent reductions in cell infiltrates (FIG. 5C; P<0.0001), vasculitis (FIG. 5D; P<0.036), glomerultis (FIG. 5E; P<0.0001), peritubular capalaritis (FIG. 5F; P<0.013), and tubulitis (FIG. 5G; P<0.0001). M-T7 did not reduce the score for mesangial matrix (FIG. 5H; P=0.241), although showing a trend toward reduction. Changes produced by M-T7 were equivalent to those seen with saline treatment of $Ndst1^{-/-}$ donor allografts implanted into BALB/c recipient mice.

Figure 6A:
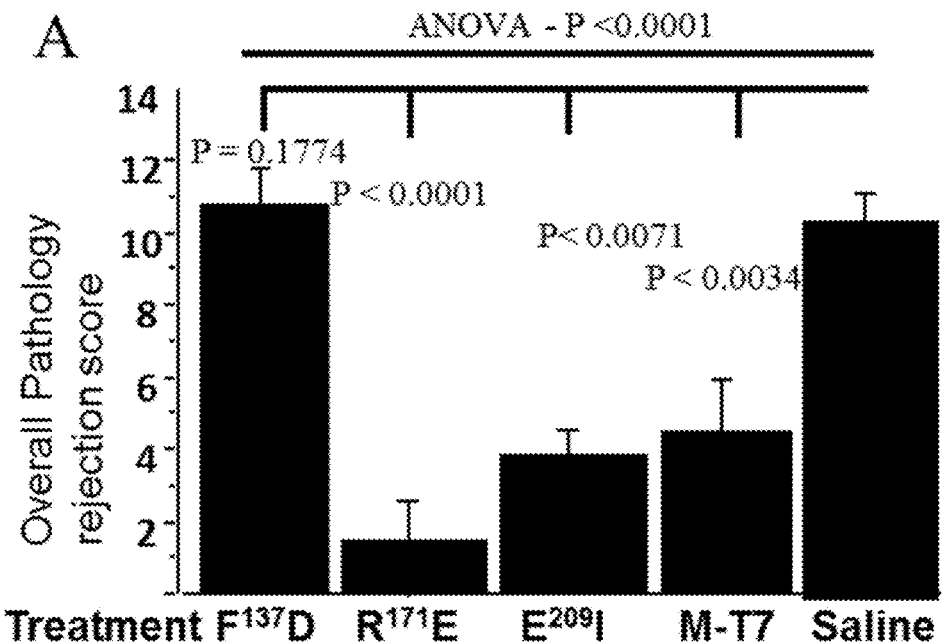
FIGS. 6A-G show the histopathological analysis of renal allograft sections at 10 days post-transplant follow up after M-T7 treatment or M-T7 point mutation treatments (N=47 mice). M-T7, $E^{209}I$ and $R^{171}E$ significantly decreased the histological scores for acute rejection when compared to saline treatment in WT donor transplants, whereas the M-T7 point mutation $F^{137}D$ did not reduce acute rejection. Overall pathology rejection score is significantly reduced with M-T7 as well as with $E^{209}I$ and $R^{171}E$ treated mice compared to saline controls (A). Bar graphs demonstrate significantly reduced individual histopathological scores in M-T7 and in $E^{209}I$ and $R^{171}E$ treated animals for Infiltrate (B), Vasculitis (C), Glomerulitis (D), Peritubular capilaritis (E), and Tubulitis (F) but Mesanginal matrix was only significantly reduced for $E^{209}I$ and $R^{171}E$ but not M-T7 treatments (G). $F^{137}D$ reduced the tubulitis score but did not significantly alter other pathology scores for rejection. P-value≤0.05 considered significant.
Figure 6B:
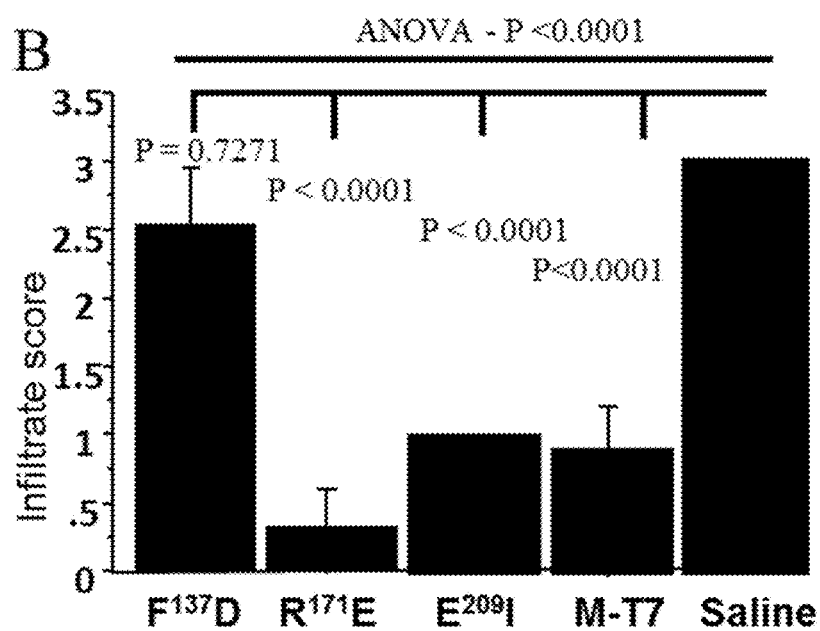
Figures 6C, 6D:
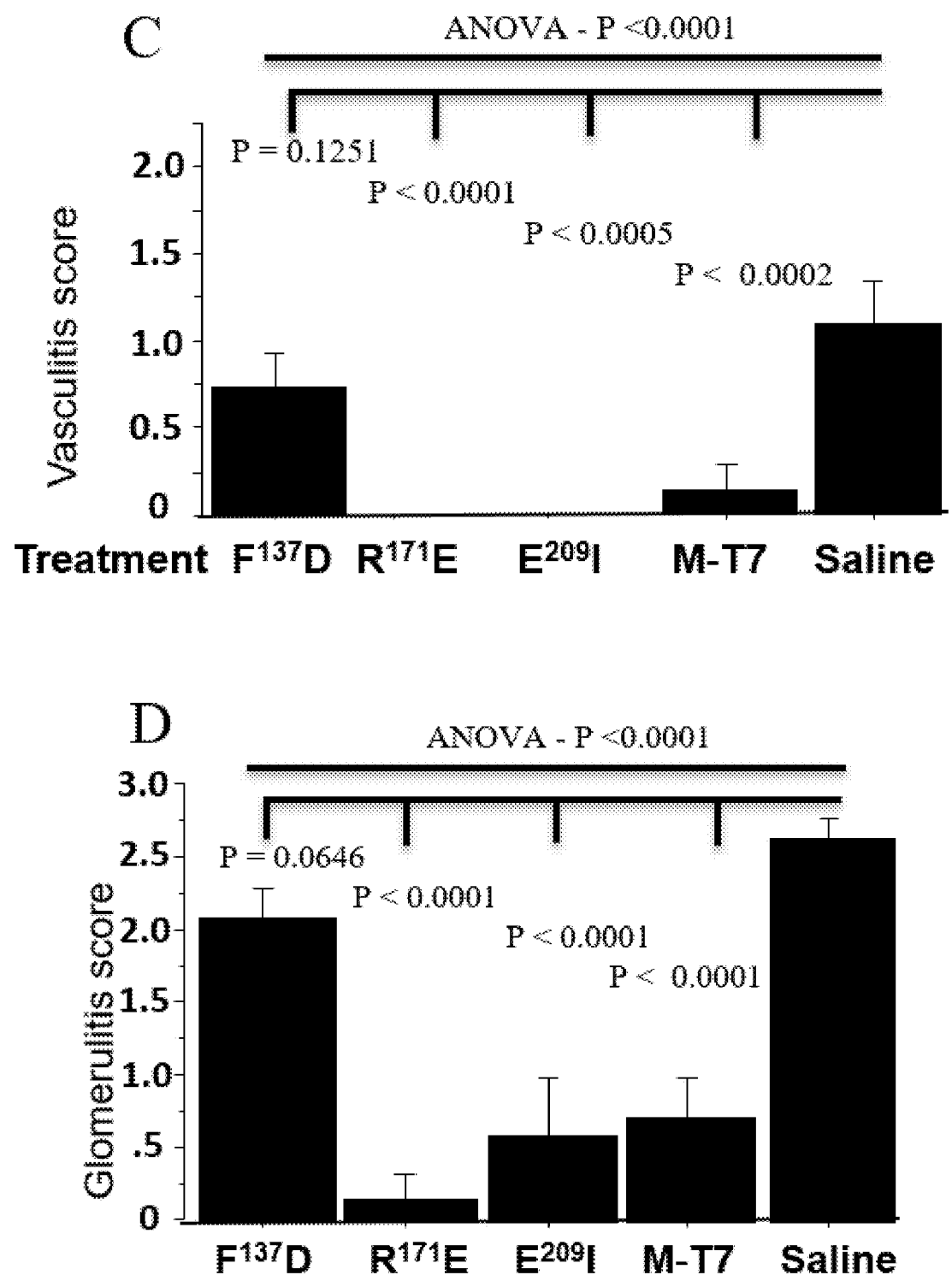
Figures 6E, 6F:
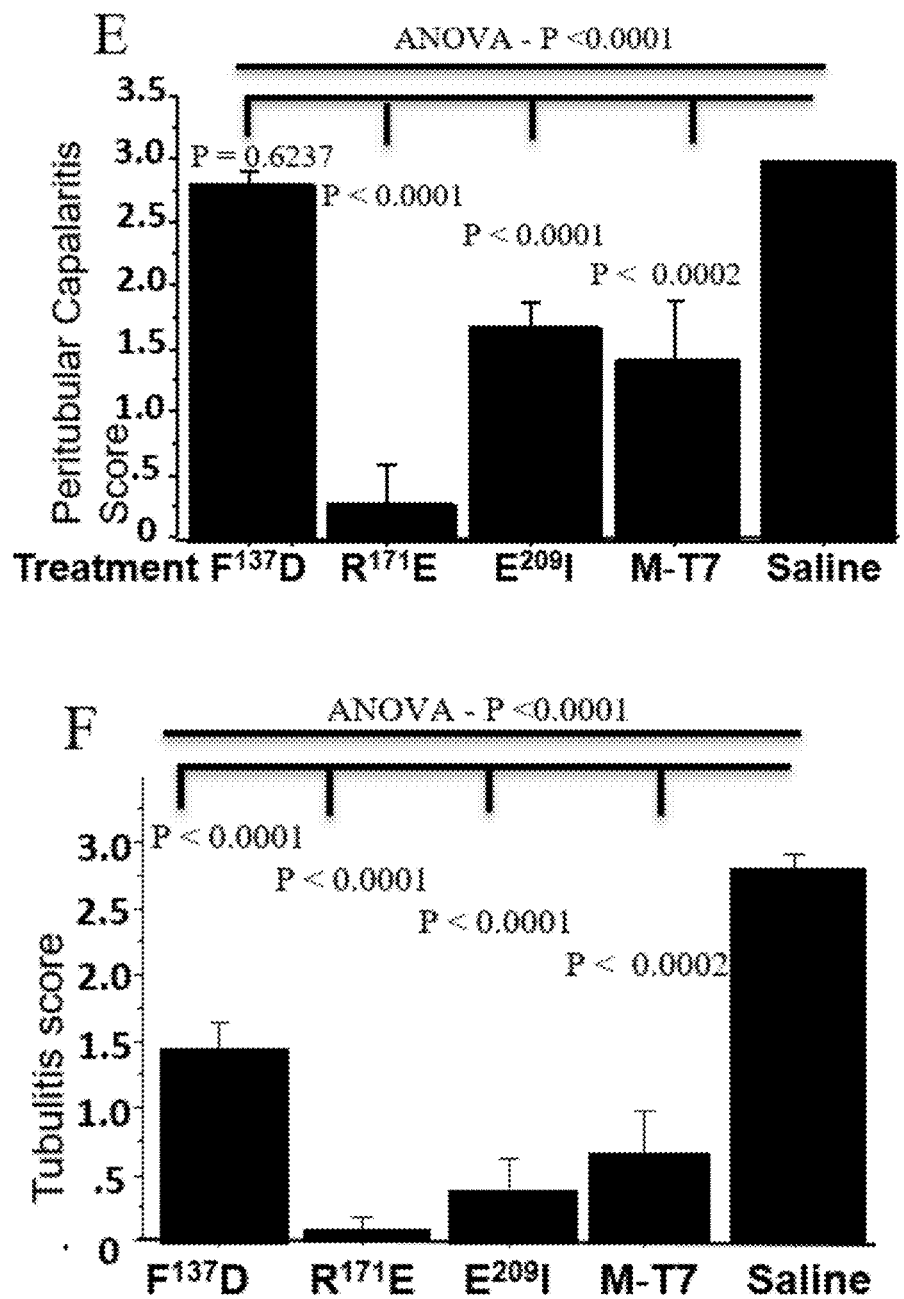
Figure 6G:
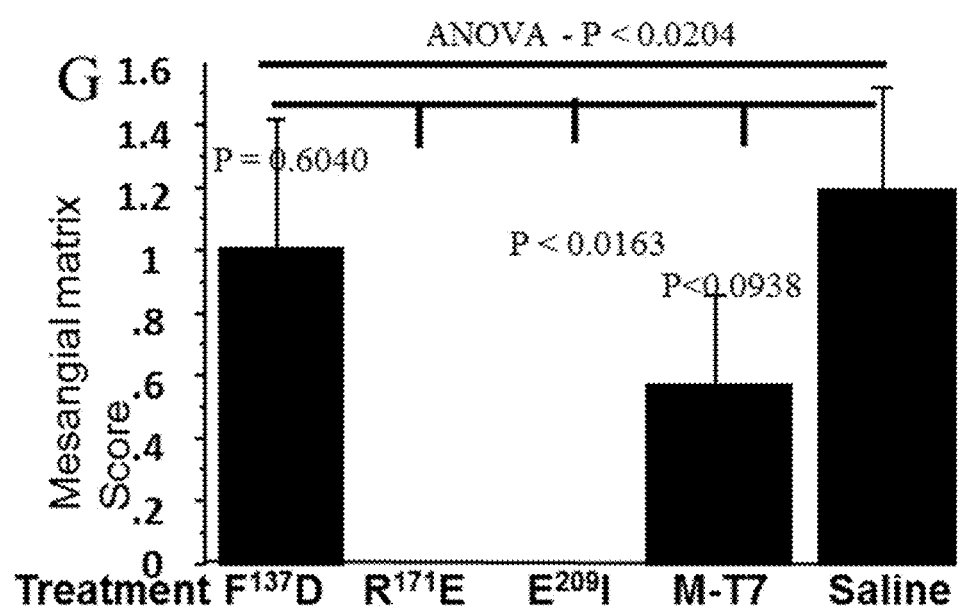

Treatment with the M-T7 point mutations, which were similarly examined, had variable effects on acute WT renal allograft rejection. M-T7 point mutations, E209I and R171E, retained anti-rejection activity similar to M-T7 treatment, while F137D was inactive and did not modify histological parameters for rejection (FIG. 6). Overall pathology score was reduced with E209I (P<0.0071) and R171E (P<0.0001), but not F137D (P=0.1774) (FIG. 6A). Infiltrate (FIG. 6B), vasculitis (FIG. 6C), glomerulitis (FIG. 6D), peritubular capaliritis (FIG. 6E), mesangial matrix (FIG. 6G) followed similar patterns, with only E209I and R171E having significant reductions in each histology score (P≤0.0163). Conversely, F137D as well as E209I and R171E all significantly reduced tubulitis scoring (FIG. 6F; P≤0.0002).

Example 4: Reduced Acute Rejection was Associated with Modified Graft T Cell Invasion and Spleen T Cell Isolates Flow Cytometry Analysis of Mononuclear Cells from Spleen and Blood after Transplant.

To assess a potential effect of GAG/chemokine interactions on systemic T cell responses, splenocytes were isolated for flow cytometry analysis at follow up after renal transplant, as previously described. Cells were pelleted and treated with RBC lysis buffer, washed with PBS, re-suspended in staining buffer containing optimal concentration of fluorochrome-conjugated antibody specific for cell surface antigens (e.g., PE-Cy7, PerCP-Cy5.5, APC, FITC, PE, AF647, eFluor450 for anti-CD4, CD3, CD8, IFNγ, IL-4, IL-17 and FoxP3, respectively, purchased from BD Biosciences and BioLegend). Cells were then re-suspended in staining buffer and analyzed by flow cytometry (Becton-Dickinson FACSCalibur, LSR-II).

Results.

Figures 7A, 7B, 7C, 7D, 7E:
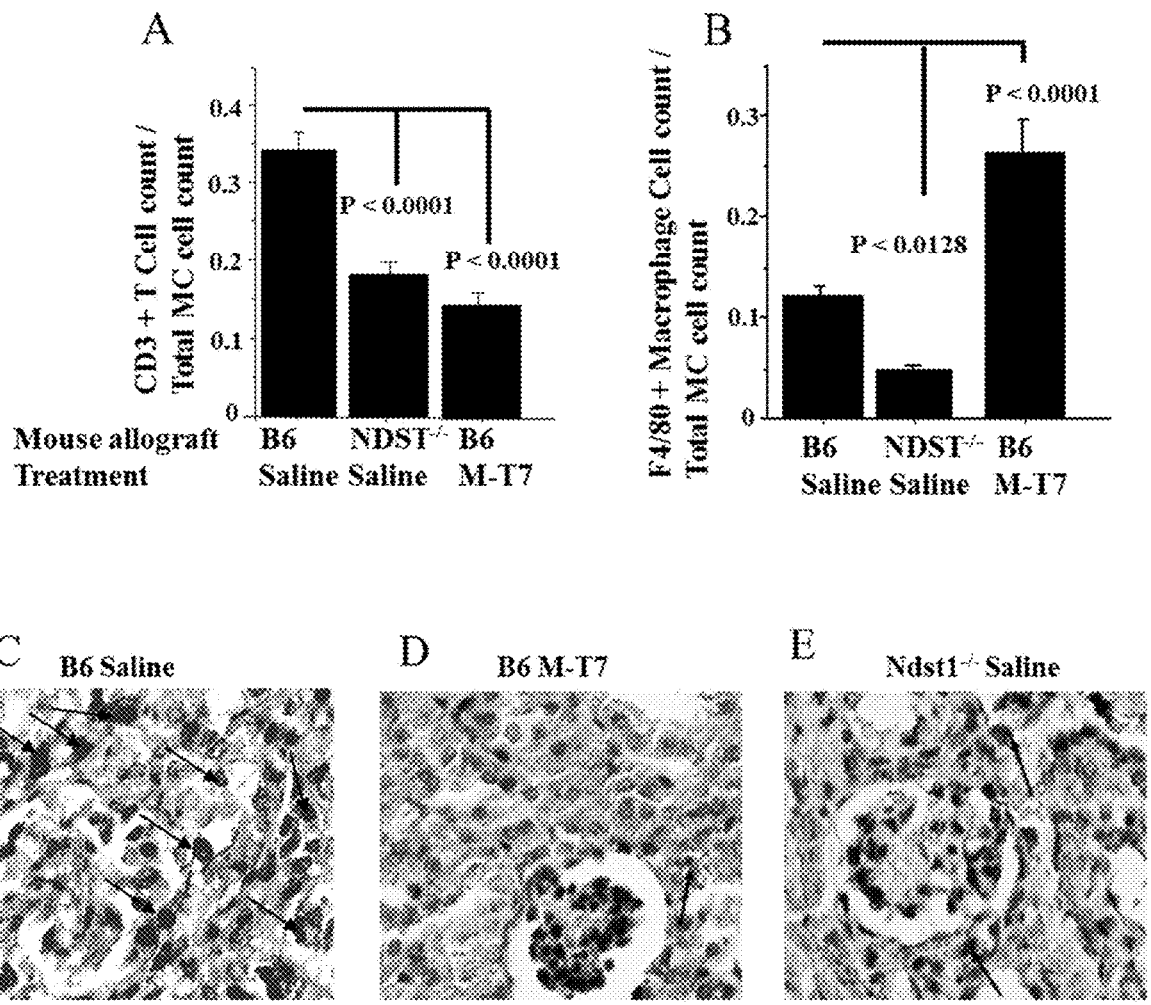
FIGS. 7A-E show the immunohistological analysis of M-T7 treated WT and saline treated Ndst1$^{-/-}$ donor renal allografts at 10 days post-transplant (N=26 mice). Mean numbers of positively stained cells in 3 high power fields (HPF) are presented as bar graphs demonstrating significant decreases in CD3+ T cell infiltrates for saline treated Ndst1$^{-/-}$ donors and for M-T7 treated WT donors (A). F4/80 stained monocytes were significantly decreased in saline treated Ndst1$^{-/-}$ donors but significantly increased in M-T7 treated WT donors (B). Representative CD3+ micrographs (1000×) for immunohistochemical CD3+ stained grafts, saline treated WT (C), M-T7 treated WT (D) and saline treated Ndst1$^{-/-}$ (E). Arrows indicate positively strained cells. P-value≤0.05 considered significant.

On immunohistochemical analysis (FIG. 7) of $Ndst1^{-/-}$ allografts as well as in M-T7 treated WT allografts, significant reductions in CD3 positive T cells was observed (FIG. 7A, B-D). In contrast F4/80 macrophage cell counts were reduced for saline treated $Ndst1^{-/-}$ deficient allografts with reduced rejection (FIG. 7B), and were increased for M-T7 treatment of WT donors.

Figures 8A, 8B, 8C, 8D:
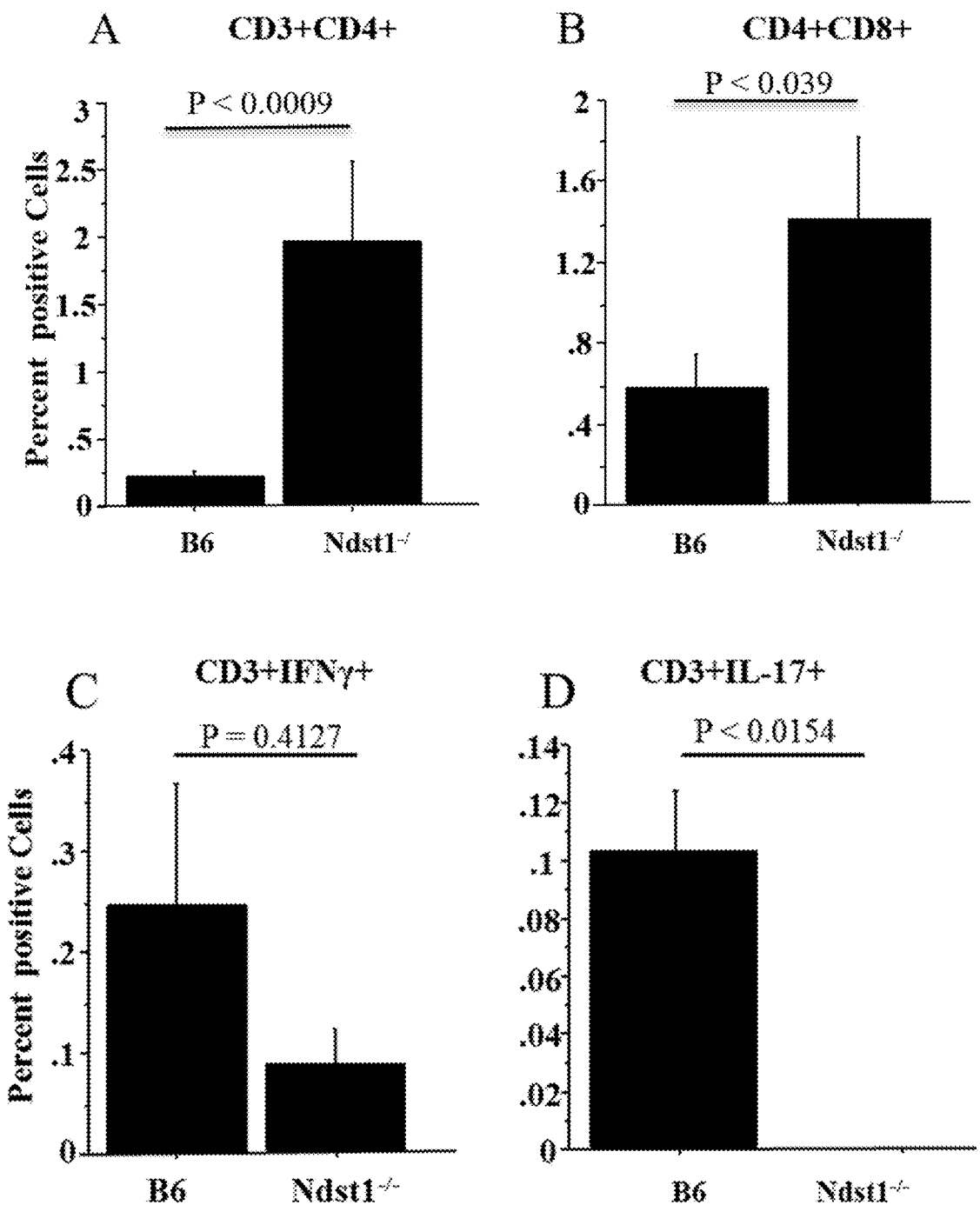

Systemic spleen cell responses were also assessed by flow cytometry analysis. $Ndst1^{-/-}$ transplanted mice had significantly increased CD3+/CD4+ (FIG. 8A; P<0.0009) and CD3+CD8+ (FIG. 8B; P<0.039) percentage cell isolates when compared to WT transplanted mice. $T_H1$ (FIG. 8C) and $T_H17$ (FIG. 8D,K) were both reduced after $Ndst1^{-/-}$ engraftment, with $T_H17$ percentage cell counts (P<0.014) reaching significance.

Figures 8E, 8F, 8G, 8H:
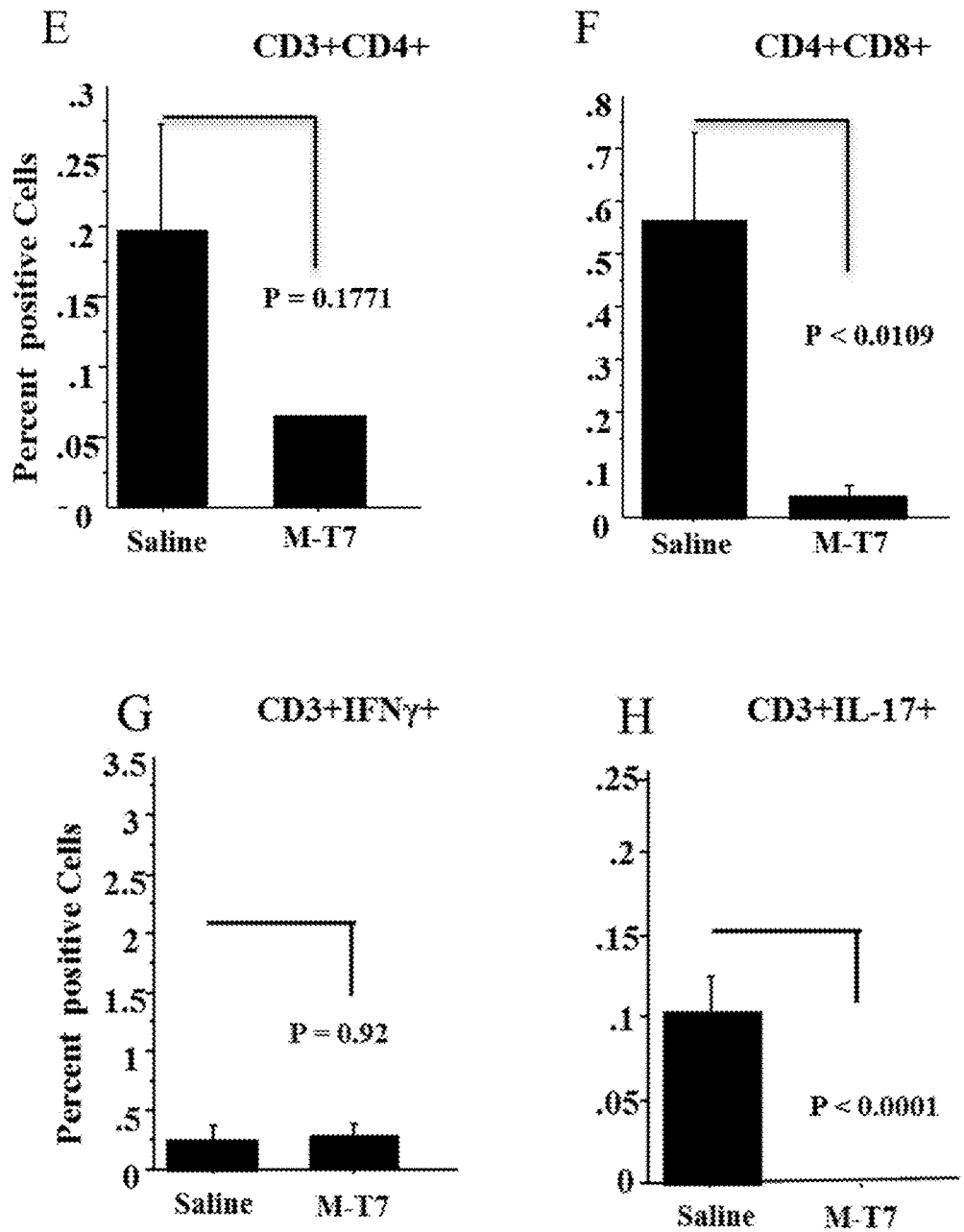

In contrast, M-T7 treated WT transplants had reduced CD3+CD4+ (FIG. 7I) and CD4+CD8+ (FIG. 8E), however, CD4+CD8+ cells were significantly reduced (P<0.0109). CD3+IFNγ+ cells were not altered by M-T7 (FIG. 8F; P=0.92). Similar to saline treated $Ndst1^{-/-}$ grafts, IL17+ ($T_H17$) spleen cell isolates were significantly reduced in M-T7 treated WT engrafted mice (FIG. 8G,K,L; P<0.0001) when compared to saline treated WT. CD83+CD8+ were also significantly reduced by M-T7 (P<0.0109). The CD19 (B cell) response was reduced by M-T7 in WT grafts (P<0.034). CD11c counts were not consistently altered by M-T7 treatment (data not shown).

All other spleen cell isolates examined trended toward a reduction in saline treated $Ndst1^{-/-}$ allograft implants when compared to WT engrafted mice e.g., Fox P3, NK1, CD34, CD83 and CD206, but not CCR6. These reductions in spleen cells, however, did not reach significance. Similarly M-T7 did not display consistent changes in cell counts for these spleen cell subpopulations.

Example 5: Altered Gene Expression in $Ndst1^{-/-}$ Allografts and after M-T7 and M-T7 Mutant Treatments RT-PCR Array Analysis of Altered Gene Expression in Renal Allografts.

One-third of each transplanted kidney section was collected in RNA later (Ambion, Austin, Tex., USA) and RNA was isolated using RNeasy Mini kit following the manufacturer's protocol (Qiagen, Valencia, Calif., USA). RNA was reverse transcribed to cDNA using Superscript VILO cDNA Synthesis kit (Invitrogen Corporation, 11754-250, California, USA) and Real Time PCR carried out using SYBR Green Core Reagent kit and a 7300 RT-PCR system (Applied Biosystems, Austin, Tex., USA).

Results.

Figure 9:
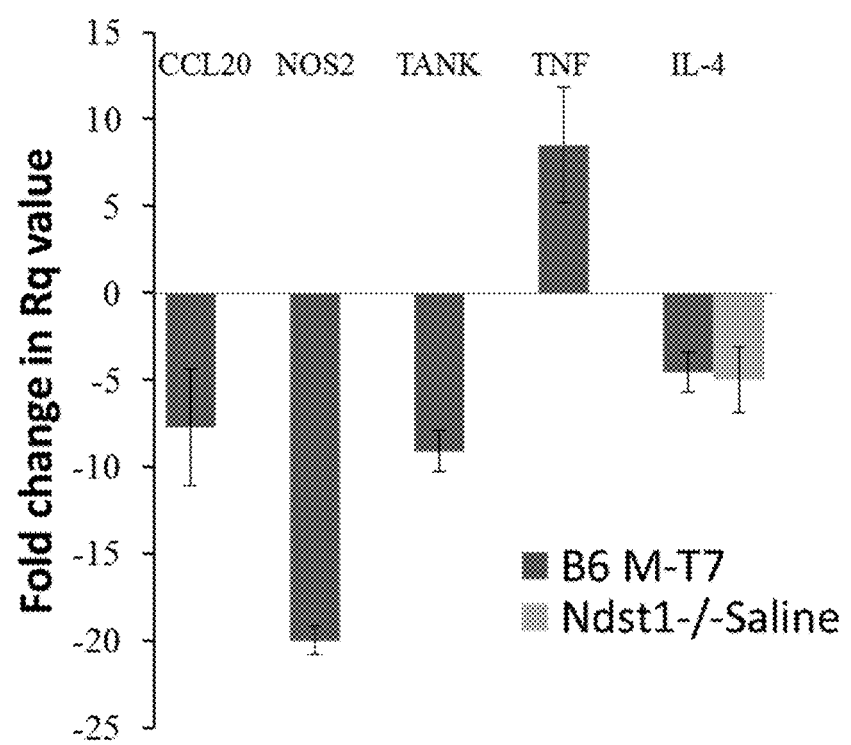
FIG. 9 shows the results of the analysis gene expression in transplanted kidneys detected repressed IL-4 both in saline treated mice that received Ndst-/- donors and the M-T7 treated mice that received WT donors when compared to saline treated WT controls. Kidneys stored in RNALater were homogenized prior to RNA extraction, cDNA was synthesized from the extracted RNA and the selected gene expression was quantified by qPCR. M-T7 treatment also significantly reduced the expression of apoptotic genes CCL20, NOS2 and TANK and increased the expression of TNF. A two-fold change in Rq (relative quantitation) value was treated as significant (n=3).

Significantly altered expression was detected for a subset of genes in signaling pathways as detected by PCR array in renal allograft isolates. Changes in gene expression were assessed for changes that were the same in allografts with reduced rejection when compared to grafts with active rejection, e.g., for either saline treated $Ndst1^{-/-}$ allografts or treatment with M-T7 or M-T7 point mutants, R171E or E209I, with reduced rejection. These changes in gene expression in kidneys with reduced rejection were compared to mice with increased rejection, as for saline treated WT grafts or F137D treatment in WT grafts (FIG. 9). Of these gene expression changes, interleukin 4 (IL-4) was significantly decreased for both $Ndst1^{-/-}$ and M-T7 treated WT grafts at 10 days follow up (FIG. 9). Heat shock transcription factor 1 (HSF1), peroxisome proliferator-activated receptor gamma (PPARG), telomerase reverse transcriptase (TERT), and WNT1 inducible signaling pathway protein 1 (WISP1) were significantly down-regulated in $Ndst1^{-/-}$ grafts. MDM2 was significantly increased, while nitric oxide synthase 2 (NOS2), TRAF family member-associated NFκB activator (TANK), early growth response 1 (EGR1) and fibronectin 1 (FN1) were significantly decreased for M-T7 and E209I treated grafts, but not Ndst1$^{-/-}$ renal allografts. Gene expression for CC chemokine CCL20, heat shock protein 90AA2 (HSP90AA2), IGFBP3, selectin E (SELE), were down-regulated whereas CSF2, FIXA2 and TNF were upregulated with M-T7 treatment in WT grafts. Associated with the NFκB inflammatory pathway, CC chemokine (CCL20) and nitric oxide synthase 2 (NOS2) were decreased in M-T7 or R171E treated WT allografts and TRAF family member-associated NFκB activator (TANK) was decreased by M-T7, R171E and E209I (FIG. 9).

Specific gene expression changes were thus detected in NFκB and JAK/STAT pathways. In the NFκB pathway, CCL20 was reduced. Similarly, nitric oxide synthase 2 (NOS2) and TANK were reduced with M-T7, R171E and E209I treatment in WT transplants. Associated with the janus kinase/STAT (JAK/STAT) pathway, interleukin-4 (IL-4) was significantly reduced in Ndst1$^{-/-}$ grafts with saline treatment or in WT allografts with M-T7 while NOS2 was significantly reduced in M-T7 or R171E treatments in WT allografts (FIG. 9). Murine double minute 2 (MDM2), a p53 regulator, is increased by M-T7 or active point mutations, R171E and E209I, but also by F137D which does not reduce rejection, suggesting a poor association with reduced rejection. In summary, a series of genes in inflammatory signaling pathways demonstrated altered expression in grafts with reduced rejection. While significant changes were detected, the pathways affected differed in Ndst1$^{-/-}$ grafts when compared to M-T7 or active M-T7 point mutation treatments in WT grafts, indicating differing targets for resulting decreases in rejection.

These data show significant changes in gene expression on PCR array analysis of renal allografts sections at 10 days post-transplant (N=56 mice). Comparison of gene expression changes for saline treated Ndst1$^{-/-}$ grafts with M-T7 treated WT grafts with comparison to saline treated WT grafts. Comparison of saline treated Ndst1$^{-/-}$ donors grafts with M-T7, E$^{209}$I, R$^{171}$E and F$^{137}$D treated WT grafts with saline treated WT grafts. IL-4 demonstrated significant decrease for both saline treated Ndst1$^{-/-}$ and M-T7 treated WT renal allografts.

Example 6: HS Disaccharide Content in Saline Treated Ndst1$^{-/-}$ and in Saline or M-T7 Treated WT Kidneys Analysis of GAGs in kidneys from saline treated Ndst1$^{-/-}$ and WT mice with and without M-T7 treatment. Total HS- and CS-GAG and disaccharide content (percent weight) and percent moles sulfate were measured in kidneys from a separate set of Ndst1$^{-/-}$ mice with saline injection treatments and WT C57Bl/6 mice, with and without saline or M-T7 treatment (N=10, 3-4 mice per strain and treatment group). Researchers were blinded to samples (SA, PA). HPLC was used to quantitate GAG composition [30]. For HS-GAG measurements, whole tissue samples were homogenized, defatted in acetone for two 24 hours periods, and suspended in 0.1 M Tris-HCl, pH 8.0, containing 2 mM CaCl2 and 1% Triton X-100. Kidney tissue was digested with pronase (0.8 mg/mL) at 50° C. followed by benzonases (100 mU). Enzymes were heat inactivated at 100° C. for 15 mins and then undigested tissue was precipitated by centrifugation (1 h at 4000 g).

Glycosaminoglycans were isolated from the digested material by passing the sample through a weak anion exchange column (DEAE-Sephacel, GE Healthcare), washing with buffer (20 mM Tris-HCl, 0.1M NaCl, pH 7.5) then eluting (20 mM Tris-HCl, 2M NaCl, pH 7.5). Following isolation the GAGs were released with β-elimination (1% w/w sodium borohydride in 2N NaOH), desalted with a PD-10 column (GE Healthcare), and freeze-dried before disaccharide compositional analysis.

Figure 11:
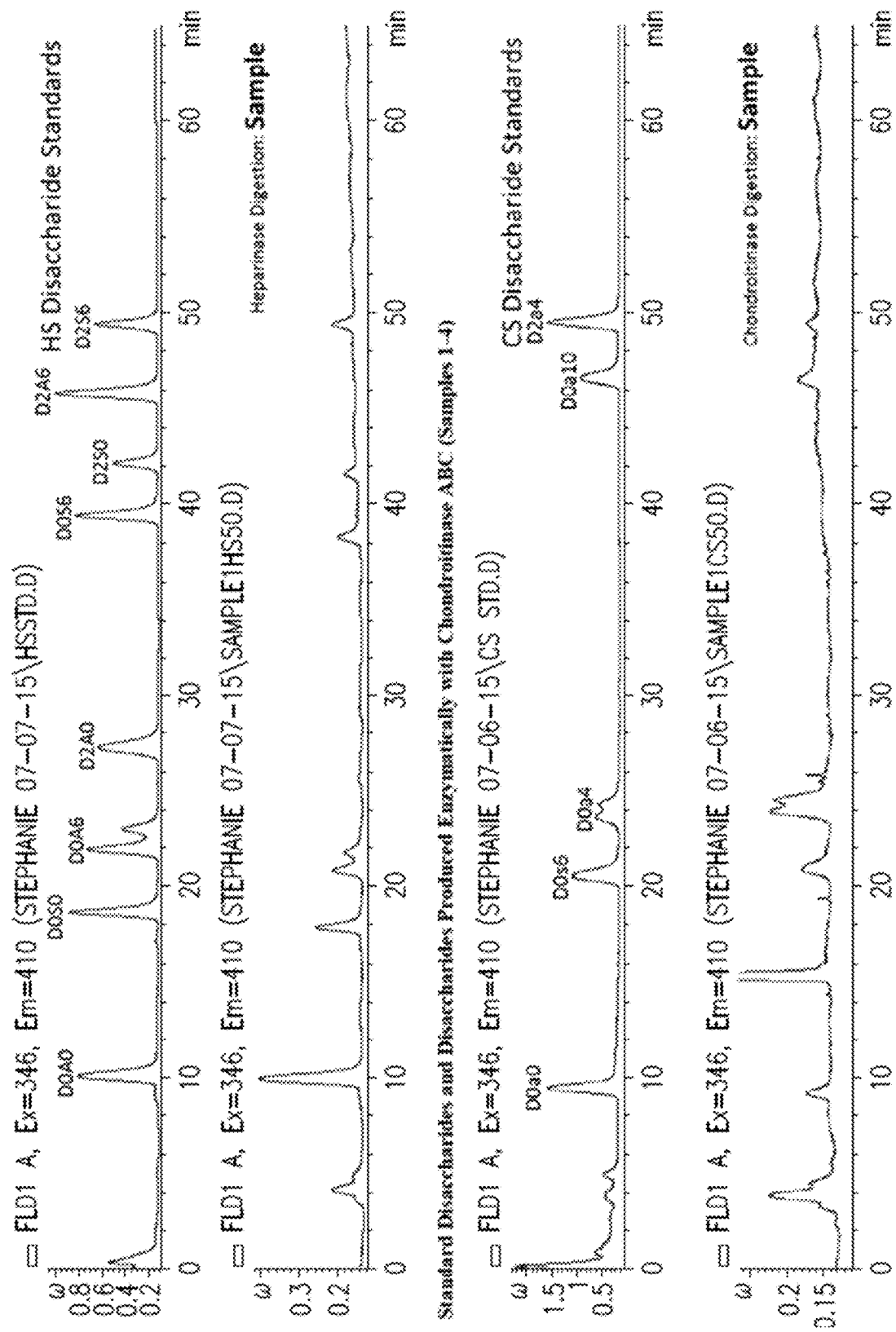
FIG. 11 shows standard disaccharides and disaccharides produced enzymatically with heparinases I-III by HPLC analysis.

Samples were digested with Heparinases I-III, producing disaccharides and separated using SAX-HPLC coupled to post-column fluorescence labeling and detection. Peak migration times and areas as compared to known disaccharide standards were calculated. Representative chromatograms are shown in FIG. 11. SAX-HPLC is performed on an Agilent system using a 4.6×250 mm Waters Spherisorb analytical column with 5 μm particle size at 25° C. HPLC were run with two solvents, Solvent A: 2.5 mM sodium phosphate, pH 3.5 and Solvent B: 2.5 mM sodium phosphate, 1.2 M NaCl, pH 3.5 with gradated change from 97% A and 3% B to 100% B and 0% A (65 mins, flow rate 1.0 mL/min). GAG detection was performed by post-column derivatization. Briefly, the eluent from the column was combined with a 1:1 mixture of 0.25 M NaOH and 1% 2-cyanoacetamide pumped at a flow rate of 0.5 mL/min from a binary HPLC pump (Dionex). The eluent was heated to 120° C. in a 10 m reaction coil, then cooled in a 50 cm cooling coil and directed into a Shimadzu fluorescence detector (λex=346 nm, λem=410). Commercial standard disaccharides (Dextra Laboratories) were used for identification of each disaccharide based on elution time, as well as for calibration.

Results.

Given the marked reduction in acute rejection after renal transplant of Ndst1$^{-/-}$ donor kidneys, the HS and CS disaccharide content in whole kidney isolates from saline treated Ndst1$^{-/-}$ and from saline or M-T7 treated WTs was examined to assess whether there was a change in whole kidney GAG content in either Ndst1$^{-/-}$ or in M-T7 treated WT kidneys. As kidney samples vary in weight, disaccharides were normalized to total HS or CS content. Ndst1 is a sulfotransferase enzyme and, therefore, moles of disaccharides and specifically fractional content (percentage) moles of sulfated 2-O, 6-O and N sulfated disaccharides were calculated, normalized to total content.

Figures 10A, 10B, 10C, 10D:
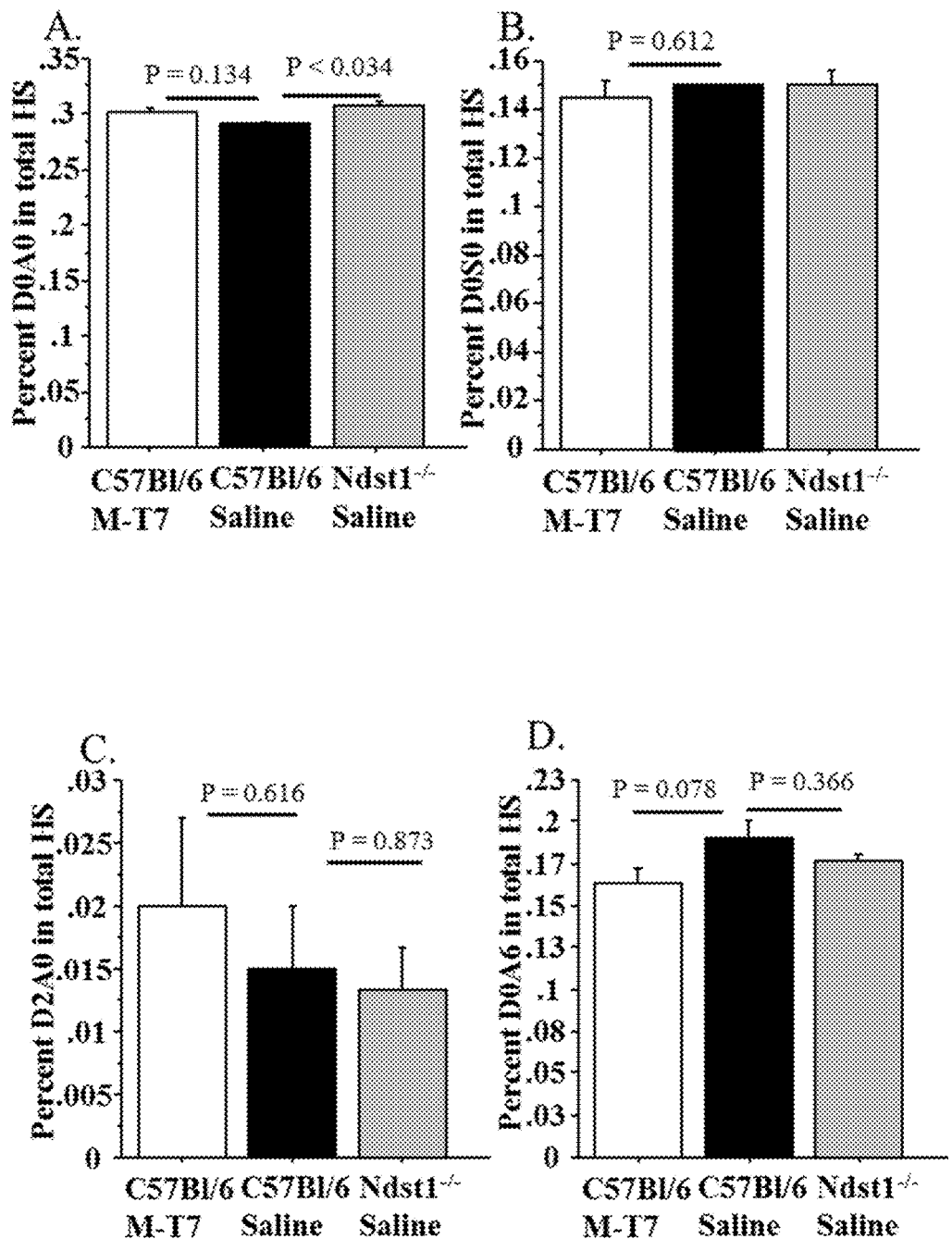
FIGS. 10A-G show bar graphs demonstrating changes in disaccharide content, measured as weight per weight fractions of total HS extracts, from saline treated Ndst1$^{-/-}$ and saline or M-T7 treated WT mouse kidneys after 10 days treatment. HS Disaccharide analysis for D0A0 (A), D0S0 (B), D2A0 (C), D0A6 (D), D0S6 (E), D2S0 (F), and D2S6 (G). D0S0 is increased for both saline treated Ndst1$^{-/-}$ and M-T7 treated WT kidneys, but only Ndst1$^{-/-}$ is significantly increased (A). D0S6 fraction is significantly reduced for saline treated Ndst1$^{-/-}$ and for MT7 treated WT kidneys (E). Multiple regression analysis of individual HS disaccharide weight changes (F) and nmole changes (G) demonstrated significant predictive correlations for measured disaccharide content with potential to reduce rejection.
Figures 10E, 10F, 10G:
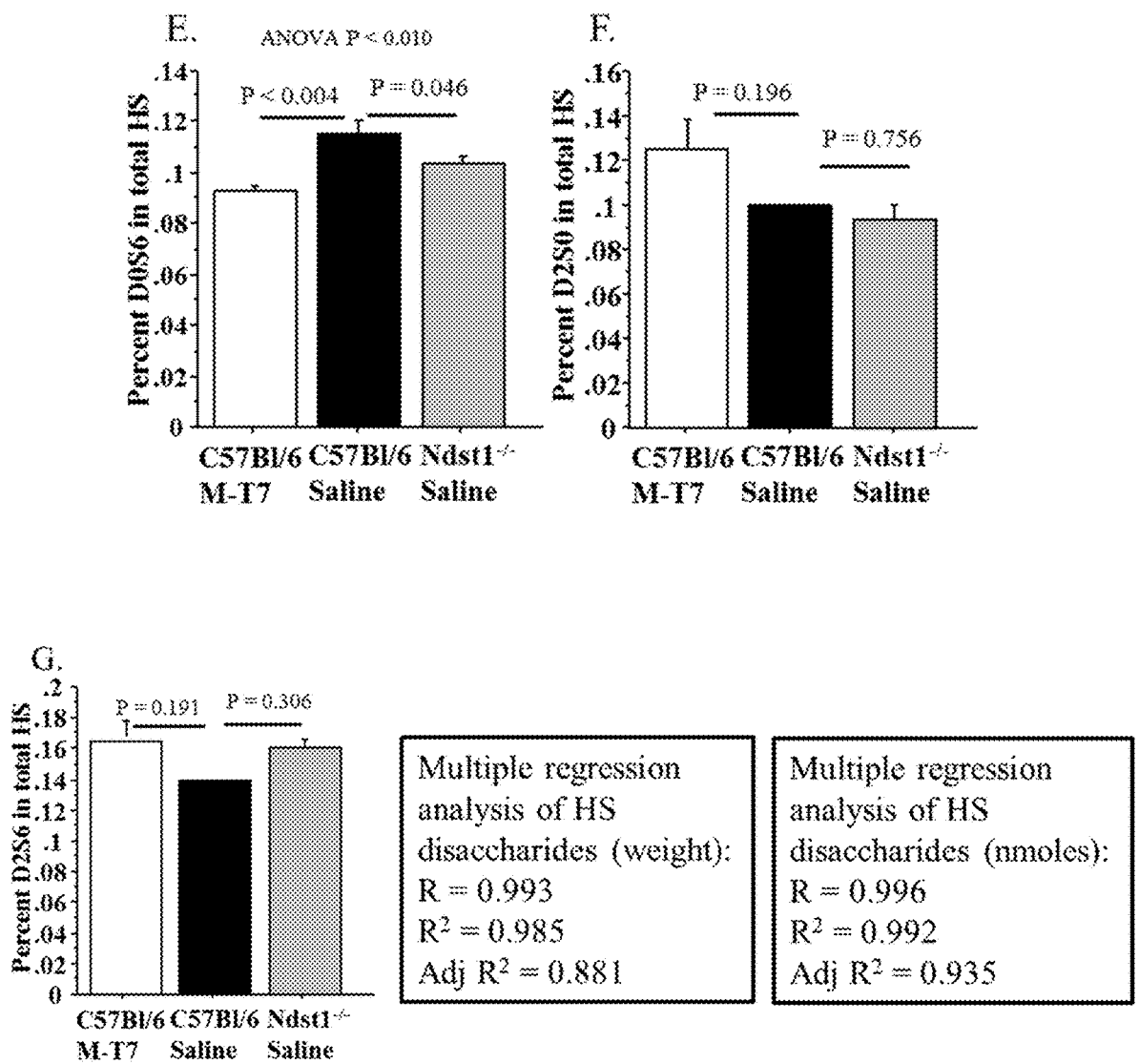

Individual HS disaccharide percentage weights were normalized to total HS weight (weight/weight sample). Ndst1$^{-/-}$ kidneys and M-T7 treated WT kidneys had specific percentage disaccharide changes (weight/weight sample), when compared to saline treated WT kidneys (FIG. 10). Simple comparison for total HS or CS detected non-significant changes. The percent weight (μg) of disaccharides D0S6 (FIG. 10E) and D0A6 (FIG. 10C) were decreased in saline treated Ndst1$^{-/-}$ and in M-T7 treated WT kidneys (for Ndst1$^{-/-}$—P<0.046 for D0S6, P=0.336 for D0A6; for M-T7 treated WT—P<0.004 for D0S6, P=0.078 for D0A6) when compared to saline treated WT kidneys (for D0S6, ANOVA P<0.010). The non-sulfated disaccharide D0A0 was increased for Ndst1$^{-/-}$ (P<0.034), with a borderline trend toward increase for M-T7 treated WT kidneys (P=0.134; FIG. 10A). Other disaccharides, D0S0 (FIG. 10B), D2S0 (FIG. 10B), D2A0 (FIG. 10D), D2S0 (FIG. 10F) and D2S6 (FIG. 10G), did not show significant changes.

Figures 12A, 12B, 12C:
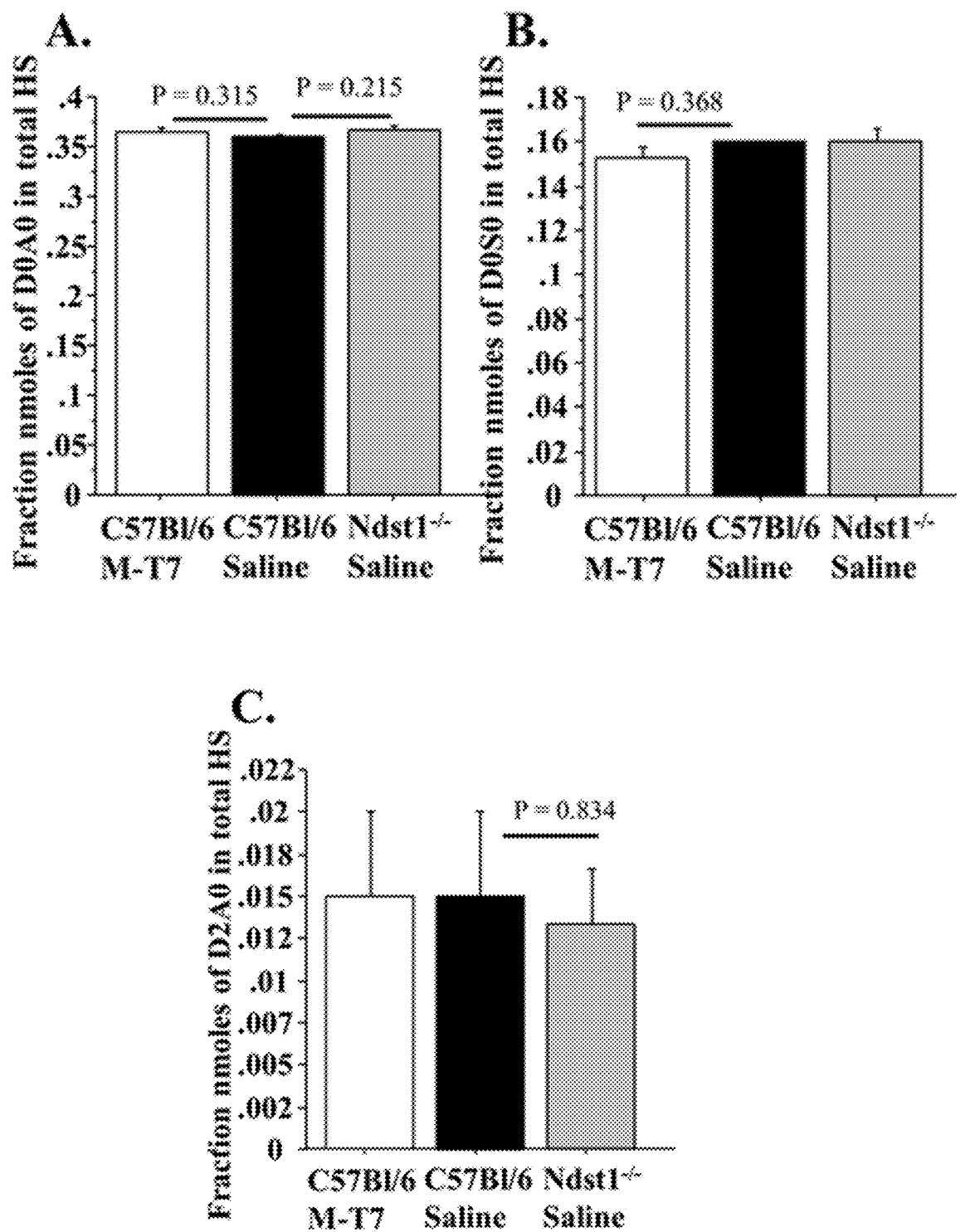
FIGS. 12A-I show bar graphs demonstrating changes in disaccharide content, measured as nmoles per total HS extracts, from saline treated Ndst1$^{-/-}$ and saline or M-T7 treated WT mouse kidneys after 10 days treatment. HS Disaccharide analysis for D0A0 (A), D0S0 (B), D2A0 (C), D0A6 (D), D0S6 (E), D2S0 (F), and D2S6 (G). D0S0 is increased for both saline treated Ndst1$^{-/-}$ and M-T7 treated WT kidneys (A). D0S6 nmole fraction is reduced for saline treated Ndst1$^{-/-}$ and for MT7 treated WT kidneys (E). Multiple regression analysis of individual HS disaccharide weight changes (H) and nmole changes (I) demonstrated significant predictive correlations for measured disaccharide content with potential to reduce rejection.
Figures 12D, 12E, 12F:
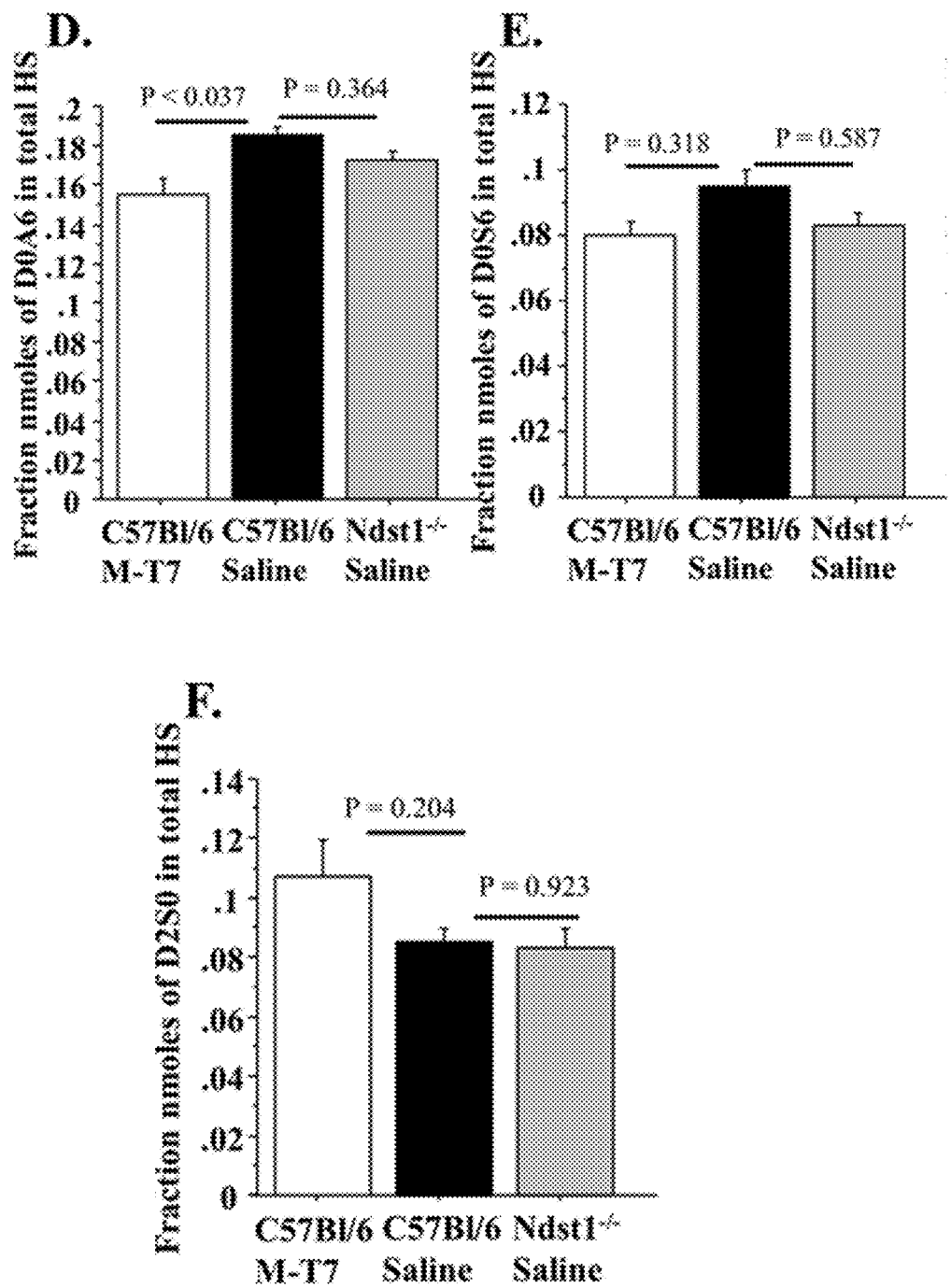
Figures 12G, 12H, 12I:
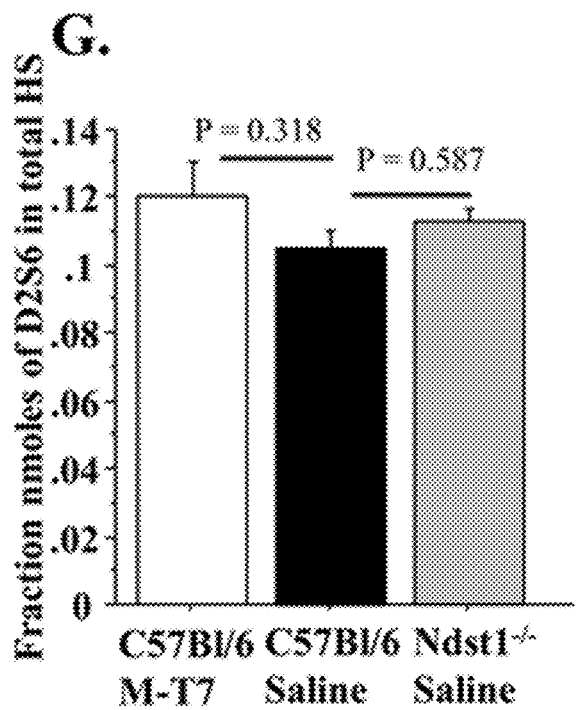

When comparing percent nmole HS disaccharides, D0A6 (FIG. 12) and D0S6 (FIG. 12) also had reduced nmol disaccharide in Ndst1$^{-/-}$ and M-T7 treated WT kidneys when compared to WT controls, while D0A6 was significantly reduced in M-T7 treated WT kidneys (P<0.0375); moles back calculated from weight, disaccharide nmol normalized to sample HS nmol.

Figures 13A, 13B, 13C, 13D:
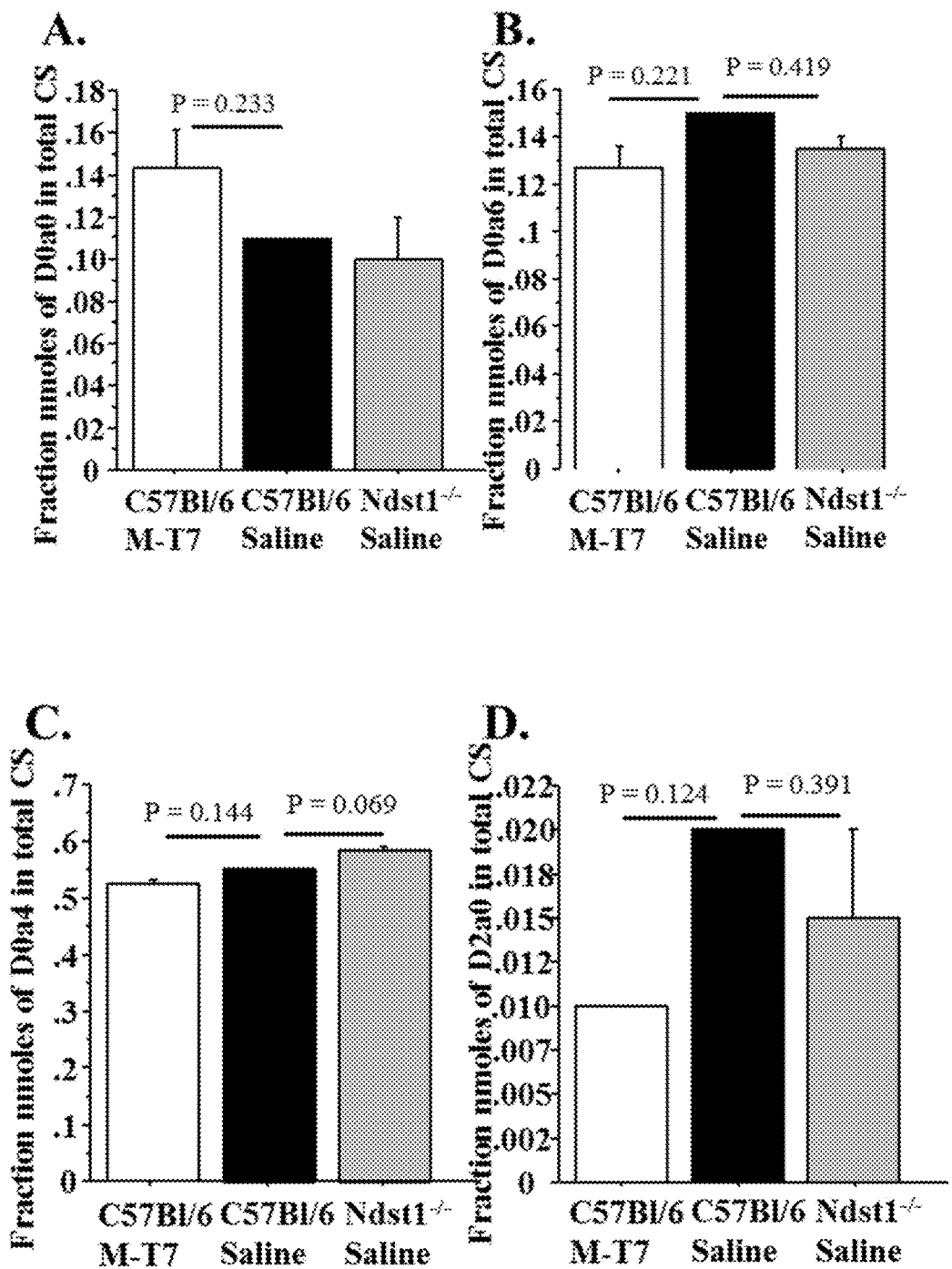
FIGS. 13A-P shows bar graphs demonstrating changes in disaccharide content, measured as nmoles (A-H) or percentage weight (I-P) of individual disaccharides in total CS extracts, from saline treated Ndst1$^{-/-}$ and saline or M-T7 treated WT mouse kidneys after 10 days treatment. CS disaccharide analysis of nmole content for D0a0 (A), D0a6 (B), D2a4 (C), D2a0 (D), D0a10 (E), D2a6 (F), and D2a4 (G). Multiple regression analysis of individual CS disaccharide weight changes (H) demonstrated significant predictive correlations for measured CS disaccharide content with potential to reduce rejection. CS disaccharide analysis of percentage weight CS disaccharides content for D0a0 (I), D0a6 (J), D2a4 (K), D2a0 (L), D0a10 (M), D2a6 (N), and D2a4 (O). Multiple regression analysis of individual CS disaccharide weight changes (P) demonstrated significant predictive correlations for measured CS disaccharide content with potential to reduce rejection.
Figures 13E, 13F, 13G, 13H:
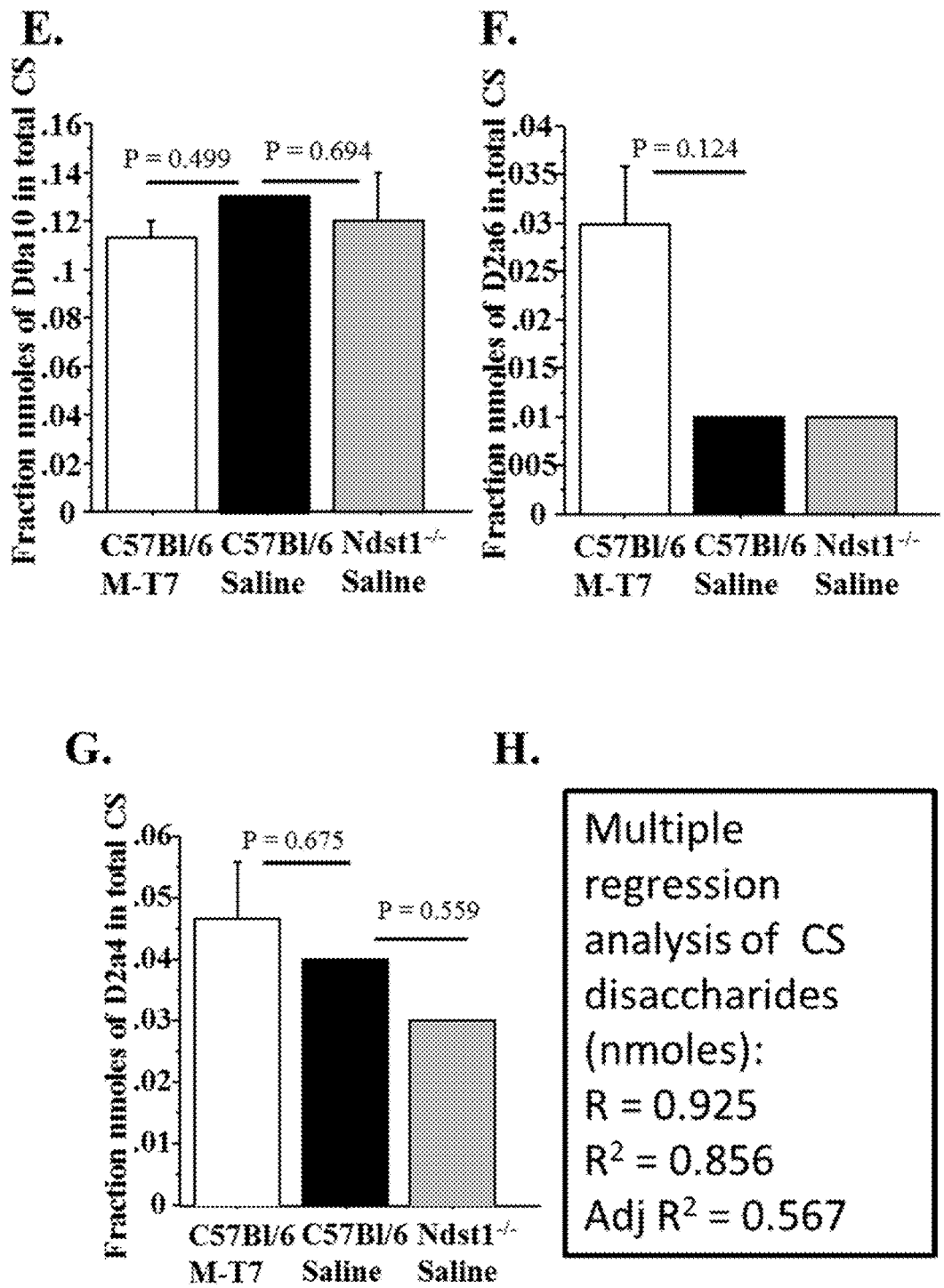
Figures 13I, 13J, 13K, 13L:
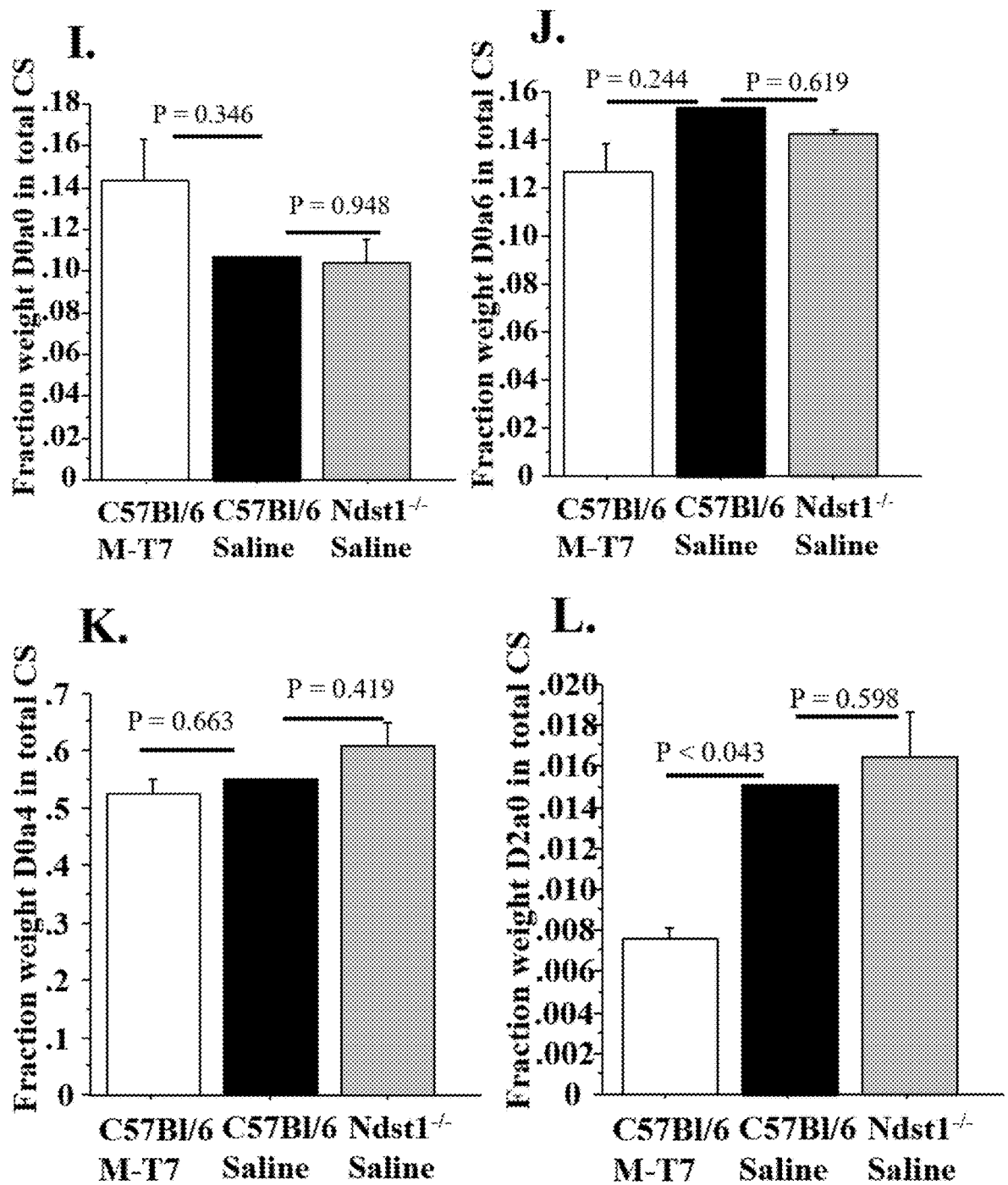

CS extracts were compared as a control; Ndst1 does not sulfate CS (see, FIGS. 13, 14). Significant increases were seen for D0a0 (P<0.041) and D0a4 when compared to saline treated C57Bl/6 mice in either Ndst1$^{-/-}$ or in M-T7 treated C57Bl/6 mice (FIG. 13). CS D2a0 was significantly decreased with all treatments when compared to saline treated WT mice (P<0.0001).

In order to determine whether there was a summation effect of all individual disaccharide changes in Ndst1$^{-/-}$ or M-T7 treated WT kidneys that could reduce risk of rejection overall, combined changes in renal disaccharide content for either HS or CS extracts were assessed by multiple linear regression analysis. Multiple regression analysis was used to calculate correlations between changes in individual HS disaccharide content and the predicted capacity of Ndst1 deficiency or M-T7 treatment in WT to reduce rejection. A significant correlation was detected when analyzing the 7 measured HS disaccharides in each kidney sample for percentage disaccharide content and also percent nmoles, with prediction of benefit for reducing acute rejection (FIG. 10). For disaccharide percentage weight, an excellent predictive value was demonstrated with R=0.993, R2=0.985 and adj R2=0.881 (FIG. 10H). When a similar analysis was performed for percentage moles sulfate in disaccharide isolates, a higher correlation was demonstrated with R=9.996, R2=0.992 and adj R2=0.935 (FIG. 10H) indicating a predictive value of 93.5% for altered acute rejection scores. MR analysis was repeated after removal of individual measurements and then re-applying the formulae generated to all disaccharide measures. The formulae accurately predicted reduced rejection scores for Ndst1$^{-/-}$ or M-T7 treated WT kidneys, or conversely increased rejection for saline treated WT controls in all but one out of a possible 9 samples.

Analysis of CS disaccharides had a lower correlation with R=0.851, R2=0.725, adj R2=0.174 for percentage disaccharide weights and R=0.925, R2=0.856 and adj R2=0.567 for mole percent disaccharide. The analysis of CS disaccharides thus indicates a lower predictive value of 17.4% for percent weight and 56.7% for mole percent (FIG. 13).

Figures 14A, 14B, 14C:
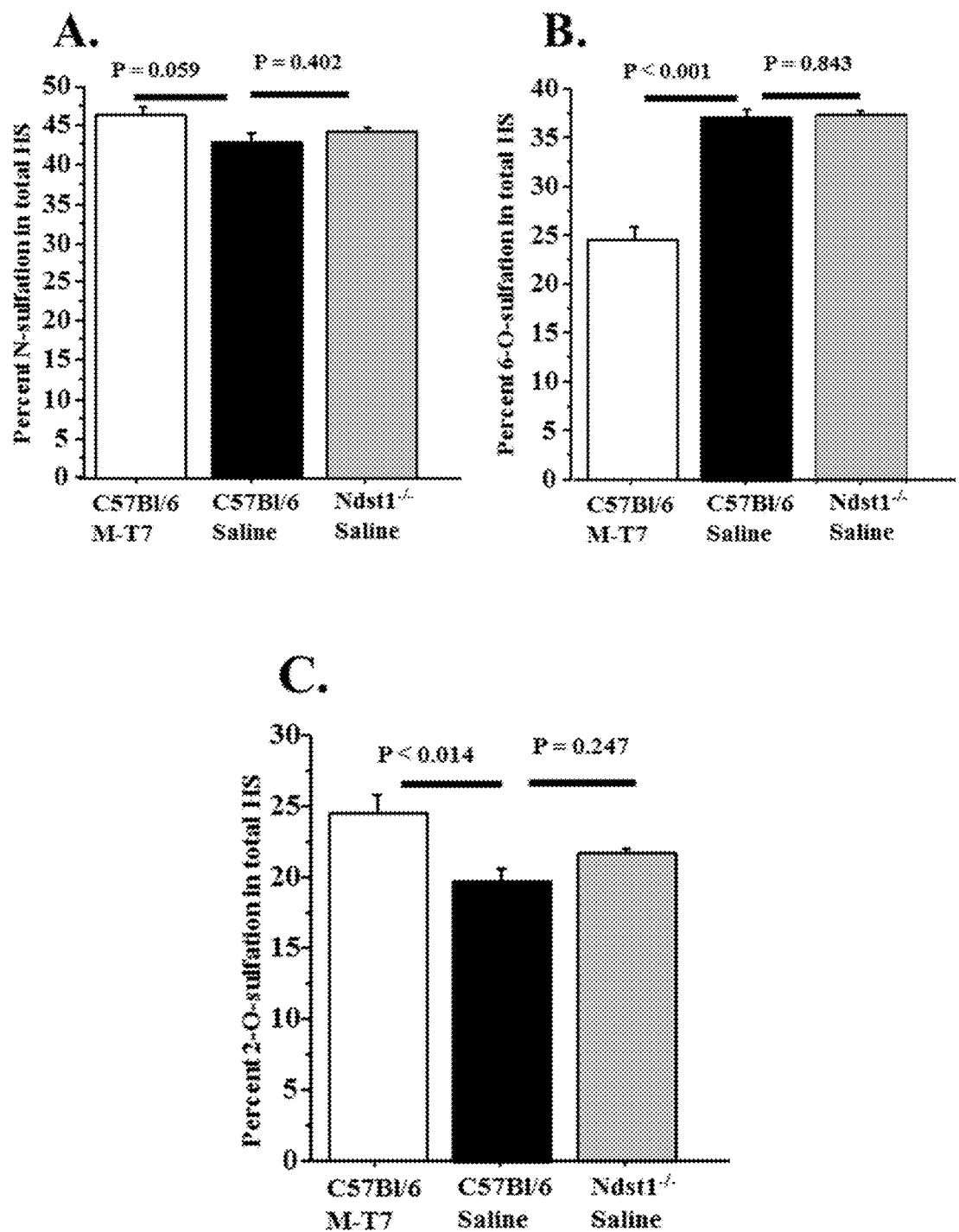
FIGS. 14A-F shows bar graphs demonstrating total N and O sulfation content changes in disaccharide content, measured as percent weight disaccharides HS (A-C) or CS (D-F) from saline treated Ndst1$^{-/-}$ and saline or M-T7 treated WT mouse kidneys after 10 days treatment; Total HS extract N sulfation (A), Total HS extract 6-0 sulfation (B), Total HS extract 2-0 sulfation (C), Total CS extract 6-0 sulfation (D), Total CS extract 2-0 sulfation (B). Total HS N sulfation and 2-0 sulfation CS are significantly increased with M-T7 treatment when compared to saline treated WT kidneys.
Figures 14D, 14E, 14F:
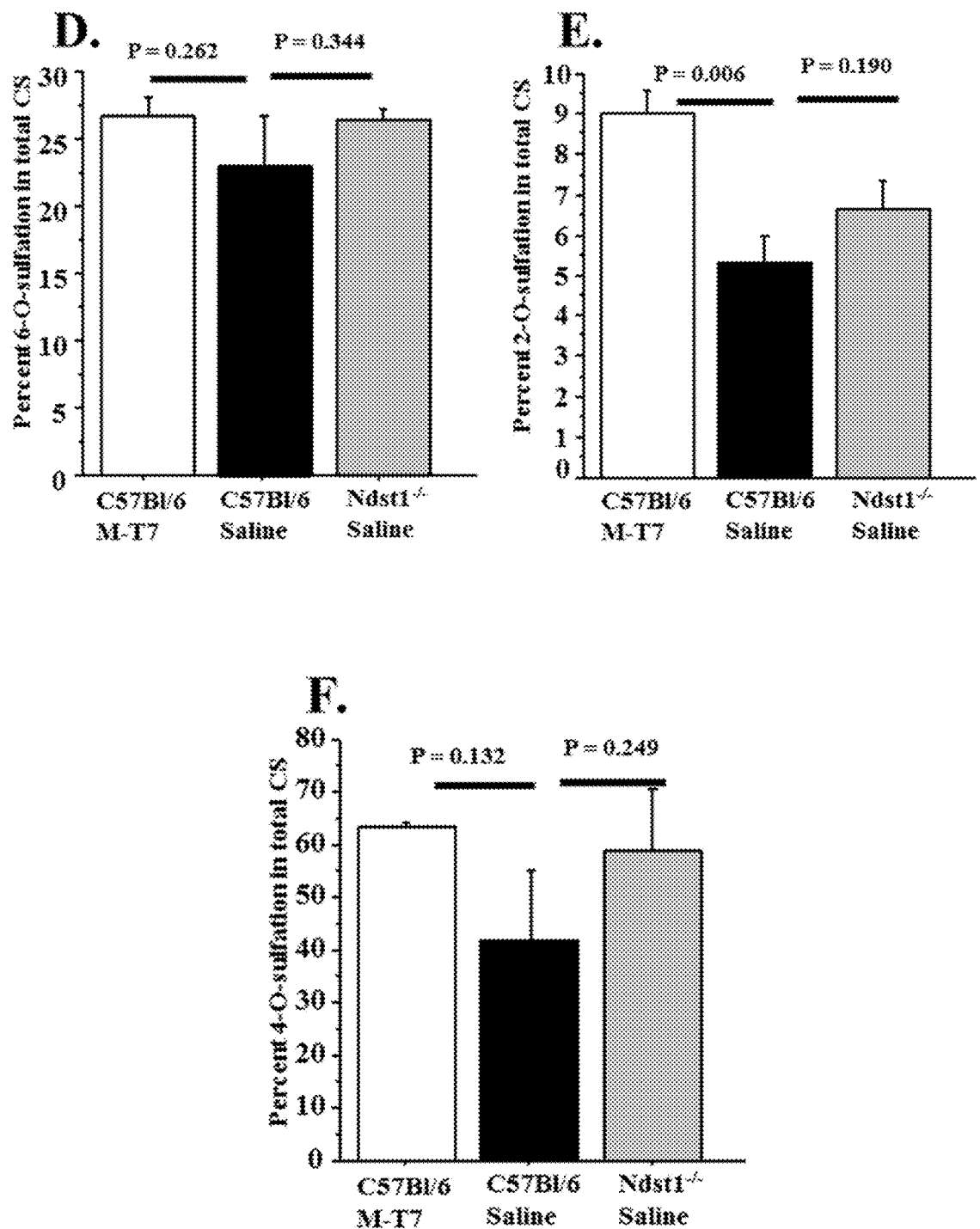

Altered total 6-O, 2-O or N sulfated disaccharide content was also calculated. Measured overall percent nmol sulfated disaccharide content was significantly decreased in M-T7 treated WT kidneys for HS disaccharides with 6-O sulfation (P<0.031) and increased for 2-O sulfated disaccharides (P<0.014), and borderline increased for N sulfated disaccharides (P<0.053) when compared to saline treated WT kidneys. Ndst1$^{-/-}$ kidneys with saline treatment had no significant detected changes in N, 2-O or 6-O sulfated disaccharides (P=0.401, P=0.247, P=0.647, respectively; FIG. 14).

The formulae generated from MR analysis using HS disaccharide content for predicting improved rejection are y=i+ax$_1$+bx$_2$+cx$_3$, where each x represents individual measured disaccharide content by weight or nmol and y represents rejection score (y is assigned the value of 1 for predicted reduced rejection and 0 for increased rejection).

The MR formulae generated are:

For HS disaccharide percentage weight—reduced rejection score (y)=40.434-2.596 (D0A0)-28.860 (D0S0)-64.604 (D0A6)-52.133 (D2A0)-84.492 (D0S6)-42.142 (D2S0)-59.666 (D2S6); and for HS disaccharide mole sulfate—reduced rejection score (y)=-129.713+257.887 (D0A0Mol S)+76.338 (D0S0 MolS)+95.211 (D0A6 MolS)+41.479 (D2A0 MolS)-40.845 (D0S6 MolS)+102.324 (D2S0 MolS)+15.352 (D2S6 MolS).

These findings suggest that a change in extracted HS disaccharides content has 88.1% to 93.5% predictive value for reduced acute rejection. Thus, modifying HS disaccharide content may predict associated reductions in acute rejection in donor organ allografts.

REFERENCES

1. Gottmann U, Mueller-Falcke A, Schnuelle P, Birck R, Nickeleit V, van der Woude F J, Yard B A, Braun C: Influence of hypersulfated and low molecular weight heparins on ischemia/reperfusion: injury and allograft rejection in rat kidneys. Transpl Int. 2007; 20: 542-549.
2. Radio S, Wood S, Wilson J, Lin H, Winters G, McManus B: Allograft vascular disease: comparison of heart and other grafted organs. Transplant Proc. 1996; 28: 496-499.
3. Bagnasco S M, Kraus E S. Intimal arteritis in renal allografts: new takes on an old lesion. Current opinion in organ transplantation. 2015; 20: 343-347.
4. Halloran P F, Famulski K, Reeve J: The molecular phenotypes of rejection in kidney transplant biopsies. Current opinion in organ transplantation. 2015; 20: 359-367.
5. Bedke J, Nelson P J, Kiss E, Muenchmeier N, Rek A, Behnes C L, Gretz N, Kungl A J, Gröne HJ: A novel CXCL8 protein-based antagonist in acute experimental renal allograft damage. Mol Immunol. 2010; 47: 1047-1057.
6. VanBuskirk A M, Pidwell D J, Adams P W, Orosz C G. Transplantation immunology. JAMA. 1997; 278:1993-1999.
7. Ali S, Malik G, Burns A, Robertson H, Kirby J A: Renal transplantation: examination of the regulation of chemokine binding during acute rejection. Transplantation. 2005; 79: 672-679.
8. Nelson P J, Krensky A M: Chemokines, chemokine receptors, and allograft rejection. Immunity. 2001; 14: 377-386.
9. Segerer S, Cui Y, Either F, et al. Expression of chemokines and chemokine receptors during human renal transplant rejection. American journal of kidney diseases: the official journal of the National Kidney Foundation. 2001; 37: 518-531.
10. Shimizu T, Tanabe T, Shirakawa H, Omoto K, Ishida H, Tanabe K. Clinical and pathological analysis of transplant glomerulopathy cases. Clinical Transplantation. 2012; 26 Suppl 24: 37-42.
11. Forsberg E, Kjellen L. Heparan sulfate: lessons from knockout mice. J Clin Invest. 2001; 108:175-180.
12. Ge X N, Ha S G, Rao A, Greenberg Y G, Rushdi M N, Esko J D, Sriramarao P: Endothelial and leukocyte heparan sulfates regulate the development of allergen-induced airway remodeling in a mouse model. Glycobiology. 2014; 24: 715-727.
13. Rops A L, Jacobs C W, Linssen P C, Boezeman J B, Lensen J F, Wijnhoven T J, van den Heuvel L P, van Kuppevelt T H, van der Vlag J, Berden J H: Heparan sulfate on activated glomerular endothelial cells and exogenous heparinoids influence the rolling and adhesion of leucocytes. Nephrol Dial Transplant. 2007; 22: 1070-1077.
14. Wang L, Fuster M, Sriramarao P, Esko J D. Endothelial heparan sulfate deficiency impairs L-selectin- and chemokine-mediated neutrophil trafficking during inflammatory responses. Nature Immunol. 2005; 6: 902-910.

15. Raines E W. The extracellular matrix can regulate vascular cell migration, proliferation, and survival: relationships to vascular disease. Int J Exp Pathol. 2000; 81:173-182.
16. Kuschert G S V, Coulin F, Power C A, Proudfoot A E, Hubbard R E, Hoogewerf A J, Wells T N. Glycosaminoglycans interact selectively with chemokines and modulate receptor binding and cellular responses. Biochemistry. 1999; 38: 12959-12968.
17. Proudfoot A E, Handel T M, Johnson Z, et al. Glycosaminoglycan binding and oligomerization are essential for the in vivo activity of certain chemokines. Proc Natl Acad Sci, USA. 2003; 100: 1885-1890.
18. Rops A L, Loeven M A$^1$, van Gemst J J$^1$, Eversen I$^1$, Van Wijk X M$^2$, Dijkman H B$^3$, van Kuppevelt T H, Berden J H, Rabelink T J, Esko J D, van der Vlag J: Modulation of heparan sulfate in the glomerular endothelial glycocalyx decreases leukocyte influx during experimental glomerulonephritis. Kidney Int. 2014; 86: 932-942.
19. Dai E, Liu L Y, Wang H, et al. Inhibition of chemokine-glycosaminoglycan interactions in donor tissue reduces mouse allograft vasculopathy and transplant rejection. PloS One. 2010; 5(5):e10510.
20. Proudfoot A E, Bonvin P, Power C A: Targeting chemokines: Pathogens can, why can't we? Cytokine. 2015; 74: 259-267.
21. Lucas A, McFadden G: Secreted immunomodulatory viral proteins as novel biotherapeutics. J Immunol. 2004; 173: 4765-4774.
22. Lalani A S, Ness T L, Singh R, Harrison J K, Seet B T, Kelvin D J, McFadden G, Moyer R W: Functional comparisons among members of the poxvirus T1/35 kDa family of soluble CC-chemokine inhibitor glycoproteins. Virology. 1998; 250: 173-184.
23. Upton C, Mossman K, McFadden G. Encoding of a homolog of the IFN-gamma receptor by myxoma virus. Science. 1992; 258: 1369-1372.
24. Bédard E L, Kim P, Jiang J, Parry N, Liu L, Wang H, Garcia B, Li X, McFadden G, Lucas A, Zhong R. Chemokine-binding viral protein M-T7 prevents chronic rejection in rat renal allografts. Transplantation. 2003; 76:249-252.
25. Liu L, Dai E, Miller L, et al. Viral chemokine-binding proteins inhibit inflammatory responses and aortic allograft transplant vasculopathy in rat models. Transplantation. 2004; 77: 1652-1660.
26. Liu L, Lalani A, Dai E, et al. The viral anti-inflammatory chemokine-binding protein M-T7 reduces intimal hyperplasia after vascular injury. J Clin Invest. 2000; 105:1613-1621.
27. Bartee M Y, Chen H, Dai E, Liu L Y, Davids J A, Lucas A: Defining the anti-inflammatory activity of a potent myxomaviral chemokine modulating protein, M-T7, through site directed mutagenesis. Cytokine. 2014; 65: 79-87.
28. Reeve J, Einecke G, Mengel M, Sis B, Kayser N, Kaplan B, Halloran P F. Diagnosing rejection in renal transplants: a comparison of molecular- and histopathology-based approaches. Am J Transplant. 2009; 9: 1802-1810.
29. Chen H, Zheng D, Davids J, Bartee M Y, Dai E, Liu L, Petrov L, Macaulay C, Thoburn R, Sobel E, Moyer R, McFadden G, Lucas A: Viral serpin therapeutics from concept to clinic. Methods Enzymol. 2011; 499: 301-329.
30. Pomin, V. H., Y. Park, R. Huang, C. Heiss, J. S. Sharp, P. Azadi, and J. H. Prestegard. 2012. Exploiting enzyme specificities in digestions of chondroitin sulfates A and C: production of well-defined hexasaccharides. Glycobiology. 22: 826-838.
31. Christov A, Korol R M, Dai E, Liu L, Guan H, Bernards M A, Cavers P B, Susko D, Lucas A. In vivo optical analysis of quantitative changes in collagen and elastin during arterial remodeling. Photochem Photobiol. 2005; 81: 457-466.
32. Lawrence, R.; Lu, H.; Rosenberg, R. D.; Esko, J. D.; Zhang, L. Nat. Methods 2008, 5, 291.
33. De Muro P1, Faedda R, Masala A, Lepedda A J, Zinellu E, Ciccarese M, Cossu M, Pala P G, Satta R P, Formato M: Kidney post-transplant monitoring of urinary glycosaminoglycans/proteoglycans and monokine induced by IFN-gamma (MIG). Clin Exp Med. 2013; 13: 59-65.
34. Reitsma S, Slaaf D W, Vink H, van Zandvoort M A, oude Egbrink M G. The endothelial glycocalyx: composition, functions, and visualization. Pflugers Archiv. 2007; 454: 345-359.
35. Rienstra H, Katta K, Celie JWAM, van Goor H, Navis G, van den Born J, Hillebrands J-L: Differential expression of proteoglycans in tissue remodeling and lymphangiogenesis after experimental renal transplantation in rats. PloS One. 2010; 5: e9095.35.
36. Yard B A, Lorentz C P, Herr D, van der Woude F J. Sulfation-dependent down-regulation of interferon-gamma-induced major histocompatibility complex class I and II and intercellular adhesion molecule-1 expression on tubular and endothelial cells by glycosaminoglycans. Transplantation. 1998; 66: 1244-1250.
37. Celie J W, Rutjes N W, Keuning E D, Soininen R, Heljasvaara R, Pihlajaniemi T, Drager A M, Zweegman S, Kessler F L, Beelen R H, Florquin S, Aten J, van den Born J: Subendothelial heparan sulfate proteoglycans become major L-selectin and monocyte chemoattractant protein-1 ligands upon renal ischemia/reperfusion. Am J Pathol. 2007; 170: 1865-1878.
38. Joosten S A, van Dixhoorn M G, Borrias M C, Benediktsson H, van Veelen P A, van Kooten C, Paul L C. Antibody response against perlecan and collagen types IV and VI in chronic renal allograft rejection in the rat. Am J Pathol. 2002; 160: 1301-1310.
39. Alhasan A A, Spielhofer J, Kusche-Gullberg M, Kirby J A, Ali S: Role of 6-O-sulfated heparan sulfate in chronic renal fibrosis. J Biol Chem. 2014; 289: 20295-20306.
40. Libby P, Pober J S: Chronic rejection. Immunity. 2001; 14(4):387-397.
41. Hayry P: Pathophysiology of chronic rejection. Transplant Proceedings. 1996; 28(6 Suppl 1):7-10.

What is claimed is:

1. A method of treating or reducing rejection of a transplant, the method comprising contacting an organ with a therapeutically effective amount of a polypeptide comprising the sequence set forth in SEQ ID NO: 2 or 3.

2. The method of claim 1, wherein the polypeptide inhibits CC chemokine-mediated cell migration.

3. The method of claim 2, wherein the polypeptide disrupts chemokine-glycosaminoglycan interactions.

4. The method of claim 1, wherein the transplant is a kidney, heart, lung, liver, pancreas or stem cell transplant.

5. The method of claim 1, wherein the organ is contacted with the polypeptide one to ten days before transplantation.

6. A method of modulating T cell receptor (TCR) expression in vitro or in vivo, the method comprising: contacting a cell in vitro, or contacting an organ prior to transplantation, with a therapeutically effective amount of a polypeptide comprising the sequence set forth in SEQ ID NO: 2 or 3.

7. The method of claim 6, wherein the polypeptide reduces TCR expression as compared to a reference level.

8. The method of claim 6, wherein the TCR is a CD3+ cell surface marker.

9. A method of treating a kidney prior to transplantation, the method comprising contacting the kidney with a polypeptide comprising the sequence set forth in SEQ ID NO: 2 or 3.

10. The method of claim 9, wherein polypeptide reduces rejection of the transplanted kidney.

11. The method of claim 9, wherein the polypeptides reduces T cell receptor expression in the kidney prior to transplantation or after transplantation as compared to a reference level.

* * * * *

UNITED STATES PATENT AND TRADEMARK OFFICE
CERTIFICATE OF CORRECTION

PATENT NO. : 10,653,760 B2
APPLICATION NO. : 15/742092
DATED : May 19, 2020
INVENTOR(S) : Alexandra Rose Lucas It is certified that error appears in the above-identified patent and that said Letters Patent is hereby corrected as shown below:

In the Specification

At Column 1, Line 22, please replace the paragraph and insert the following new paragraph:
--STATEMENT REGARDING FEDERALLY FUNDED RESEARCH
This invention was made with government support under grant number HL100202 awarded by National Institutes of Health. The government has certain rights in the invention.--

Signed and Sealed this
Eighteenth Day of August, 2020

Andrei Iancu
*Director of the United States Patent and Trademark Office*